United States Patent
Hirose

(10) Patent No.: US 9,804,080 B2
(45) Date of Patent: Oct. 31, 2017

(54) COLOR SENSOR AND ELECTRONIC DEVICE HAVING THE SAME

(71) Applicant: Semiconductor Energy Laboratory Co., Ltd., Atsugi-shi, Kanagawa-ken (JP)

(72) Inventor: Atsushi Hirose, Atsugi (JP)

(73) Assignee: Semiconductor Energy Laboratory Co., Ltd., Kanagawa-ken (JP)

( * ) Notice: Subject to any disclaimer, the term of this patent is extended or adjusted under 35 U.S.C. 154(b) by 537 days.

(21) Appl. No.: 13/959,044

(22) Filed: Aug. 5, 2013

(65) Prior Publication Data

US 2013/0313670 A1     Nov. 28, 2013

Related U.S. Application Data

(62) Division of application No. 12/498,662, filed on Jul. 7, 2009, now Pat. No. 8,502,131.

(30) Foreign Application Priority Data

Jul. 10, 2008   (JP) .................. 2008-180776

(51) Int. Cl.
 *H01J 40/14*   (2006.01)
 *G01N 21/25*   (2006.01)
 (Continued)

(52) U.S. Cl.
 CPC ......... *G01N 21/255* (2013.01); *H01L 27/144* (2013.01); *H01L 27/14621* (2013.01);
 (Continued)

(58) Field of Classification Search
 CPC . G01N 21/255; H01L 27/144; H01L 27/3269; H01L 27/3276; H01L 27/14621;
 (Continued)

(56) References Cited

U.S. PATENT DOCUMENTS

| 4,996,417 A | 2/1991 | Shinomiya |
| 5,261,156 A | 11/1993 | Mase et al. |

(Continued)

FOREIGN PATENT DOCUMENTS

| EP | 1453097 A | 9/2004 |
| JP | 07-014880 | 1/1995 |

(Continued)

OTHER PUBLICATIONS

US 7,359,010, 04/2008, Yamazaki et al. (withdrawn)
Korean Office Action (Application No. 2009-0063027) dated May 20, 2015.

*Primary Examiner* — Thanh Luu
*Assistant Examiner* — Kevin Wyatt
(74) *Attorney, Agent, or Firm* — Robinson Intellectual Property Law Office; Eric J. Robinson

(57) ABSTRACT

A color sensor with a plurality of optical sensors in which the number of terminals for connection with the outside can be reduced. The color sensor includes a plurality of optical sensors each provided with a photoelectric conversion element and an optical filter over a light-transmitting substrate. The optical filters in the plurality of optical sensors have light-transmitting characteristics different from each other. The plurality of optical sensors is mounted over an interposer including a plurality of terminal electrodes for electrical connection with an external device. The interposer includes a wiring having a plurality of branches for electrical connection between the terminal electrode for inputting a high power supply potential to the plurality of optical sensors and a wiring having a plurality of branches for electrical connection between the terminal electrode for inputting a low power supply potential to the plurality of optical sensors.

20 Claims, 22 Drawing Sheets

(51) Int. Cl.
*H01L 27/146* (2006.01)
*H01L 27/144* (2006.01)
*G09G 3/34* (2006.01)

(52) U.S. Cl.
CPC ......... *G09G 3/3406* (2013.01); *G09G 3/3413* (2013.01); *G09G 2320/0626* (2013.01); *G09G 2320/0666* (2013.01); *G09G 2360/144* (2013.01); *G09G 2360/145* (2013.01); *H01L 27/14623* (2013.01); *H01L 27/14685* (2013.01)

(58) Field of Classification Search
CPC ......... G02F 1/133509; G02F 1/133512; G02F 1/133514
USPC .......................................... 257/432; 250/226
See application file for complete search history.

(56) References Cited

U.S. PATENT DOCUMENTS

| | | | |
|---|---|---|---|
| 5,401,330 A | 3/1995 | Saito et al. | |
| 5,468,681 A * | 11/1995 | Pasch | G03F 7/70433 156/329 |
| 5,757,456 A | 5/1998 | Yamazaki et al. | |
| 5,834,327 A | 11/1998 | Yamazaki et al. | |
| 6,118,502 A | 9/2000 | Yamazaki et al. | |
| 6,362,866 B1 | 3/2002 | Yamazaki et al. | |
| 6,855,961 B2 | 2/2005 | Maruyama et al. | |
| 6,882,012 B2 | 4/2005 | Yamazaki et al. | |
| 6,900,873 B2 | 5/2005 | Yamazaki et al. | |
| 7,050,138 B1 | 5/2006 | Yamazaki et al. | |
| 7,056,810 B2 | 6/2006 | Yamazaki et al. | |
| 7,067,395 B2 | 6/2006 | Maruyama et al. | |
| 7,214,555 B2 | 5/2007 | Yamazaki et al. | |
| 7,265,402 B2 | 9/2007 | Koyanagi | |
| 7,271,858 B2 | 9/2007 | Yamazaki et al. | |
| 7,352,044 B2 | 4/2008 | Yamada et al. | |
| 7,446,843 B2 | 11/2008 | Yamazaki et al. | |
| 7,561,219 B2 | 7/2009 | Seo et al. | |
| 7,824,950 B2 | 11/2010 | Monma et al. | |
| 8,049,292 B2 | 11/2011 | Takahashi et al. | |
| 8,053,816 B2 | 11/2011 | Arao et al. | |
| 8,081,265 B2 | 12/2011 | Seo et al. | |
| 8,415,664 B2 | 4/2013 | Arao et al. | |
| 2002/0053673 A1 | 5/2002 | Misawa et al. | |
| 2003/0071953 A1 | 4/2003 | Yamazaki et al. | |
| 2003/0218245 A1 * | 11/2003 | Matsuzawa | H01L 23/49838 257/734 |
| 2004/0121516 A1 * | 6/2004 | Yamazaki | C30B 13/24 438/106 |
| 2004/0130020 A1 * | 7/2004 | Kuwabara | H01L 21/2007 257/723 |
| 2004/0169271 A1 | 9/2004 | Igarashi et al. | |
| 2005/0070038 A1 | 3/2005 | Yamazaki et al. | |
| 2005/0121672 A1 | 6/2005 | Yamazaki et al. | |
| 2005/0157242 A1 | 7/2005 | Yamazaki et al. | |
| 2006/0044300 A1 | 3/2006 | Koyama et al. | |
| 2006/0065960 A1 | 3/2006 | Maruyama et al. | |
| 2006/0091300 A1 | 5/2006 | Nishimura et al. | |
| 2006/0220211 A1 | 10/2006 | Yamazaki et al. | |
| 2006/0270195 A1 | 11/2006 | Yamada et al. | |
| 2006/0273437 A1 | 12/2006 | Beer et al. | |
| 2007/0115416 A1 | 5/2007 | Yamazaki et al. | |
| 2007/0268206 A1 * | 11/2007 | Kinoshita | G06F 3/0412 345/30 |
| 2007/0290302 A1 * | 12/2007 | Nakagawa | H01L 23/3185 257/668 |
| 2008/0106918 A1 | 5/2008 | Shimizu et al. | |
| 2008/0188022 A1 | 8/2008 | Yamazaki et al. | |
| 2008/0265351 A1 * | 10/2008 | Monma | H01L 27/14618 257/432 |
| 2009/0194154 A1 | 8/2009 | Takahashi et al. | |
| 2010/0084642 A1 * | 4/2010 | Hanari | H01L 27/3269 257/40 |
| 2011/0012218 A1 | 1/2011 | Monma et al. | |

FOREIGN PATENT DOCUMENTS

| | | |
|---|---|---|
| JP | 08-250745 | 9/1996 |
| JP | 08-264796 | 10/1996 |
| JP | 2001-064029 | 3/2001 |
| JP | 2003-255386 | 9/2003 |
| JP | 2006-135320 | 5/2006 |
| JP | 2007-273961 A | 10/2007 |
| JP | 2007-310628 A | 11/2007 |
| JP | 2008-124568 | 5/2008 |
| KR | 2006-0027137 A | 3/2006 |
| WO | WO-03/041174 | 5/2003 |

* cited by examiner

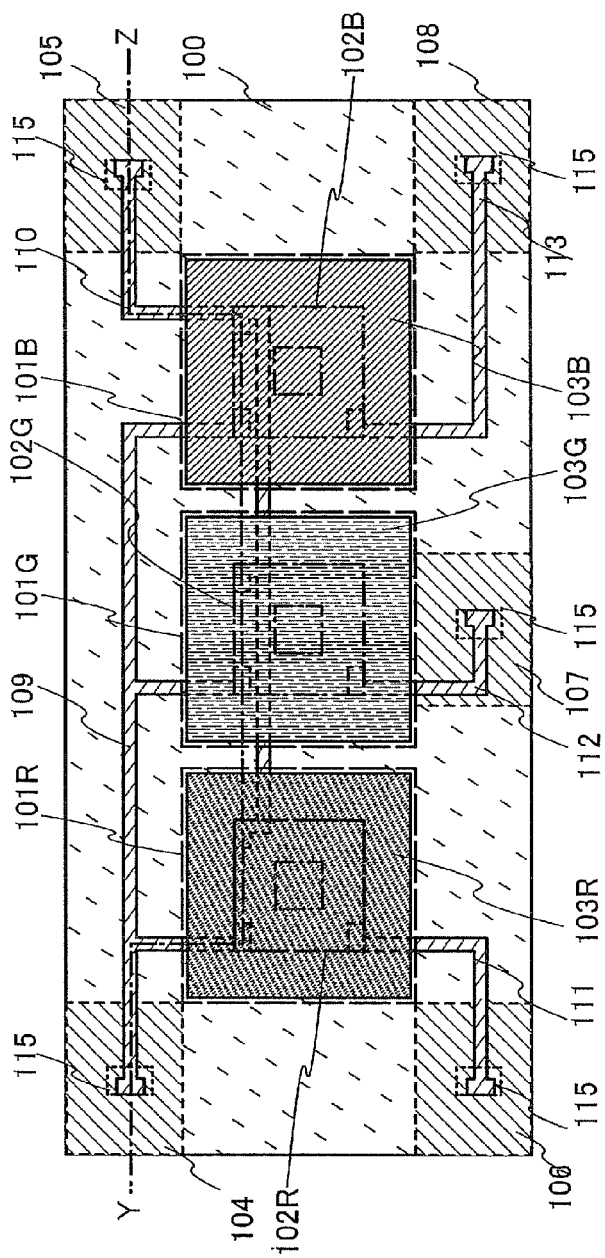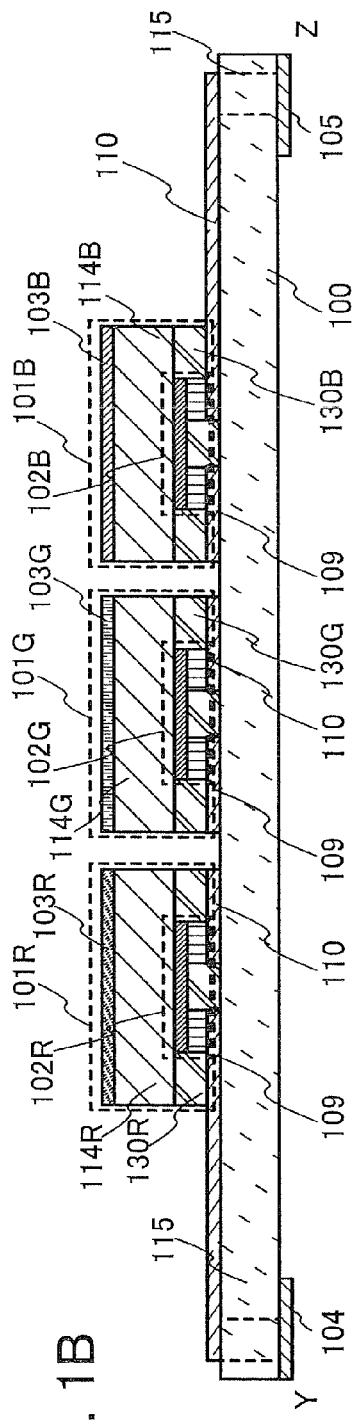

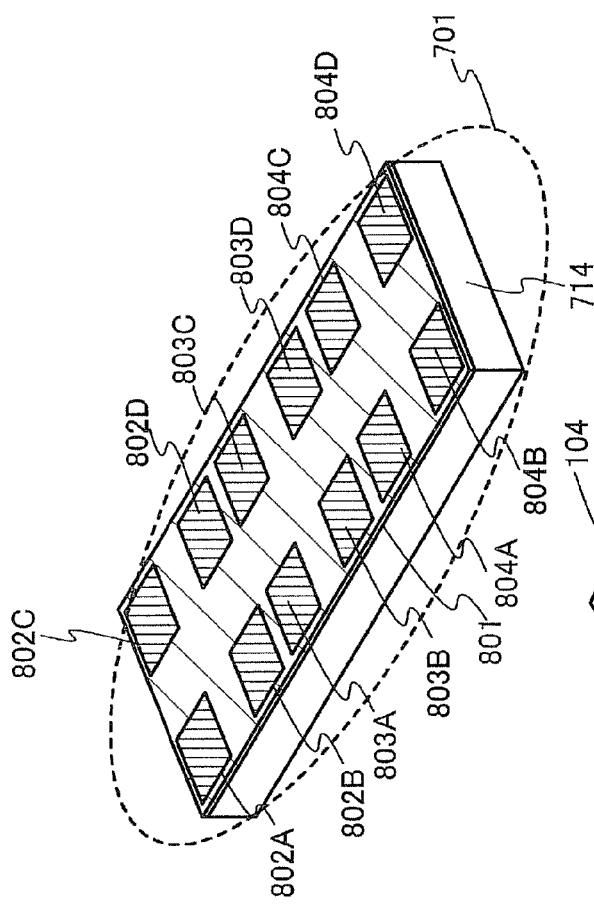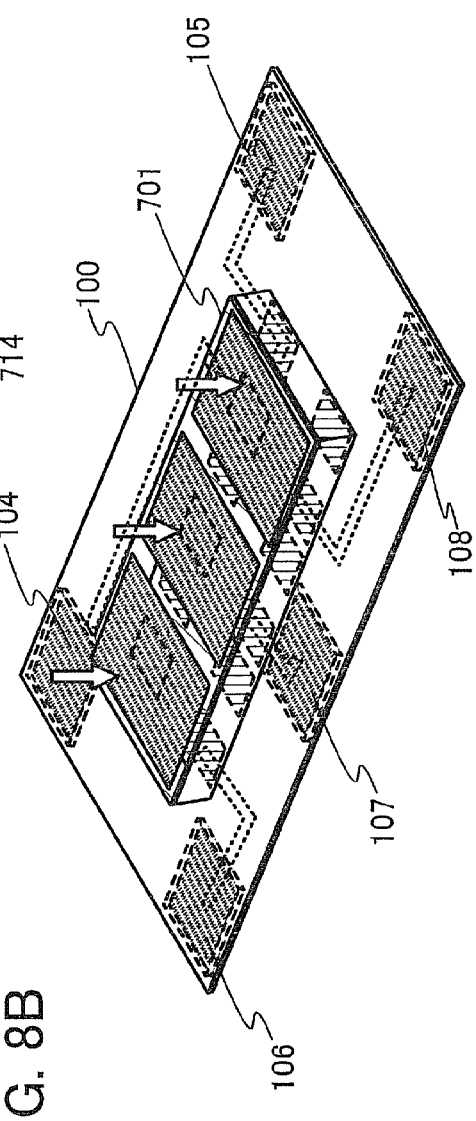
FIG. 8A
FIG. 8B

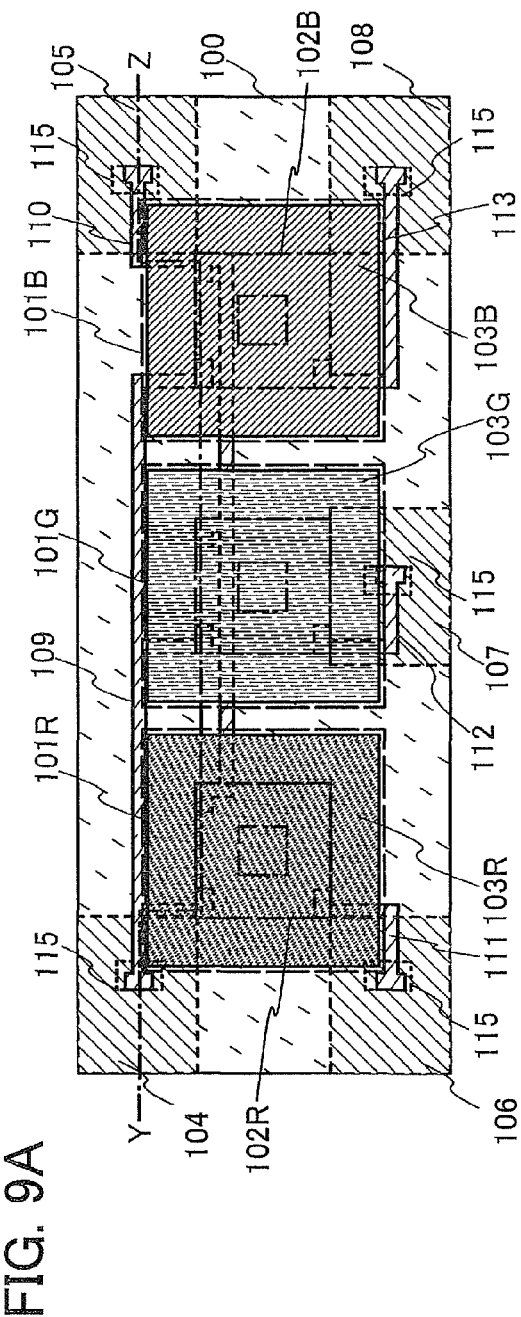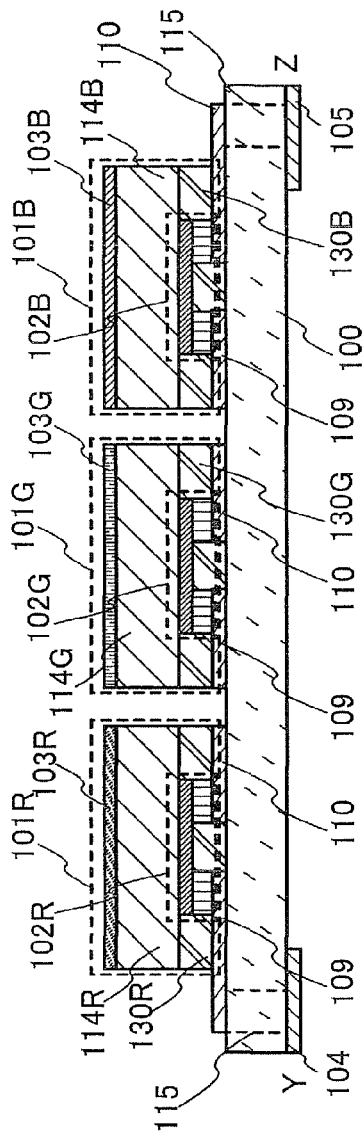
FIG. 9A
FIG. 9B

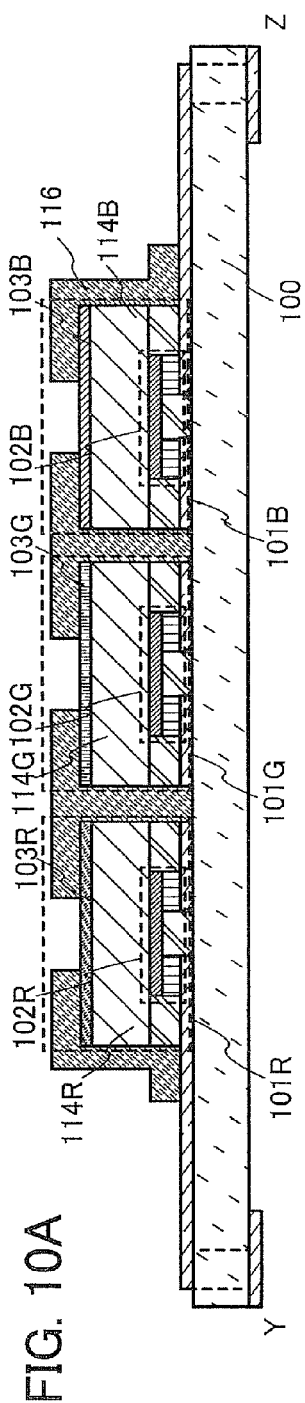
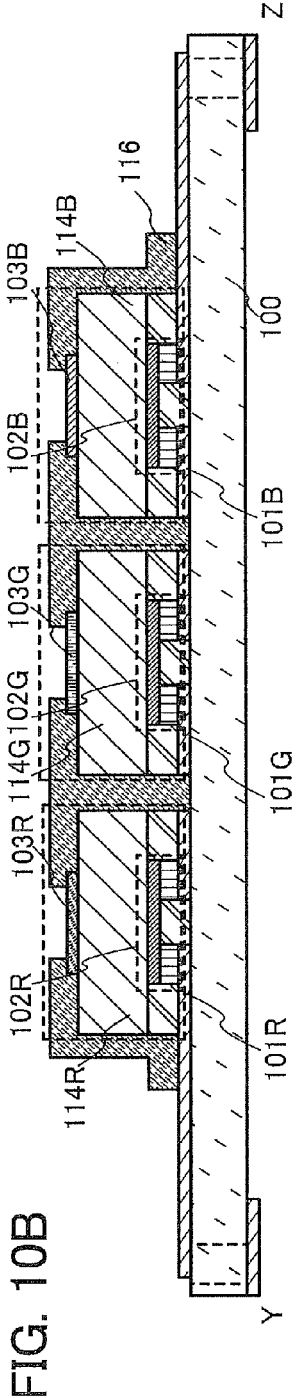
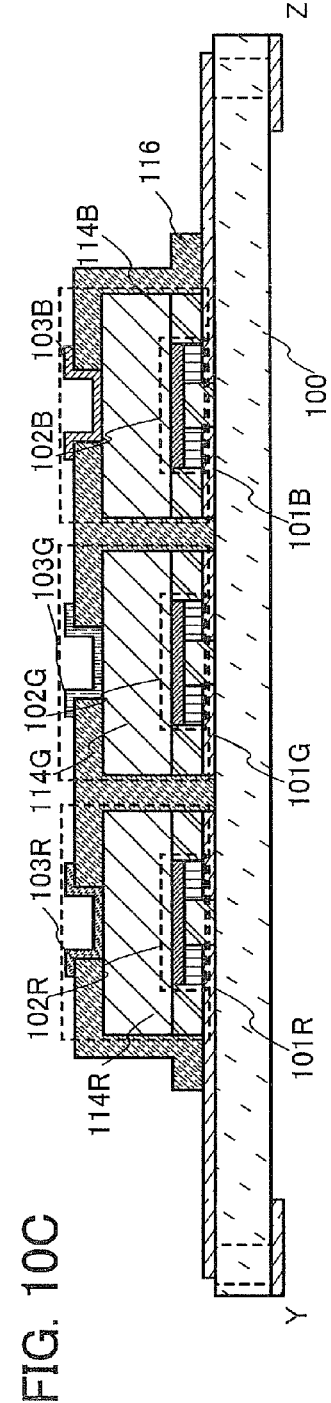
FIG. 10A
FIG. 10B
FIG. 10C

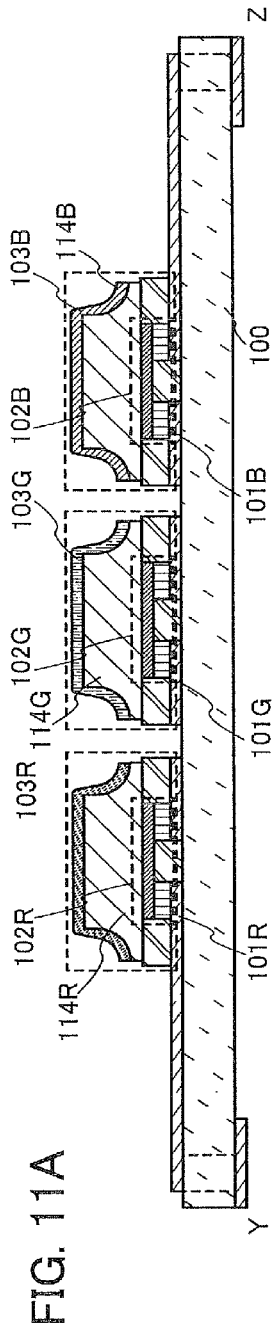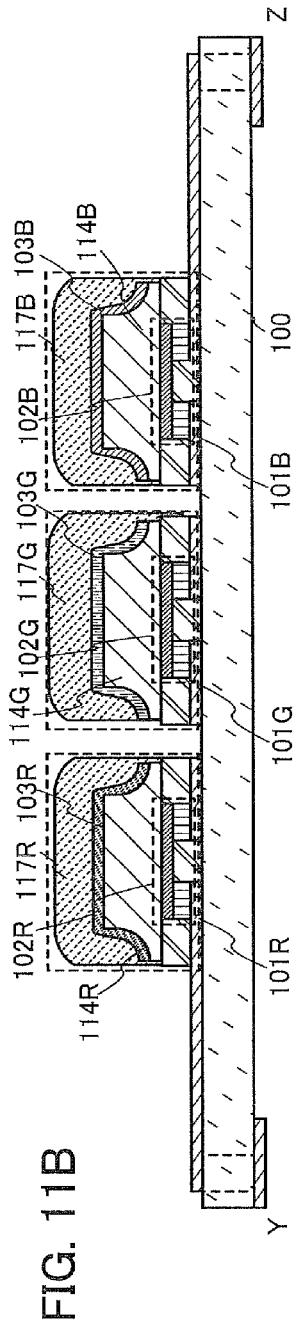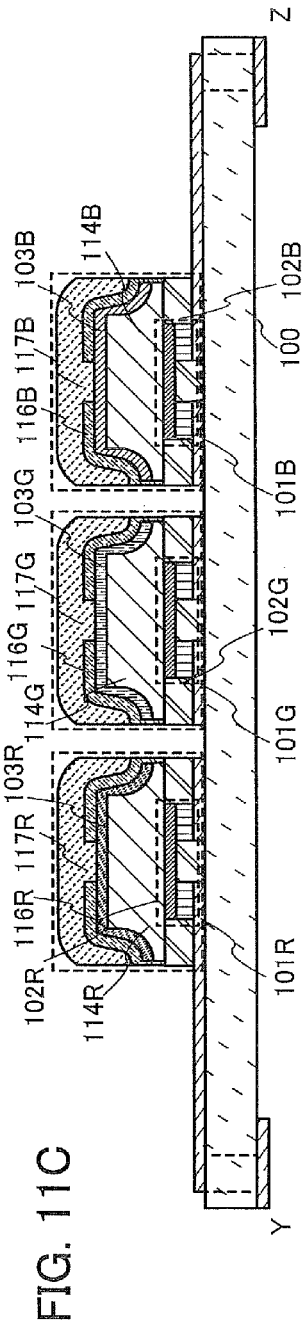

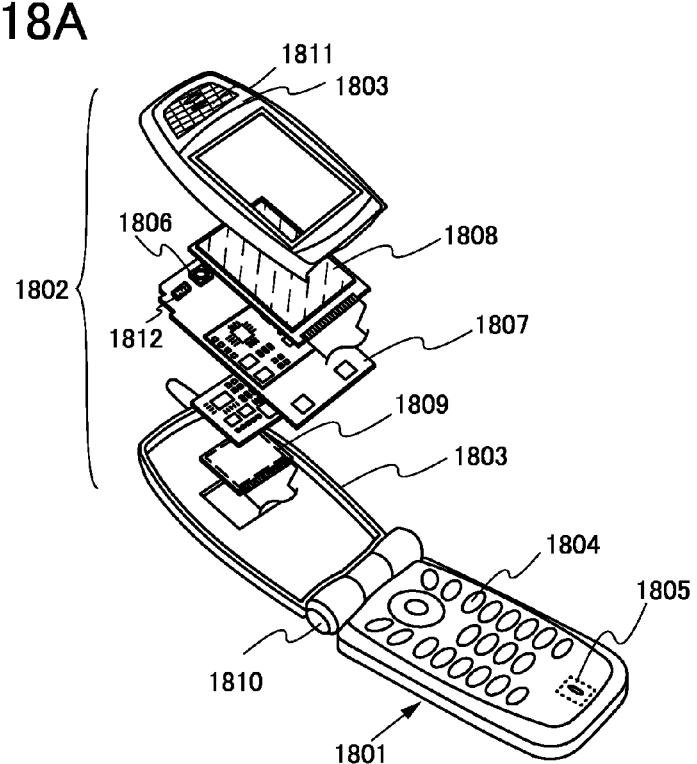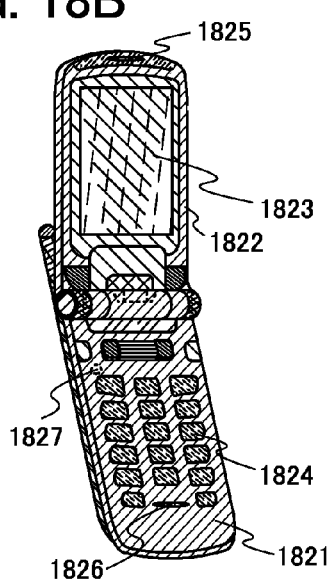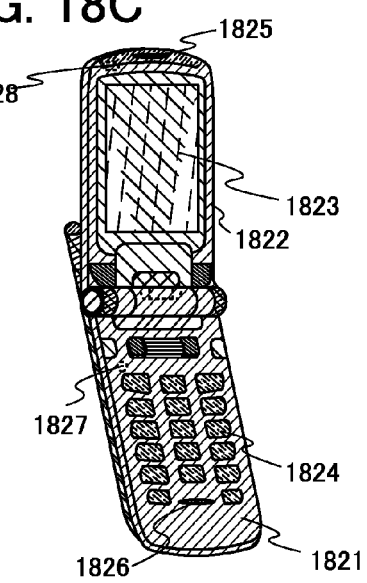

COLOR SENSOR AND ELECTRONIC DEVICE HAVING THE SAME

BACKGROUND OF THE INVENTION

1. Field of the Invention

The present invention relates to a color sensor. Moreover, the present invention relates to an electronic device having the color sensor.

2. Description of the Related Art

A number of optical sensors that convert the intensity of light into electrical signals and output have been known and have sensitivity to electromagnetic waves ranging from ultra violet rays to infrared rays. A number of optical sensors are used for adjustment of illuminance in accordance with living environment of humans beings and for devices which require on/off control.

In some display devices, ambient brightness of the display device is detected so that display luminance is adjusted. This is because unnecessary electric power of the display device can be reduced by increasing visibility through detecting ambient brightness by an optical sensor and obtaining appropriate display luminance. For example, examples of display devices which have an optical sensor for adjusting luminance include a mobile phone and a computer with a display portion. In addition, as well as the ambient brightness of the display device, luminance of the backlight of a display device, in particular, a liquid crystal display device is also detected by an optical sensor to adjust luminance of a display screen.

The optical sensor includes a photoelectric conversion element such as a photo diode in a light sensing portion and can detect illuminance based on the amount of current which flows to the photoelectric conversion element. Patent Document 1 discloses a structure in which photo current generated by the photoelectric conversion element is made to flow to a diode element in order to obtain an output signal as a voltage value which has been subjected to logarithmic compression so that a dynamic range of the illuminance of the optical sensor is obtained. Note that the logarithmic compression is to obtain a current value or a voltage value output with the illuminance of light which enters the photoelectric conversion element, that is, the value of the photo current used as a variable, so that the output current value or voltage value is used as a logarithmic function. Moreover, Patent Document 1 discloses a structure in which an analog value obtained on the basis of current which flows from a photo diode in accordance with the amount of incident light is converted into a digital value to be used as an output signal.

Further, Patent Document 2 discloses a color sensor in which a plurality of optical sensors is provided over a substrate to receive light with different wavelengths.

[Patent Document 1] Japanese Published Patent Application No. 2008-124568

[Patent Document 2] Japanese Published Patent Application No. 2006-135320

SUMMARY OF THE INVENTION

The color sensor provided with the plurality of optical sensors, which is disclosed in Patent Document 2, is mounted over a substrate after dividing a large substrate with respect to a semiconductor element layer. Since the plurality of optical sensors mounted over the substrate can be selected to be provided, optical sensors having different light-transmitting characteristics can be mounted as a combination, and thus the color sensor can be manufactured.

However, in the current situation, as the optical sensor is further integrated and miniaturized as disclosed in Patent Document 1, the number of terminals in the optical sensor is increased. Therefore, since the number of terminals is increased in proportion to the number of optical sensors which are combined and mounted when the color sensor is manufactured, the number of terminal electrodes for electrical connection with an external device is increased on the substrate side.

An embodiment of the present invention is devised to solve the above-described problem. An object is to provide a color sensor which can achieve decrease in the number of terminal electrodes for electrical connection with an external device.

According to one embodiment of the present invention, a color sensor includes a plurality of optical sensors each provided with a photoelectric conversion element and an optical filter over a light-transmitting substrate. The optical filters in the plurality of optical sensors have light-transmitting characteristics different from each other. The plurality of optical sensors is mounted over an interposer including a plurality of terminal electrodes for electrical connection with an external device. The interposer has a wiring with a plurality of branches for electrical connection between the terminal electrode for inputting a high power supply potential and the plurality of optical sensors and a wiring with a plurality of branches for electrical connection between the terminal electrode for inputting a low power supply potential and the plurality of optical sensors.

According to one embodiment of the present invention, a color sensor includes an optical sensor provided with a plurality of photoelectric conversion elements and a plurality of optical filters over a light-transmitting substrate. The plurality of optical filters have light-transmitting characteristics different from each other. The optical sensor is mounted over an interposer including a plurality of terminal electrodes for electrical connection with an external device. The interposer has a wiring with a plurality of branches for electrical connection between the terminal electrode for inputting a high power supply potential and the optical sensor and a wiring with a plurality of branches for electrical connection between the terminal electrode for inputting a low power supply potential and the optical sensor.

According to one embodiment of the present invention, a color sensor includes a plurality of optical sensors each provided with a photoelectric conversion element, a photoelectric conversion circuit portion, and an optical filter over a light-transmitting substrate. The optical filters in the plurality of optical sensors have light-transmitting characteristics different from each other. The plurality of optical sensors is mounted over an interposer including a plurality of terminal electrodes for electrical connection with an external device. The interposer has a wiring with a plurality of branches for electrical connection between the terminal electrode for inputting a high power supply potential and the plurality of optical sensors and a wiring with a plurality of branches for electrical connection between the terminal electrode for inputting a low power supply potential and the plurality of optical sensors. The plurality of terminal electrodes and the photoelectric conversion circuit portion are provided so as to be apart from each other.

According to one embodiment of the present invention, a color sensor includes an optical sensor provided with a plurality of photoelectric conversion elements, a plurality of photoelectric conversion circuit portions, and a plurality of optical filters over a light-transmitting substrate. The plurality of optical filters has light-transmitting characteristics different from each other. The optical sensor is mounted over an interposer including a plurality of terminal electrodes for electrical connection with an external device. The interposer has a wiring with a plurality of branches for electrical connection between the terminal electrode for inputting a high power supply potential and the optical sensor and a wiring with a plurality of branches for electrical connection between the terminal electrode for inputting a low power supply potential and the optical sensor. The plurality of terminal electrodes and the plurality of photoelectric conversion circuit portions are formed so as to be apart from each other.

According to an embodiment of the present invention, a color sensor which can achieve decrease in the number of terminal electrodes for connection with the outside can be obtained.

BRIEF DESCRIPTION OF THE DRAWINGS

FIGS. 1A and 1B are diagrams illustrating a color sensor.
FIGS. 8A and 8B are diagrams illustrating a color sensor.
FIGS. 9A and 9B are diagrams illustrating a color sensor.
FIGS. 10A to 10C are diagrams each illustrating a color sensor.
FIGS. 11A to 11C are diagrams each illustrating a color sensor.
FIGS. 18A to 18C are diagrams each illustrating an electronic device provided with a color sensor.

DETAILED DESCRIPTION OF THE INVENTION

Figure 2A:
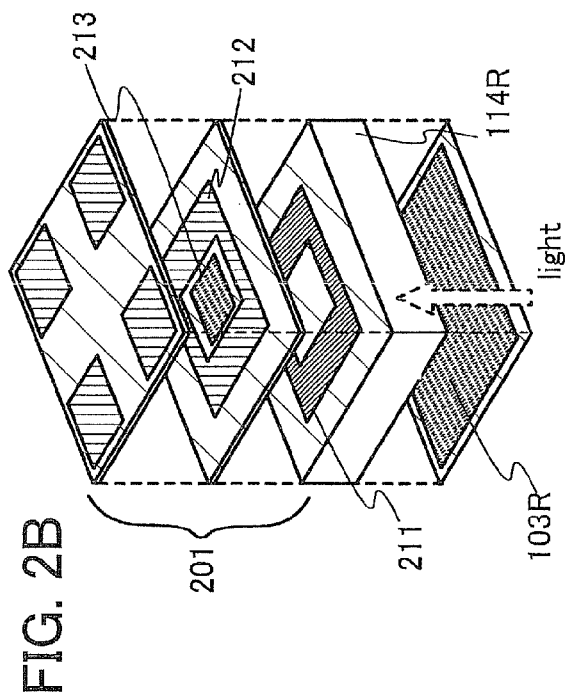
FIGS. 2A to 2C are diagrams each illustrating a color sensor.

Embodiments of the present invention will be described below with reference to the accompanying drawings. However, the present invention can be carried out in many different modes, and it is easily understood by those skilled in the art that the mode and detail can be variously changed without departing from the spirit and scope of the present invention. Therefore, the present invention is not to be construed as being limited to description in the embodiments. Note that in all the drawings for describing Embodiments, the same portions or portions having the same functions are denoted by the same reference numerals, and the description thereof will not be repeated.

(Embodiment 1)

In this embodiment, a color sensor which can achieve decrease in the number of terminals for connection with the outside will be described. Note that an optical sensor to be described in this embodiment outputs a signal, which is related to the amount of incident light obtained by a photoelectric conversion element, as a current value, a voltage value, or a digital signal through a photoelectric conversion circuit portion connected to a high power supply potential Vdd and a low power supply potential Vss.

FIGS. 1A and 1B illustrate a color sensor of this embodiment. FIG. 1A is a top view of the color sensor, and FIG. 1B is a cross-sectional view of FIG. 1A along line Y-Z.

In the top view shown in FIG. 1A, the color sensor has a structure which includes an optical sensor 101R, an optical sensor 101G, and an optical sensor 101B which are mounted over an interposer. The optical sensor 101R includes a photoelectric conversion circuit portion 102R and is provided with an optical filter 103R on a surface on which light enters. The optical sensor 101G includes a photoelectric conversion circuit portion 102G and is provided with an optical filter 103G on a surface on which light enters. The optical sensor 101B includes a photoelectric conversion circuit portion 102B and is provided with an optical filter 103B on a surface on which light enters. Moreover, the interposer 100 is provided with a terminal electrode (also simply referred to as a terminal) 104, a terminal electrode 105, a terminal electrode 106, a terminal electrode 107, and a terminal electrode 108 for electrical connection with the outside on a surface for which the optical sensors 101R, 101G, and 101B are not provided (hereinafter such a surface is referred to as a back surface). Further, the interposer 100 is provided with a wiring 109, a wiring 110, a wiring 111, a wiring 112, and a wiring 113 which are conductive layers for electrically connecting the terminal electrodes 104, 105, 106, 107, and 108 to the optical sensors 101R, 101G, and 101B on a surface which is in contact with the optical sensors 101R, 101G, and 101B (hereinafter such a surface is referred to as a top surface). Furthermore, as shown by a dotted line 115, the interposer 100 has a plurality of openings which penetrate from the top surface to the back surface for electrically connecting the wirings 109 to 113 to the terminal electrodes 104 to 108.

In the cross-sectional view in FIG. 1B, the optical sensor 101R has a structure in which a light-transmitting substrate 114R is provided between the photoelectric conversion circuit portion 102R and the optical filter 103R. Moreover, the optical sensor 101G has a structure in which a light-transmitting substrate 114G is provided between the photoelectric conversion circuit portion 102G and the optical filter 103G. Further, the optical sensor 101B has a structure in which a light-transmitting substrate 114B is provided between the photoelectric conversion circuit portion 102B and the optical filter 103B. Furthermore, as shown by the dotted line 115 in FIG. 1B, the interposer 100 has a plurality of openings which penetrate from the top surface to the back surface. The optical sensors 101R, 101G, and 101B are electrically connected to the terminal electrodes 104 to 108 through the wirings 109 to 113 in the openings. Accordingly, the terminal electrodes 104 to 108 can be mounted over another substrate as external electrodes of the optical sensors 101R, 101G, and 101B. Further, it is preferable that a resin 130R, a resin 130G, and a resin 130B be provided between the interposer 100 and their respective optical sensors 101R, 101G, and 101B in order to increase bonding strength.

Note that the optical filters 103R, 103G, and 103B are each formed using a light-transmitting resin layer with a chromatic color and have light-transmitting characteristics different from each other. For example, the optical sensor 101R has an optical filter 103R which transmits red light, the optical sensor 101G has an optical filter 103G which transmits green light, and the optical sensor 101B has an optical filter 103B which transmits blue light. The optical sensors 101R, 101G, and 101B can detect lights of colors which are transmitted through their respective optical filters 103R, 103G, and 103B. Therefore, the color sensor of this embodiment including the optical filters 103R, 103G, and 103B can detect light with each of three colors (red, green, and blue).

Note that chromatic colors include colors except achromatic colors such as black, gray, and white. In order to make the optical filters 103R, 103G, and 103B function as color filters, the optical filters 103R, 103G, and 103B are formed using materials which transmit lights with chromatic colors, which are colored. As the chromatic color, red, green, blue, or the like can be used. Besides, cyan, magenta, yellow, or the like may be used.

Note that in the structure of connection portions of the optical sensors 101R, 101G, and 101B and the wiring of the interposer 100, the wiring over the interposer 100 may be made in contact with a bump which is a conductive projection provided for terminals of the optical sensors 101R, 101G, and 101B and the interposer 100 and the optical sensors 101R, 101G, and 101B may be fixed with a resin. Alternatively, a resin in which conductive particles are dispersed may be provided between the wiring of the interposer 100 and each of the terminals of the optical sensors 101R, 101G, and 101B so that the wiring of the interposer 100 and each of the optical sensors 101R, 101G, and 101B are connected to each other with the conductive particles and are bonded and fixed with an organic resin in which conductive particles are dispersed. As the resin used for bonding, a light curable resin, a thermosetting resin, a resin which is naturally cured, or the like can be used.

Note that as a material of the interposer 100, an organic polymer, an inorganic polymer, glass epoxy, ceramics, polyimide, a fluorine resin, or the like can be used.

Moreover, the thickness of the interposer 100 is approximately 50 to 300 µm (typically 100 to 200 µm). A thinner interposer can further make a color sensor slimmer.

Further, as shown in the top view in FIG. 1A and the cross-sectional view in FIG. 1B, it is preferable that the terminal electrodes 104 to 108 on the back surface of the interposer 100 do not overlap with the photoelectric conversion circuit portions 102R, 102G, and 102B on the front surface of the interposer 100. This is because, in the case where heat processing such as soldering is performed for electrically connecting the terminal electrodes 104 to 108 to an external device, generation of a defect in the photoelectric conversion circuit portions 102R, 102G, and 102B due to transfer of heat from the terminal electrodes 104, 105, 106, 107, and 108 can be suppressed. Furthermore, the wirings 109 to 113 are preferably formed over the interposer 100 so as to be apart from the photoelectric conversion circuit portion 102R, 102G, and 102B in order to promote the diffusion of heat.

Note that FIGS. 1A and 1B show the structure in which the optical filters 103R, 103G, and 103B over the top surface of the interposer 100 are provided so as to be apart from the terminal electrodes 104 to 108 on the back surface of the interposer 100. As shown in a top view in FIG. 9A and a cross-sectional view in FIG. 9B, the optical filters 103R, 103G, and 103B over the top surface of the interposer 100 may be provided so as to overlap with the terminal electrodes 104 to 108 on the back surface of the interposer 100. By employing the structure shown in FIGS. 9A and 9B, the interposer 100 can be miniaturized, resulting in the miniaturization of the color sensor. Note that by changing the width or the shape of the wirings in advance, the wirings 109 to 113 may be extended to extra areas between the wirings so that a similar effect to FIG. 22A can be obtained.

Figures 22A, 22B:
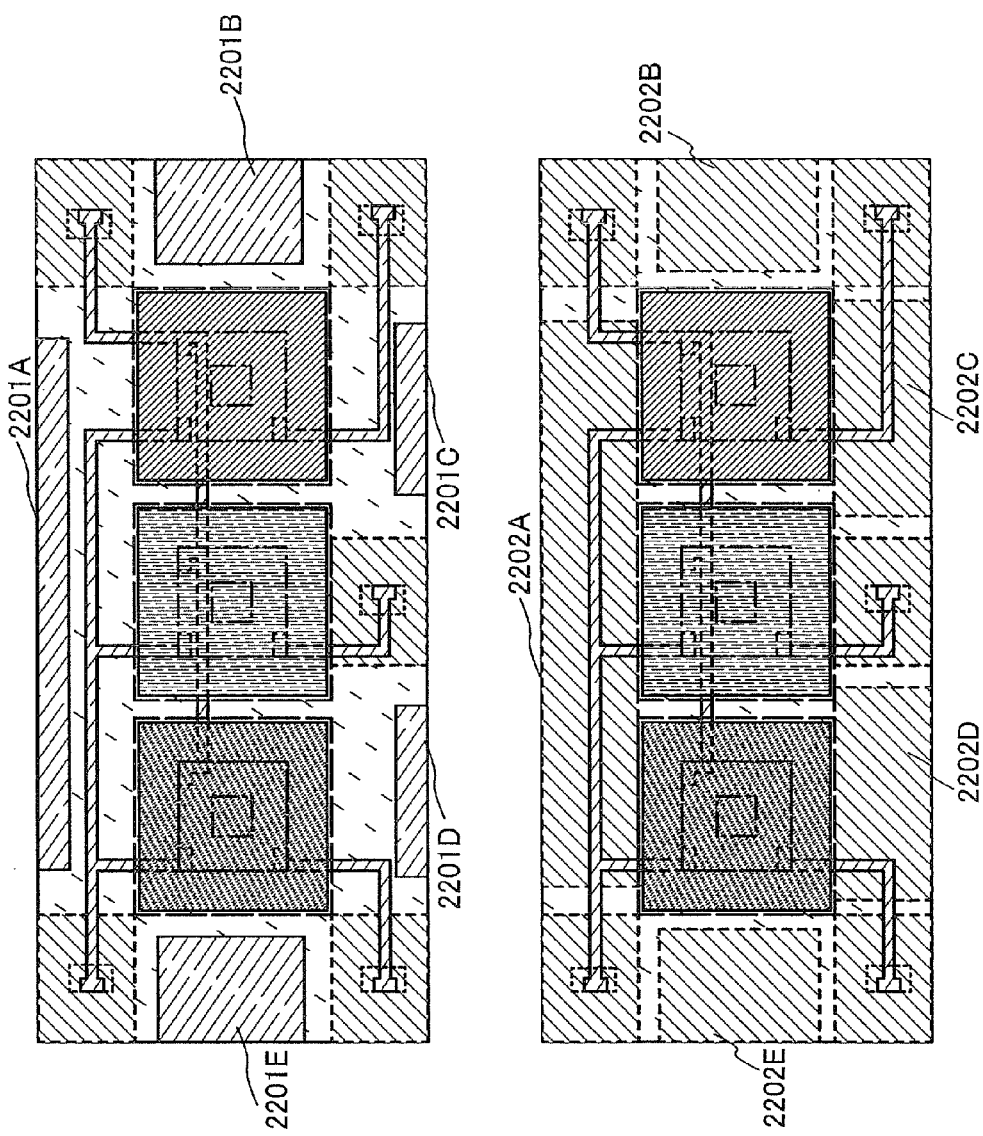
FIGS. 22A and 22B are diagrams each illustrating a color sensor.

Further, in the top view in FIG. 1A, since the optical filters 103R, 103G, and 103B are provided so as to be apart from the terminal electrodes 104 to 108, the top surface side of the interpose 100 has extra areas between the wirings for electrically connecting the terminal electrodes to the light sensors. In this embodiment, as shown in FIG. 22A, wirings 2201A to 2201E which are not electrically connected to other wirings may be provided between the wirings. By providing the wirings 2201A to 2201E, resistance to bending or the like can be increased so that a color sensor with high durability to shock can be obtained. Note that a similar effect to FIG. 22B can be obtained by changing the size or the shape of the terminal electrode in advance to provide the terminal electrodes 104 to 108 in the extra areas between the terminal electrodes; in addition, the structure shown in FIG. 22A can be combined.

Further, like FIG. 22A, the back-surface side of the interposer 100 has extra areas between the terminal electrodes. In this embodiment, as shown in FIG. 22B, electrodes 2202A to 2202E which are not electrically connected to other terminal electrodes may be provided between the terminal electrodes. By providing the electrodes 2202A to 2202E, resistance to bending or the like can be increased so that a color sensor with high durability to shock can be obtained.

Since a plurality of optical sensors mounted over the interpose 100 may be freely selected, optical sensors provided with the optical filters 103R, 103G, and 103B with chromatic colors can be mounted over the interposer 100, whereby the color sensor can be formed. In addition, since an inspection step can be performed on the optical sensors to select non-defective ones to be mounted when the optical sensors are mounted over the interposer, an yield of color sensors in the manufacturing process can be improved. Specifically, in the case of a structure in which a photoelectric conversion circuit portion includes a complicated structure such as an arithmetic calculation circuit, there is a concern that a defect is generated in an optical sensor in a chip form. Therefore, to be able to inspect defects of the optical sensors before they are mounted over the interposer is effective.

Figure 2B:
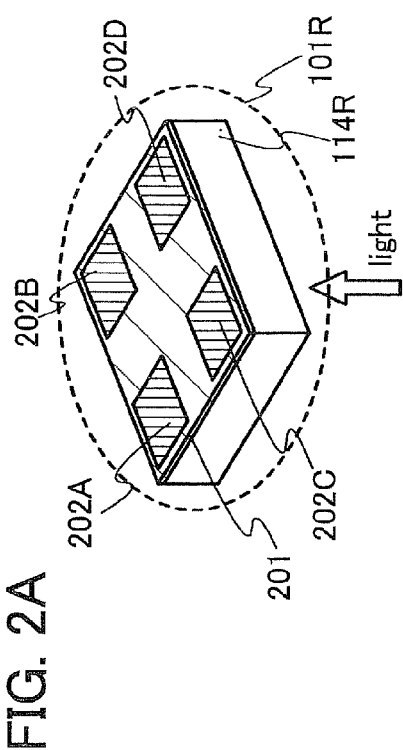

Next, with reference to FIGS. 2A to 2C, the structures of the optical sensors 101R, 101G, and 101B which are shown in FIGS. 1A and 1B will be described. Note that differences between the optical sensors 101R, 101G, and 101B are attributed to differences between light transmitting properties thereof. FIGS. 2A and 2B show the structure of the optical sensor 101R which is one of optical sensors included in the color sensor. Note that differences between the optical sensor 101R and each of the optical sensor 101G and the optical sensor 101B is attributed to a difference in the optical filter; and description thereof is omitted.

The optical sensor 101R includes a photoelectric conversion circuit portion 201 over the light-transmitting substrate 114R. The optical sensor 101R includes a first terminal 202A, a second terminal 202B, a third terminal 202C, and a fourth terminal 202D for inputting and outputting signals from/to the outside, over the photoelectric conversion circuit portion 201. Light enters the optical sensor 101R from the light-transmitting substrate 114R side and is converted into an output signal which corresponds to illuminance in the photoelectric conversion circuit portion 201.

Note that terms such as first, second, third to Nth (N is a natural number) seen in this specification are used in order to avoid confusion between components and do not set a limitation on number.

The first terminal 202A, the second terminal 202B, the third terminal 202C, and the fourth terminal 202D may be each formed using a conductive resin by a wet method or may be each formed using a conductive thin film by a dry method. Further, a conductive resin layer and a conductive thin film may be stacked.

For example, in the case of forming the terminals by a screen printing method, the terminals can be formed by selectively printing a conductive paste where a conductive particle having a particle size of several nanometers to several tens micrometers is dissolved or dispersed in an organic resin. As the conductive particle, at least one of metal particles of silver (Ag), gold (Au), copper (Cu), nickel (Ni), platinum (Pt), palladium (Pd), tantalum (Ta), molybdenum (Mo), titanium (Ti), and the like or fine particles of silver halide can be used. In addition, as the organic resin included in the conductive paste, one or more selected from organic resins functioning as a binder of metal particles, a solvent, a dispersing agent and a coating material can be used. Typically, an organic resin such as an epoxy resin, a silicone resin, and the like can be given. Further, in forming the conductive layer, it is preferable to bake the conductive paste after being provided. Alternatively, fine particles containing solder or lead-free solder as its main component may be used.

Note that FIG. 2A shows the optical sensor including four terminals: the first terminal 202A, the second terminal 202B, the third terminal 202C, and the fourth terminal 202D, for example. A high power supply potential and a low power supply potential are input to the optical sensor and an analog signal of a voltage value or a current value is output from the optical sensor. Alternatively, an optical sensor to/from which a digital signal conforming to a bus standard is input or output is also possible.

Note that although FIG. 2A shows the first terminals 202A, the second terminal 202B, the third terminal 202C, and the fourth terminal 202D which have the same shapes, the shapes may be different from each other. By making the shapes of the terminal electrodes different from each other, the direction of providing the optical sensor to the interposer can be easily figured out.

Figure 3:
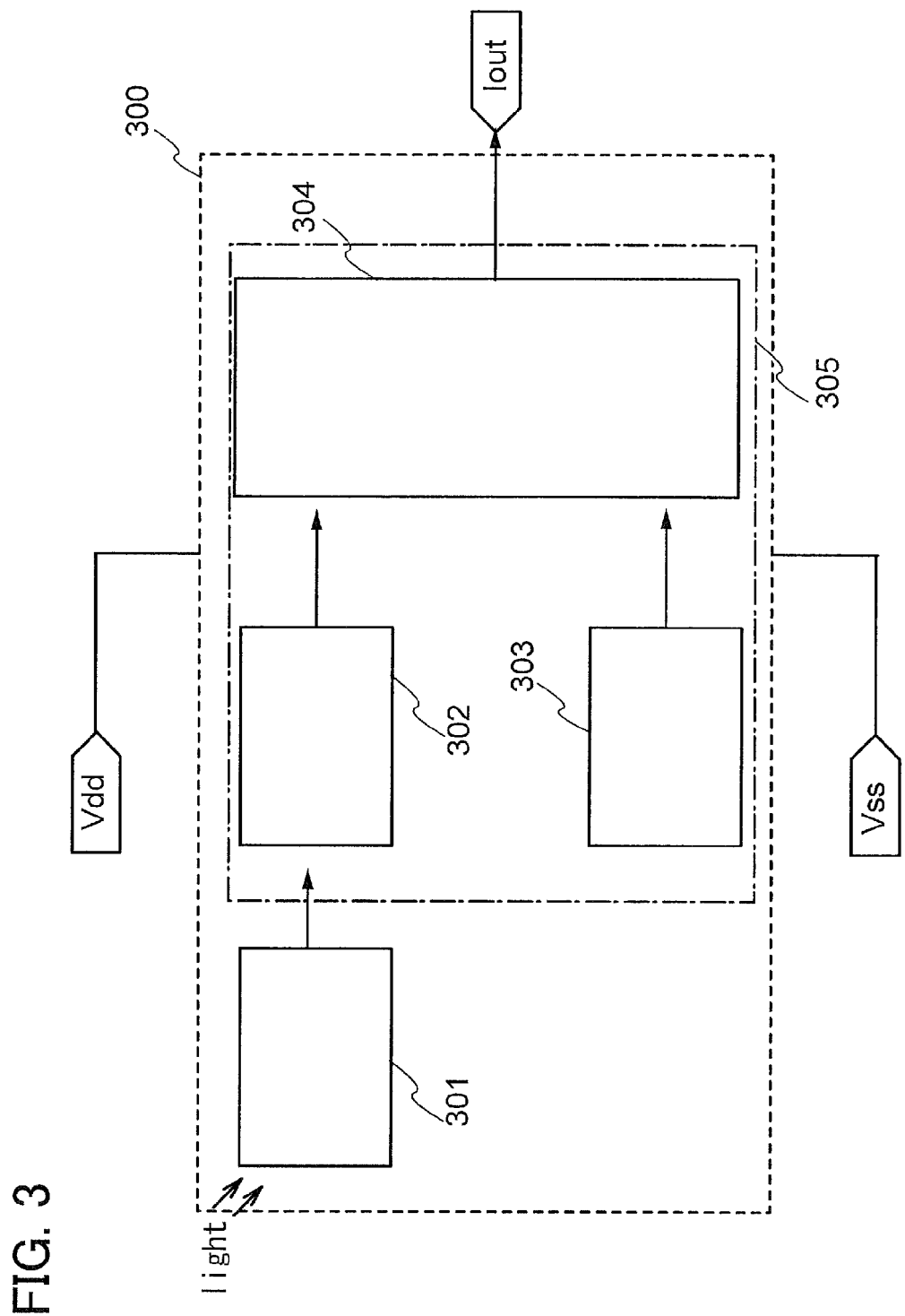
FIG. 3 is a diagram illustrating a color sensor.

Next, with reference to FIG. 3, a signal to be input and output to/from the first terminals 202A, the second terminal 202B, the third terminal 202C, and the fourth terminal 202D will be described. FIG. 3 is a block diagram which illustrates the structure of an optical sensor provided with a circuit which is supplied with a high power supply potential Vdd and a low power supply potential Vss and outputs an output signal, which has undergone logarithmic compression, corresponding to photo current. Note that the number of terminals may be three in the example in FIG. 3. Thus, the optical sensor shown in FIG. 2A has one extra terminal. In that case, the extra terminal may be a terminal which input and output the same potential or the same signal as the other terminals, or a terminal which input and output a different signal. Note that the logarithmic compression is to obtain the output value of current or voltage as a function of a logarithm by using the illuminance of light which enters the photoelectric conversion element, that is, the value of photo current.

An optical sensor 300 shown in FIG. 3 includes a photoelectric conversion element 301, a logarithmic compression circuit 302, a temperature correction voltage generation circuit 303, and a temperature correction arithmetic calculation circuit 304. The photoelectric conversion element 301 receives light from the outside and outputs photo current corresponding to illuminance to the logarithmic compression circuit 302. The logarithmic compression circuit 302 outputs the value of voltage which is obtained by performing logarithmic compression on the photo current by a diode element. The temperature correction voltage generation circuit 303 outputs a temperature correction voltage for correcting a change in output due to the temperature dependence of the diode element which is used for the logarithmic compression of the photo current. The temperature correction arithmetic calculation circuit 304 generates a current value Iout, which is an output signal, in accordance with the voltage value, which has undergone logarithmic compression, output from the logarithmic compression circuit 302 and the temperature correction voltage output from the temperature correction voltage generation circuit. Note that the photoelectric conversion circuit portion shown in FIGS. 1A and 1B corresponds to a circuit portion 305 including the logarithmic compression circuit 302, the temperature correction voltage generation circuit 303, and the temperature correction arithmetic calculation circuit 304.

Figure 4:
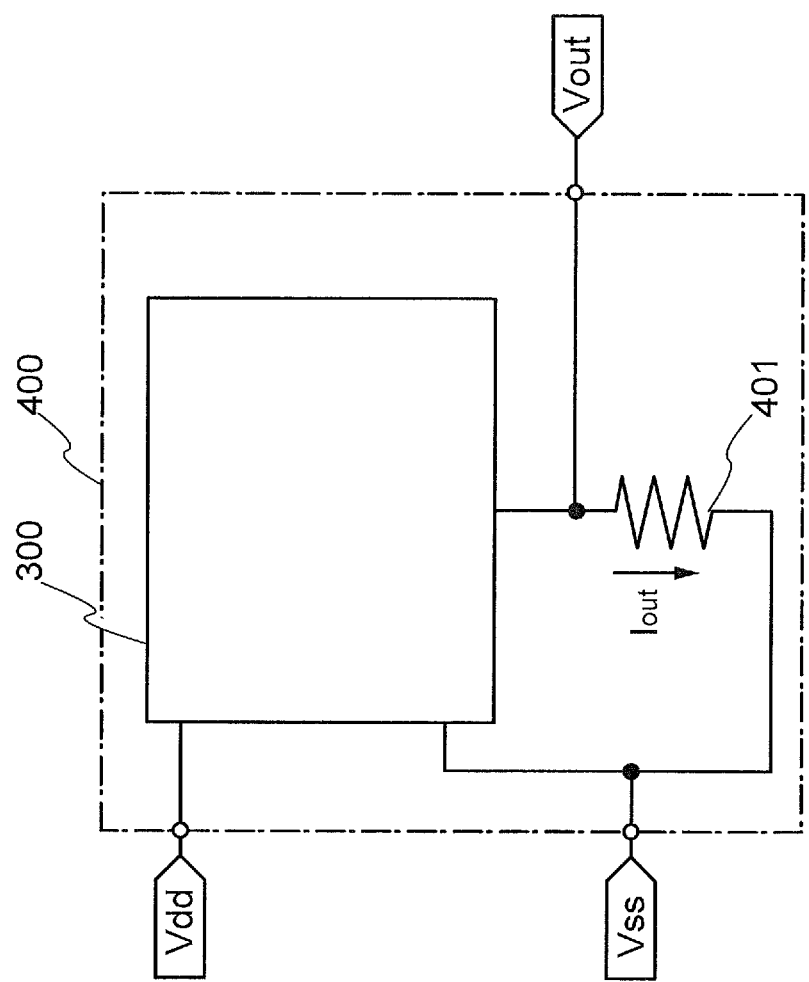
FIG. 4 is a diagram illustrating a color sensor.

Alternatively, by providing an external resistor, the optical sensor 300 which outputs an output signal as a current value Iout in FIG. 3 can also output the output signal as a voltage Vout. FIG. 4 shows an optical sensor 400 which can output the output signal as the voltage Vout. The optical sensor 400 shown in FIG. 4 is an example of a structure in which the optical sensor 300 shown in FIG. 3 is included, an internal resistor 401 is provided, and a voltage Vout is obtained as output to the outside.

Figure 5:
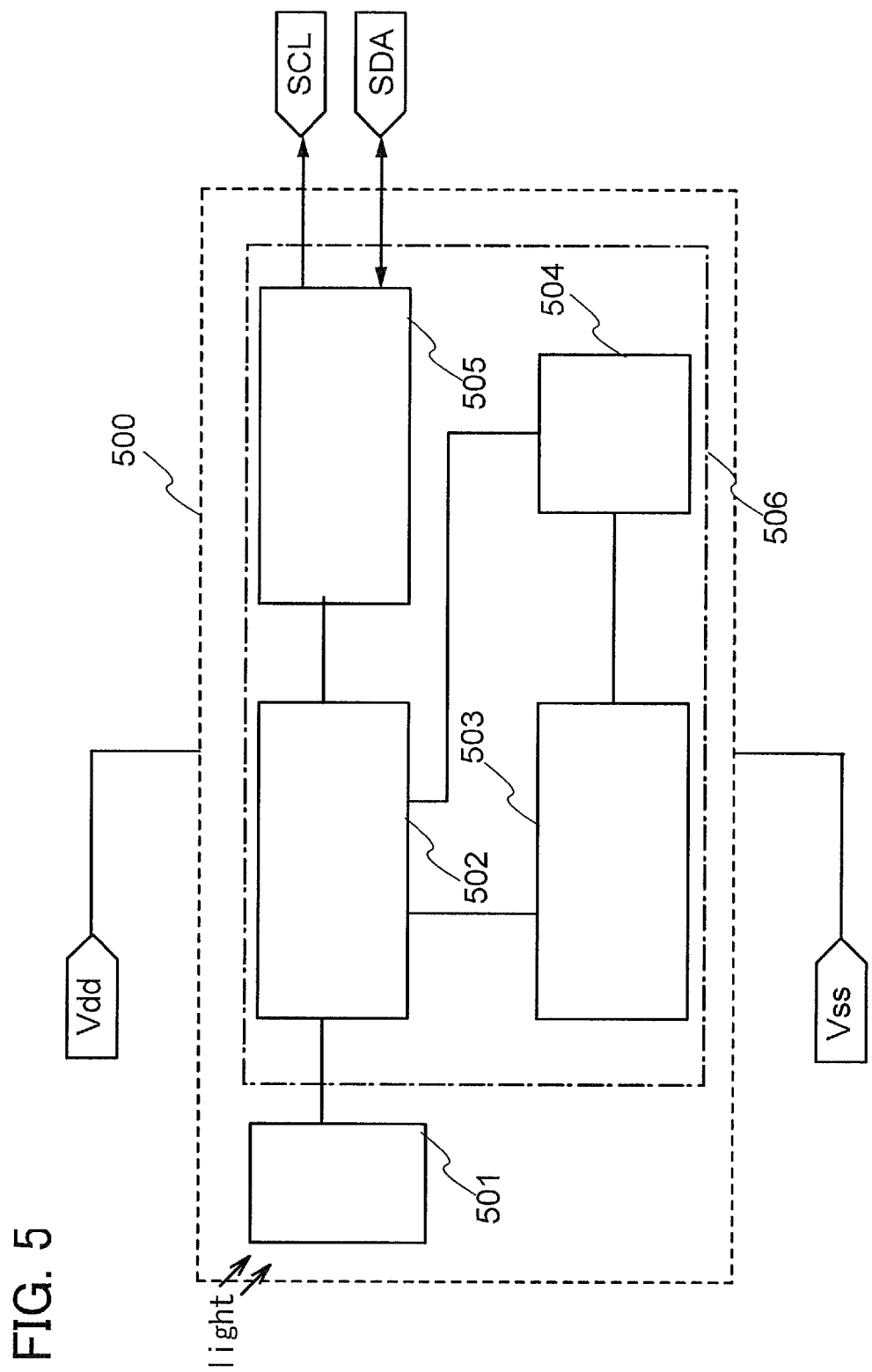
FIG. 5 is a diagram illustrating a color sensor.

Moreover, another example of a signal which is input and output to/from the first terminal 202A, the second terminal 202B, the third terminal 202C, and the fourth terminal 202D will be described. FIG. 5 is a block diagram of an optical sensor provided with a circuit which converts an analog signal to a digital signal and outputs the digital signal. Note that in the example shown in FIG. 5, two terminals for inputting and outputting output signals in addition to a high power supply potential Vdd and a low power supply potential Vss may be provided. Thus, the total number of terminals may be four. An optical sensor 500 shown in FIG. 5 includes a photoelectric conversion element 501, an analog-digital converter circuit 502 (hereinafter referred to as an AD converter circuit), a constant voltage circuit 503, an oscillator circuit 504, and an I2C (inter integrated circuit) interface circuit 505.

Note that the photoelectric conversion element 501 shown in FIG. 5 receives light from the outside and outputs photo current corresponding to illuminance to the AD converter circuit 502. The AD converter circuit 502 converts the value of the photo current to a digital signal by quantizing the value of the photo current which is continuous quantity and outputs to the I2C interface circuit 505. The constant voltage circuit 503 generates a constant voltage for operating the AD converter circuit 502 and the oscillator circuit 504. The oscillator circuit 504 outputs a clock signal for operating the AD converter circuit 502. The I2C interface circuit 505 is a circuit to be electrically connected to an external device through an I2C bus which includes a serial data line (SDA) for data communication with another device and a serial clock line (SCL) for controlling and synchronizing data communication with another device. The I2C bus that includes the SDA and the SCL is a bus standard for control from a microcomputer with the use of a unique address given to an address memory provided in each device. Note that in the case where "another device" is a liquid crystal display device, a display driver and an LED driver are electrically connected to each other through the I2C bus. Note that the photoelectric conversion circuit portions 102R, 102G, and 102B shown in FIGS. 1A and 1B each correspond to a circuit portion 506 including the AD converter circuit 502, the constant voltage circuit 503, the oscillator circuit 504, and the I2C interface circuit 505.

Note that the AD converter circuit 502 converts a voltage Vout to a digital signal by quantizing the voltage Vout which is continuous quantity. As the AD converter circuit 502, for example, a parallel-approximation-type AD converter circuit, a pipeline-type AD converter circuit, a successive-approximation-type AD converter circuit, a delta-sigma-type AD converter circuit, and a double-integrating-type AD converter circuit are given and may be selected as appropriate.

Note that although FIG. 5 shows the optical sensor 500 to which the I2C interface is applied, as well as the I2C bus, another bus standard such as a universal serial bus, a serial peripheral interface, or the like can be used.

In the case where the color sensor is formed by employing the optical sensors shown in the block diagrams in FIG. 3, FIG. 4, or FIG. 5 as the plurality of optical sensors shown in FIG. 1A, a high power supply potential Vdd and a low power supply potential Vss are input from a plurality of terminals for connection with the outside. Therefore, in order to mount the plurality of optical sensors on the interposer, electrical connection between the terminal electrode and a wiring should be achieved by leading the wiring over the interposer in accordance with the number of high power supply potentials Vdd and low power supply potentials Vss.

In the structure shown in this embodiment, as shown in FIG. 1A, since electrical connection between the terminal electrode and the wiring lead from each of the optical sensors is shared and the high power supply potential is supplied, the terminal electrodes can be shared. In FIG. 1A, a terminal which is shared between the optical sensors in order to supply the high power supply potential is the terminal electrode 104, and a wiring lead from each of the optical sensors and the terminal electrode 104 is the wiring 109. Accordingly, the wiring 109 has a plurality of branches for electrical connection between the plurality of optical sensors and the terminal electrode 104. Further, in the structure of this embodiment, as shown in FIG. 1A, since electrical connection between the terminal electrode and the wiring lead from each of the optical sensors is shared and the low power supply potential is supplied, the terminal electrodes can be shared. In FIG. 1A, a terminal which is shared between the optical sensors in order to supply the low power supply potential is the terminal electrode 105, and a wiring lead from each of the optical sensors and the terminal electrode 105 is the wiring 110. Accordingly, the wiring 110 has a plurality of branches for electrical connection between the plurality of optical sensors and the terminal electrode 105, like the wiring 109.

Note that in the case where an output signal output from each optical sensor is Iout shown in FIG. 3, the output signal can be output to the outside by providing a terminal electrode to each optical sensor and making electrical connection between the terminal electrode and a wiring by leading the wiring from each optical sensor. In FIG. 1A, a terminal which outputs an output signal from the optical sensor 101R to the outside is the terminal electrode 106, and a wiring lead from the optical sensor 101R and the terminal electrode 106 is the wiring 111. Moreover, in FIG. 1A, a terminal which outputs an output signal from the optical sensor 101G to the outside is the terminal electrode 107, and a wiring lead from the optical sensor 101G and the terminal electrode 107 is the wiring 112. Further, in FIG. 1A, a terminal which outputs an output signal from the optical sensor 101B to the outside is the terminal electrode 108, and a wiring lead from the optical sensor 101B and the terminal electrode 108 is the wiring 113.

Note that in the case where a plurality of output signals such as the serial data line and the serial clock line shown in FIG. 5 is output from each optical sensor, a terminal electrode for input/output signals of the serial data line and the serial clock line is provided to each optical sensor and electrical connection between the terminal electrode and a wiring is made by leading the wiring from each optical sensor, so that the output signals can be output to the outside.

Figure 6:
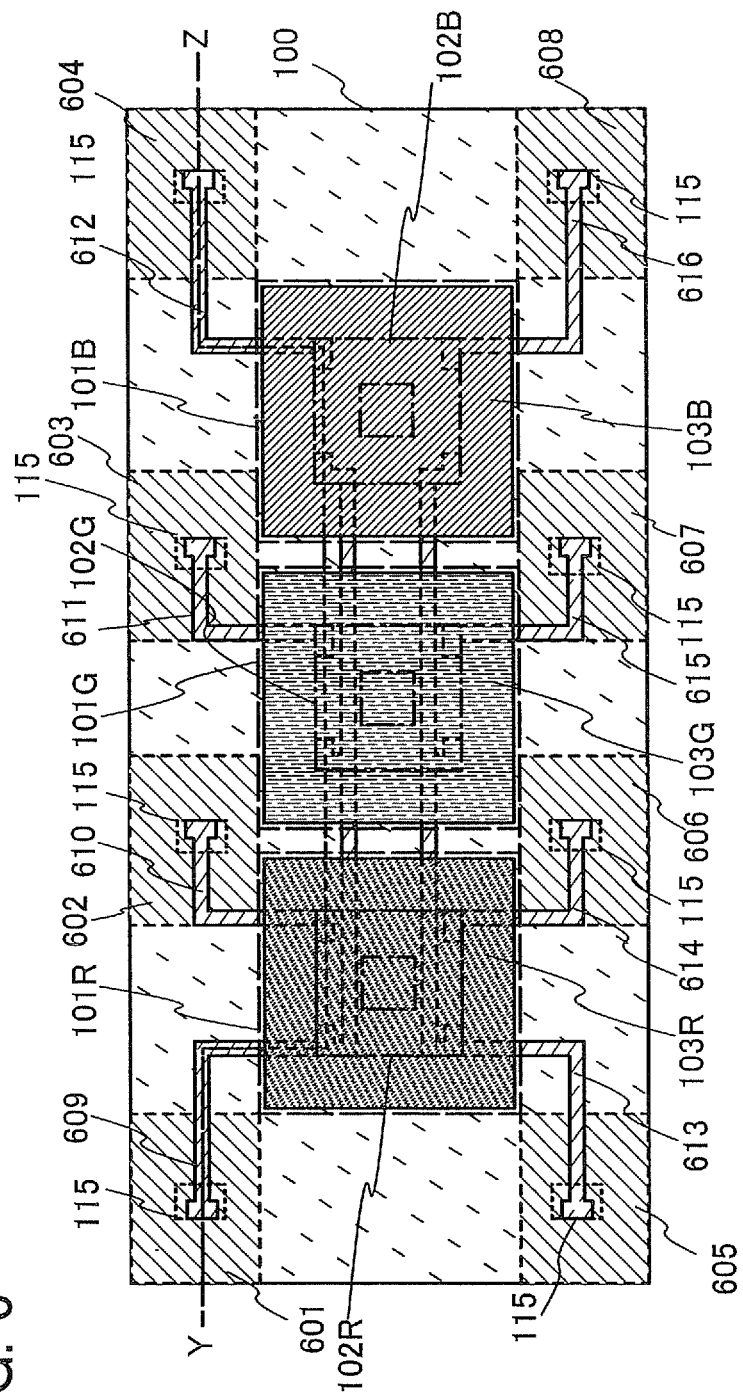
FIG. 6 is a diagram illustrating a color sensor.

FIG. 6 is a top view of a color sensor which has two input/output signals in addition to a high power supply potential Vdd and a low power supply potential Vss. Like in FIG. 1A, the color sensor includes the optical sensor 101R, the optical sensor 101G, and the optical sensor 101B mounted over the interposer 100. The optical sensor 101R includes a photoelectric conversion circuit portion 102R and is provided with an optical filter 103R on a surface on which light enters. The optical sensor 101G includes a photoelectric conversion circuit portion 102G and is provided with an optical filter 103G on a surface on which light enters. The optical sensor 101B includes a photoelectric conversion circuit portion 102B and is provided with an optical filter 103B on a surface on which light enters. Moreover, a terminal electrode 601, a terminal electrode 602, a terminal electrode 603, a terminal electrode 604, a terminal electrode 605, a terminal electrode 606, a terminal electrode 607, and a terminal electrode 608 for electrical connection with the outside are provided on the back surface of the interposer 100. Further, a wiring 609, a wiring 610, a wiring 611, a wiring 612, a wiring 613, a wiring 614, a wiring 615, and a wiring 616 which are conductive layers for electrically connecting the terminal electrodes 601 to 608 to the optical sensors 101R, 101G, and 101B are provided on the back surface of the interposer 100. Furthermore, as shown by the dotted line 115, the interposer 100 has a plurality of openings which penetrate from the top surface to the back surface for electrical connection between the wirings 609 to 616 and the terminal electrodes 601 to 608.

In FIG. 6, a terminal which is shared between optical sensors for supply of a high power supply potential is the terminal electrode 601, and a wiring which is lead from each optical sensor and the terminal electrode 601 is the wiring 609. That is, the wiring 609 has a plurality of branches in order to electrically connect a plurality of optical sensors to the terminal electrode 601. Moreover, in FIG. 6, a terminal which is shared between the optical sensors for supply of a low power supply potential is the terminal electrode 605, and a wiring which is lead from each optical sensor and the terminal electrode 605 is the wiring 613. That is, like the wiring 609, the wiring 613 has a plurality of branches in order to electrically connect the plurality of optical sensors to the terminal electrode 605. Further, in FIG. 6, a terminal which outputs a serial data line from the optical sensor 101R to the outside is the terminal electrode 602, and a wiring which is lead from the optical sensor 101R and the terminal electrode 602 is the wiring 610. Furthermore, in FIG. 6, a terminal which outputs a serial data line from the optical sensor 101G to the outside is the terminal electrode 603, and a wiring which is lead from the optical sensor 101G and the terminal electrode 603 is the wiring 611. Furthermore, in FIG. 6, a terminal which outputs a serial data line from the optical sensor 101B to the outside is the terminal electrode 604, and a wiring which is lead from the optical sensor 101B and the terminal electrode 604 is the wiring 612. Furthermore, in FIG. 6, a terminal which outputs a serial clock line from the optical sensor 101R to the outside is the terminal electrode 606, and a wiring which is lead from the optical sensor 101R and the terminal electrode 606 is the wiring 614. Furthermore, in FIG. 6, a terminal which outputs a serial clock line from the optical sensor 101G to the outside is the terminal electrode 607, and a wiring which is lead from the optical sensor 101G and the terminal electrode 607 is the wiring 615. Furthermore, in FIG. 6, a terminal which outputs a serial clock line from the optical sensor 101B to the outside is the terminal electrode 608, and a wiring which is lead from the optical sensor 101B and the terminal electrode 608 is the wiring 616.

As described above, in the color sensor provided with the plurality of optical sensors shown in FIGS. 1A and 1B and FIG. 6, the number of terminals which is increased by provision of the plurality of optical sensors shown in FIG. 3 or FIG. 5 can be reduced over the interposer. Therefore, the number of terminal electrodes can be significantly reduced. By reducing the number of terminals, a connection defect with an external device can be suppressed, so that an yield can be improved. The structure shown in this embodiment is effective for a color sensor which is formed by mounting a plurality of optical sensors provided with a terminal which is shared between the optical sensors, such as a terminal to which high power supply potentials or low power supply potentials are input. Further, the structure of this embodiment can achieve pin compatibility when the plurality of optical sensors is provided over the interposer to form the color sensor.

Note that in the top view of the color sensor shown in FIG. 6, like in FIG. 9A, the optical filters 103R, 103G, and 103B over the top surface of the interposer 100 may be provided so as to overlap with the terminal electrodes 601 to 608 on the back surface of the interposer 100.

Next, the structure of the optical sensor 101R shown in FIG. 2A will be further described in detain with reference to FIG. 2B. The optical filter 103R is provided on the side where light enters the light-transmitting substrate 114R. In addition, the side of the light-transmitting substrate 114R where the light transmitting filter 103R is provided includes a photoelectric conversion circuit 211, a wiring layer 212, and a photoelectric conversion element 213 included in the photoelectric conversion circuit portion 201. The photoelectric conversion circuit 211 includes a semiconductor layer which has electrical connection through a wiring and generates an output signal which corresponds to illuminance in the photoelectric conversion element 213. The wiring layer 212 is a wiring for electrically connecting the photoelectric conversion circuit 211, the photoelectric conversion element 213, and the first to fourth terminals 202A to 202D to each other. The photoelectric conversion element 213 converts incident light to photo current which corresponds to the amount of the light with the use of a PN photo diode, a PIN photo diode, a photo transistor, or the like. Moreover, as shown in FIG. 2B, by providing the photoelectric conversion element 213 around the center of the photoelectric conversion circuit portion, only light which passes through the optical filter can be easily received, which is preferable.

Note that in this specification, a structure in which a PIN photo diode is used as a photoelectric conversion element is described. The PIN photo diode is preferable because a depletion layer has better response characteristics to light irradiation as compared to a PN photo diode.

Figure 2C:
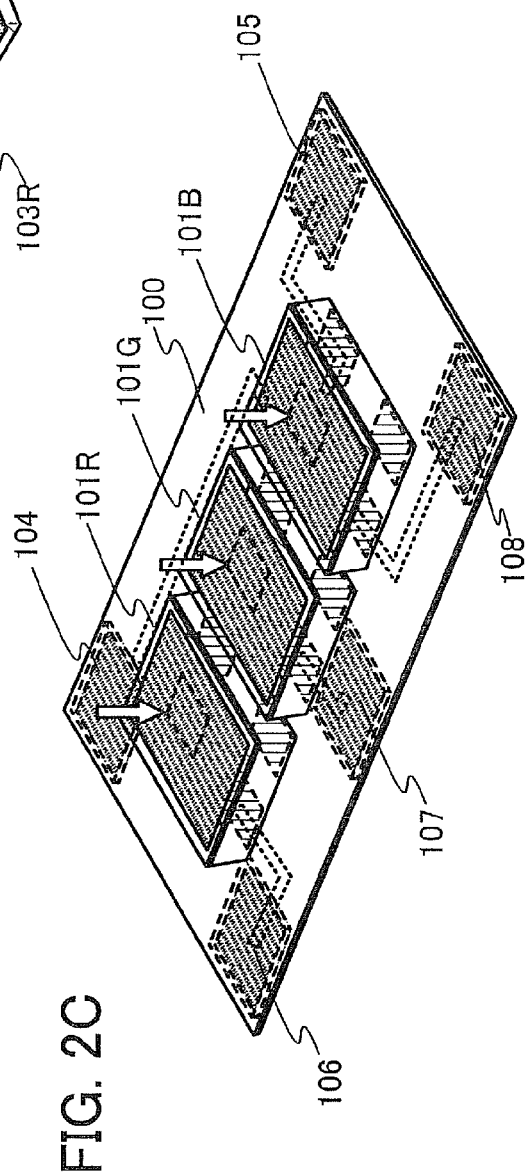

Next, as shown in FIG. 2C, the optical sensor 101R including the optical filter 103R, the optical sensor 101G including the optical filter 103G, and the optical sensor 101B including the optical filter 103B are provided over the interposer 100. Then, the optical sensors 101R, 101G, and 101B can be electrically connected to the terminal electrodes 104 to 108 through the wirings 109 to 113 (shown by a dotted line in FIG. 2C).

According to the structure shown in FIG. 2C, an inspection step can be performed on the optical sensors 101R, 101G, and 101B to select non-defective ones to be mounted when the optical sensors are mounted over the interposer 100. Therefore, the yield of color sensors can be improved. Specifically, in the case where the optical sensor includes a photoelectric conversion circuit portion which has a complicated structure such as an arithmetic calculation circuit, there is a concern that a defect is generated in an optical sensor in a chip form. Therefore, to be able to inspect defects of the optical sensors before they are mounted over the interposer 100 is effective. Further, by selecting an optical sensor with high quality from the non-defective optical sensors, and mounting the optical sensor over the interposer, a color sensor with high quality can be manufactured.

Figure 7A:
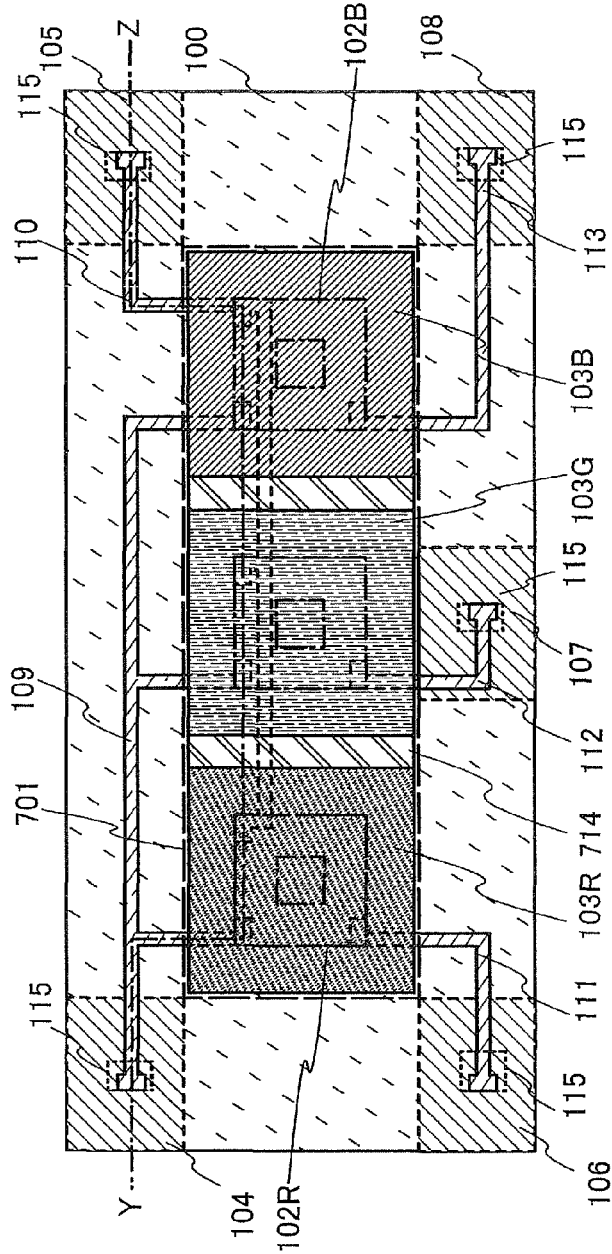
FIGS. 7A and 7B are diagrams illustrating a color sensor.
Figure 7B:
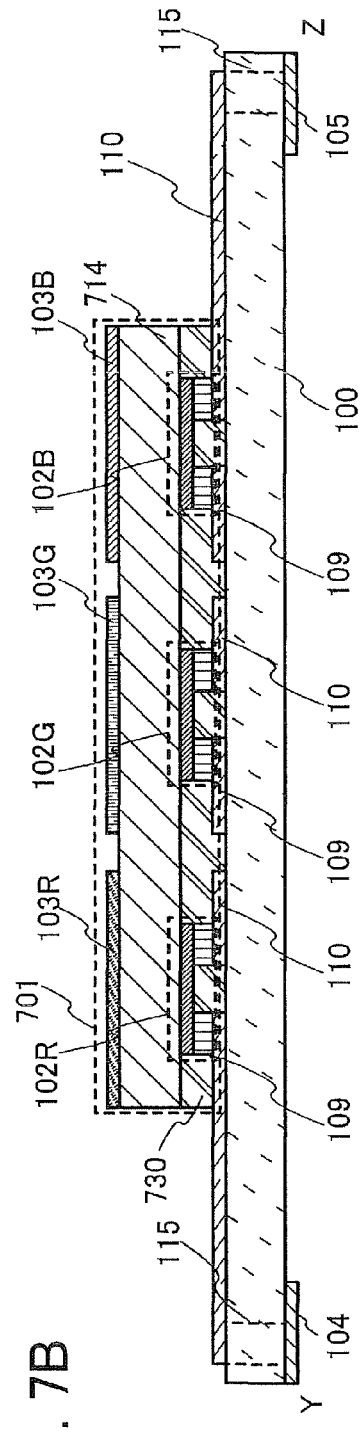

In addition, FIGS. 7A and 7B show a top view and a cross-sectional view of a color sensor which is different from that shown in FIGS. 1A and 1B. FIG. 7A is different from FIG. 1A in that an optical sensor 701 is mounted over the interposer 100 in the color sensor, the optical sensor 701 includes the photoelectric conversion circuit portions 102R, 102G, and 102B, and the optical filters 103R, 103G, and 103B on a surface where light enters. Moreover, FIG. 7A is different from FIG. 1A in that the optical filters 103R, 103G, and 103B are provided so as to be in contact with a light-transmitting substrate 714.

Note that the top view in FIG. 7A is similar to that in FIG. 1A in that the terminal electrodes 104 to 108 for electrical connection with the outside are provided on the back surface of the interposer 100. Further, the top view in FIG. 7A is similar to that in FIG. 1A in that the wirings 109 to 113 which are conductive layers for electrically connecting the terminal electrodes 104 to 108 to the optical sensor 701 are provided on the front surface of the interposer 100. Furthermore, the top view in FIG. 7A is similar to that in FIG. 1A in that, as shown by the dotted line 115, a plurality of openings which penetrates from the front surface to the back surface for electrical connection between the wirings 109 to 113 and the terminal electrodes 104 to 108 are provided in the interposer 100.

FIG. 7B is different from FIG. 1B in that the optical sensor 701 is provided with a light-transmitting substrate 714 between the photoelectric conversion circuit portions 102R, 102G, and 102B and the optical filters 103R, 103G, and 103B. Further, FIG. 7B is different from FIG. 1B in that a resin 730 for improving bonding strength is provided between the optical sensor 701 and the interposer 100 so as to fill portions between the photoelectric conversion circuit portions 102R, 102G, and 102B without no space therebetween.

Unlike FIG. 1B, by providing the resin 730 without no space in FIGS. 7A and 7B, bonding strength can be further improved, which is preferable.

Note that the cross-sectional view in FIG. 7B is similar to that in FIG. 1B in that, as shown by the dotted line 115, the interposer 100 has a plurality of openings which penetrate from the front surface to the back surface to electrically connect the optical sensors 101R, 101G, and 101B to the terminal electrodes 104 to 108 through the wirings 109 to 113.

Next, FIGS. 8A and 8B illustrate the structure of the optical sensor 701 shown in FIGS. 7A and 7B.

The optical sensor 701 includes a photoelectric conversion circuit portion 801 over the light-transmitting substrate 714. A first terminal 802A, a second terminal 802B, a third terminal 802C, and a fourth terminal 802D for inputting and outputting a signal related to light which passes through the optical filter 103R (not shown) to/from the outside are provided over the photoelectric conversion circuit portion 801. Moreover, a first terminal 803A, a second terminal 803B, a third terminal 803C, and a fourth terminal 803D for inputting and outputting a signal, which is related to light passing through the optical filter 103G (not shown), to/from the outside are provided over the photoelectric conversion circuit portion 801. Further, a first terminal 804A, a second terminal 804B, a third terminal 804C, and a fourth terminal 804D for inputting and outputting a signal, which is related to light passing through the optical filter 103B (not shown), to/from the outside are provided over the photoelectric conversion circuit portion 801. Light enters the optical sensor 701 from the light-transmitting substrate 714 side and the photoelectric conversion circuit portion 801 converts the light into an output signal which corresponds to the illuminance thereof.

Note that FIG. 8A shows an optical sensor which has 4 terminals for one optical filter, that is, the optical sensor with 12 terminals. A high power supply potential and a low power supply potential are input to the optical sensor in accordance with one optical filter. In addition, the optical sensor outputs an analog signal of a voltage value or a current value as an output signal. Alternatively, a digital signal which conforms to a bus standard is input and output to/from the optical sensor. Examples of a signal to be input and output to/from the optical sensor are as shown in FIG. 3, FIG. 4, and FIG. 5.

Next, the structure of the optical sensor 701 shown in FIG. 8A will be further described in detail with reference to FIG. 8B.

Next, FIG. 8B shows the structure in which the optical sensor 701 shown in FIG. 8A is mounted over the interposer 100. The optical sensor 701 including the optical filters 103R, 103G, and 103B is provided over the interposer 100. Then, the optical sensor 701 can be electrically connected to the terminal electrodes 104 to 108 through the wirings 109 to 113 (shown by a dotted line in FIG. 8B) shown in FIG. 7A.

According to FIG. 8B, when the optical sensor 701 is mounted over the interposer 100, the optical sensor 701 with optical filters having different light transmitting properties can be separated from a large substrate. Therefore, time for separating step can be shortened and the wear of a processing means such as a dicer used for the separation can be reduced. Further, when a selected plurality of optical sensors is mounted over the interposer, a problem of variations in the size or the height of the selected optical sensors can be solved, which is preferable.

Further, in the case where the photoelectric conversion circuit portion in the optical sensor has a complicated structure such as an arithmetic calculation circuit, and the photoelectric conversion circuit portion is shared, there is a concern that a defect is generated in an optical sensor in a chip form. Therefore, to be able to inspect defects of the optical sensors before they are mounted over the interposer 100 is effective. Further, by selecting an optical sensor with high quality from the non-defective optical sensors, and mounting the optical sensor over the interposer, a color sensor with high quality can be manufactured.

Next, embodiments of a cross-sectional view of a color sensor, which are different from that described in FIG. 1B will be described with reference to FIGS. 10A to 10C and FIGS. 11A to 11C.

The cross-sectional view in FIG. 10A shows an example in which a light-shielding layer 116 is formed so as to cover the optical filters 103R, 103G, and 103B which correspond to regions where the photoelectric conversion elements of the optical sensors 101R, 101G, and 101B shown in the cross-sectional view in FIG. 1B while opening portions are not partly covered with the light-shielding layer 116. Note that the light-shielding layer 116 can be formed by an applying method such as a spin coating method. Alternatively, the light-shielding layer 116 can be formed by a droplet discharging method, a printing method, a dipping method, a dispenser method, a brush coating method, a spraying method, a flow coating method, or the like.

The light-shielding layer 116 can shield light in order to prevent malfunction of the photoelectric conversion elements included in the optical sensors 101R, 101G, and 101B due to inappropriate light irradiation from the outside. Therefore, since the photoelectric conversion elements can receive only light which has entered from the openings of the light-shielding layer 116 and passed through the optical filters 103R, 103G, and 103B which function as optical filters with chromatic colors, the reliability of the color sensor is increased. Further, although there is a concern of variations in characteristics when the semiconductor elements of the photoelectric conversion circuit portions 102R, 102G, and 102B are irradiated with light, such defects can be prevented by providing the light-shielding layer.

Further, the cross-sectional view of a color sensor in FIG. 10B shows an example in which the optical filters 103R, 103G, and 103B are formed so as to correspond to the regions where the photoelectric conversion elements of the optical sensors 101R, 101G, and 101B shown in the cross-sectional view in FIG. 10A, and the light-shielding layer 116 is formed so as to cover the optical filters 103R, 103G, and 103B while the opening portions are not partly covered with the light-shielding layer 116.

Since the optical filters 103R, 103G, and 103B are provided so as to correspond to the regions where the photoelectric conversion elements of the optical sensors 101R, 101G, and 101B are formed, the areas of the optical filters can be small. Accordingly, a light-transmitting resin which is a material of the optical filters 103R, 1036, and 103B can be reduced, whereby cost can be reduced. In addition, light can be blocked so that the photoelectric conversion elements included in the optical sensors 101R, 101G, and 101B are prevented from being irradiated with inappropriate light from the outside and causing malfunction. Therefore, since the photoelectric conversion elements can receive only light which has entered from the openings of the light-shielding layer 116 and passed through the optical filters 103R, 103G, and 103B which function as optical filters with chromatic colors, the reliability of the color sensor is increased. Further, although there is a concern of variations in characteristics when semiconductor elements of the photoelectric conversion circuit portions 102R, 102G, and 102B are irradiated with light, such defects can be prevented by providing the light-shielding layer.

The cross-sectional view of a color sensor in FIG. 10C shows an example in which the light-shielding layer 116 whose opening portions are formed so as to correspond to the regions where the photoelectric conversion elements of the optical sensors 101R, 101G, and 101B are provided shown in the cross-sectional view in FIG. 10A is formed, and then the optical filters 103R, 103G, and 103B are formed.

As in FIG. 10B, since the optical filters 103R, 103G, and 103B can be provided so as to correspond to the regions where the photoelectric conversion elements of the optical sensors 101R, 101G, and 101B are formed, the areas of the optical filters can be made to be small. Accordingly, a light-transmitting resin which is a material of the optical filters 103R, 103G, and 103B can be reduced, whereby cost can be reduced. In addition, light can be blocked so that the photoelectric conversion elements included in the optical sensors 101R, 101G, and 101B are prevented from being irradiated with inappropriate light from the outside and causing malfunction. Therefore, since the photoelectric conversion elements can receive only light which has passed through the optical filters 103R, 103G, and 103B which function as optical filters with chromatic colors and enters from the openings of the light-shielding layer 116, the reliability of the color sensor is increased. Further, although there is a concern of variations in characteristics when the semiconductor elements of the photoelectric conversion circuit portions 102R, 102G, and 102B are irradiated with light, such defects can be prevented by providing the light-shielding layer.

In the structures shown in FIGS. 10A to 10C, side surfaces of the light-transmitting substrates which are in contact with the optical filters of the optical sensors 101R, 101G, and 101B may be curved surfaces which spread toward the bottom.

A cross-sectional view of a color sensor shown in FIG. 11A is an example in which side surfaces of light-transmitting substrates 114R, 114G, and 114B which are in contact with the optical filters of the optical sensor 101R, 101G, and 101B have curved surfaces which spread toward the bottom.

As shown in FIG. 11A, since top portions of the optical sensors 101R, 101G, and 101B can be covered with the optical filters 103R, 103G, and 103B, inappropriate light can be blocked so that the photoelectric conversion elements are prevented from being irradiated with the inappropriate light from the outside and causing malfunction. Therefore, since the photoelectric conversion element can receive only light which has passed through the optical filters 103R, 103G, and 103B which function as optical filters with chromatic colors and entered from the openings of the light-shielding layer 116, the reliability of the color sensor is increased. Further, although there is a concern of variations in characteristics when the semiconductor elements of the photoelectric conversion circuit portions 102R, 102G, and 102B are irradiated with light, such defects can be prevented by providing the light-shielding layer.

A cross-sectional view of a color sensor shown in FIG. 11B is an example in which side surfaces of the light-transmitting substrates 114R, 114G, and 114B which are in contact with the optical filters of the optical sensor 101R, 101G, and 101B have curved surfaces which spread toward the bottom, and the optical filters are covered with light-transmitting resin layers 117R, 117G, and 117B.

As shown in FIG. 11B, since top portions of the optical sensors 101R, 101G, and 101B can be covered with the optical filters 103R, 103G, and 103B, inappropriate light can be blocked so that the photoelectric conversion elements included in the optical sensors 101R, 101G, and 101B are prevented from being irradiated with the inappropriate light from the outside and causing malfunction. Therefore, since the photoelectric conversion element can receive only light which has passed through the optical filters 103R, 103G, and 103B which function as optical filters with chromatic colors and entered from the opening of the light-shielding layer 116, the reliability of the color sensor is increased. Further, although there is a concern of variations in characteristics when semiconductor elements of the photoelectric conversion circuit portions 102R, 102G, and 102B are irradiated with light, such defects can be prevented by providing the light-shielding layer. Furthermore, by providing the light-transmitting resin layers 117R, 117G, and 117B, the light-transmitting resin layers 117R, 117G, and 117B can function as protective layers, shock absorption is increased, and deterioration of the light-transmitting resin layers with chromatic colors can be prevented. Furthermore, the light-transmitting resin layers which function as the shock absorption layers may be thicker than the optical filters 103R, 103G, and 103B. Accordingly, the light-transmitting resin layer that functions as each shock absorption layer can be thick, whereby shock resistance as the shock absorption layer can be increased.

In addition, a cross-sectional view of a color sensor in FIG. 11C is an example in which the optical filters of the optical sensors 101R, 101G, and 101B are provided on and in contact with curved side surfaces, which spread toward the bottom, of the light-transmitting substrates 114R, 114G, and 114B; the light-shielding layers 116R, 116G, and 116B having opening portions which correspond to regions where the photoelectric conversion elements of the optical sensors 101R, 101G, and 101B are provided is formed over the optical filters, and the light-transmitting resin layers 117R, 117G, and 117B cover the light-shielding layers and the optical filters.

As shown in FIG. 11C, since top portions of the optical sensors 101R, 101G, and 101B can be covered with the optical filters 103R, 103G, and 103B and the light-shielding layers can be provided in the regions where the photoelectric conversion elements are provided, inappropriate light can be blocked so that the photoelectric conversion elements included in the optical sensors 101R, 101G, and 101B are prevented from being irradiated with the inappropriate light from the outside and causing malfunction. Therefore, since the photoelectric conversion element can receive only light which has passed through the optical filters 103R, 103G, and 103B which function as optical filters with chromatic colors and entered from the opening of the light-shielding layer 116, the reliability of the color sensor is increased. Further, although there is a concern of variations in characteristics when the semiconductor elements of the photoelectric conversion circuit portions 102R, 102G, and 102B are irradiated with light, such defects can be prevented by providing the light-shielding layer. Furthermore, by providing the light-transmitting resin layers 117R, 117G, and 117B, the light-transmitting resin layers 117R, 117G, and 117B can function as protective layers, shock absorption is increased, and deterioration of the light-transmitting resin layers with chromatic colors can be prevented. Furthermore, the light-transmitting resin layers which function as shock absorption layers may be thicker than the optical filters 103R, 103G, and 103B. Accordingly, the light-transmitting resin layer that functions as each shock absorption layer can be thick, whereby shock resistance as the shock absorption layer can be increased.

As described above, in the color sensor of this embodiment, the number of terminal electrodes which increases by the provision of a plurality of optical sensors can be reduced over the interposer. Specifically, terminal electrodes to which high power supply potentials are input can be made to be a common terminal electrode over the interposer, and terminal electrodes to which low power supply potentials are input can be made to be a common terminal electrode over the interposer. Accordingly, the number of terminal electrodes can be significantly reduced. By reducing the number of terminal electrodes, suppression of a defect of connection with an external device can be achieved, whereby an yield can be improved. Further, the structure of this embodiment can achieve pin compatibility when the plurality of optical sensors is provided over the interposer to form the color sensor.

Note that the contents described in each drawing in this embodiment can be freely combined with or replaced with the contents described in another embodiment mode as appropriate.

(Embodiment Mode 2)

In this embodiment, one example of a method for manufacturing the optical sensor described in Embodiment 1 will be shown and described. In this embodiment, for example, the method for manufacturing the optical sensor described in the cross-sectional view in FIG. 11B of Embodiment 1 will be described.

Figure 12A:
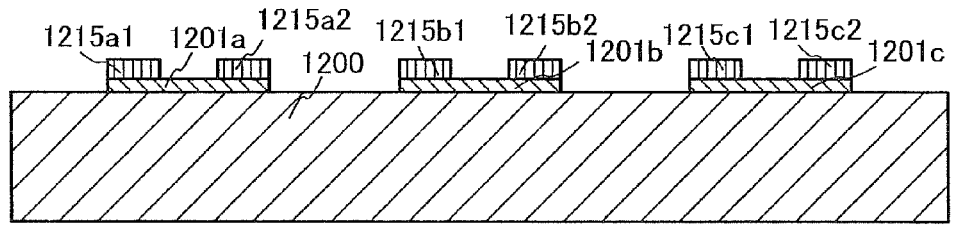
FIGS. 12A to 12F are diagrams illustrating transistors included in a color sensor.

FIG. 12A illustrates a plurality of photoelectric conversion circuit portions (hereinafter referred to as semiconductor element layers 1201a, 1201b, and 1201c) each including a photoelectric conversion element layer, which are provided over a light-transmitting substrate 1200. The semiconductor element layer 1201a includes terminal electrodes 1215a1 and 1215a2, the semiconductor element layer 1201b includes terminal electrodes 1215b1 and 1215b2, and the semiconductor element layer 1201c includes terminal electrodes 1215c1 and 1215c2.

Figure 12B:
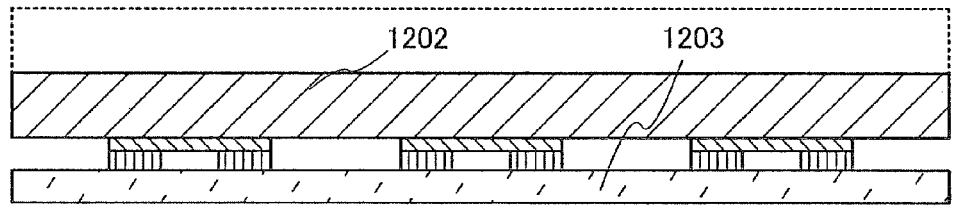

Next, a step of reducing the thickness of the light-transmitting substrate 1200 by grinding treatment and/or polishing treatment is performed. The side on which the semiconductor element layers 1201a, 1201b, and 1201c are formed is made to face a fixing tape 1203 for fixing the light-transmitting substrate 1200 in the step, the light-transmitting substrate 1200 is fixed, and the light-transmitting substrate 1200 is processed into a light-transmitting substrate 1202 which is thin (see FIG. 12B). In the case where the light-transmitting substrate 1200 is a glass substrate with a thickness of 0.5 mm, the light-transmitting substrate 1202 is preferably thinned to approximately 0.25 to 0.3 mm. By reducing the thickness of the light-transmitting substrate, the process time for dividing the light-transmitting substrate can be reduced, and wear of a processing means such as a dicer used for the division can be reduced. Grinding treatment and polishing treatment can be preferably used in combination. In this embodiment, a substrate is ground by a grinder and after that, a surface is flattened with polishing treatment by a polisher. As the polishing treatment, chemical mechanical polishing may be performed.

Figure 12C:
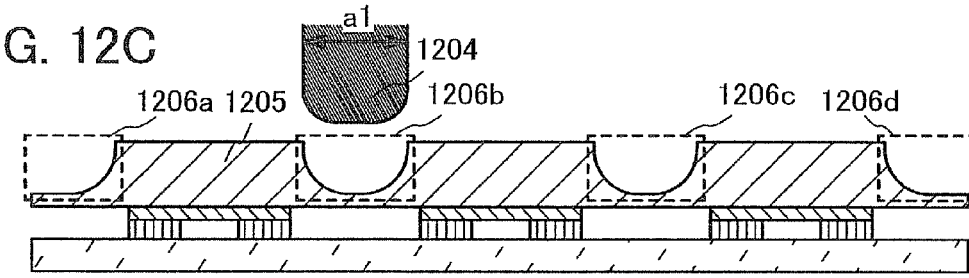

In this embodiment, an example in which a plurality of optical sensors in a chip form is obtained by dividing a light-transmitting substrate with large area is shown. A separation step is not performed at one time. First, grooves 1206a, 1206b, 1206c, and 1206d for dividing the semiconductor element layers 1201a, 1201b, and 1201c are formed in the light-transmitting substrate 1202 by a dicing blade of a dicer 1204 (see FIG. 12C). When forming the grooves 1206a, 1206b, and 1206c in the light-transmitting substrate 1205, light-transmitting substrate 1205 are intentionally left to some degree. The thickness of the light-transmitting substrate 1205 to be left may be approximately 30 to 100 μm (preferably 30 to 50 μm).

Figure 12D:
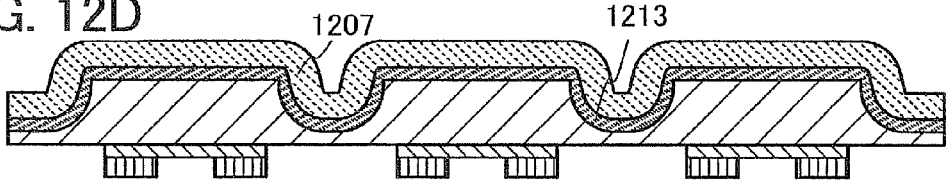

Next, a stack of a light-transmitting resin layer 1213 and a light-transmitting resin layer 1207 is formed over the light-transmitting substrate 1202 in which the grooves 1206a, 1206b, 1206c, and 1206d are formed (see FIG. 12D). In the case where heat treatment is performed in the process after the light-transmitting resin layer is formed (e.g., in mounting the interposer), a resin material which can resist to the heating temperature is used as the material for the light-transmitting resin layers 1213 and 1207. One of the stacked light-transmitting resin layers is a colored layer with a chromatic color which functions as an optical filter, and the other is a resin layer which functions as a shock absorption layer. In this embodiment, the light-transmitting resin layer 1213 is formed using a resin layer containing a colored material with a chromatic color.

Forming the light-transmitting resin layer 1207 which functions as a shock absorption layer can give an optical sensor and a color sensor higher stress resistance. For example, the optical sensor provided with the light-transmitting resin layer described in this embodiment can resist a pressure of approximately 20 N without breaking.

For the light-transmitting resin layer, a resin material such as a vinyl resin, an epoxy resin, a phenol resin, a novolac resin, an acrylic resin, a melamine resin, an urethane resin, or a siloxane resin can be used. As the method for forming the resin layer, an application method such as a spin coating method can be used. Alternatively, a droplet discharging method, a printing method, a dipping method, a dispenser method, a brush coating method, a spraying method, a flow coating method, or the like can be used.

Figure 12E:
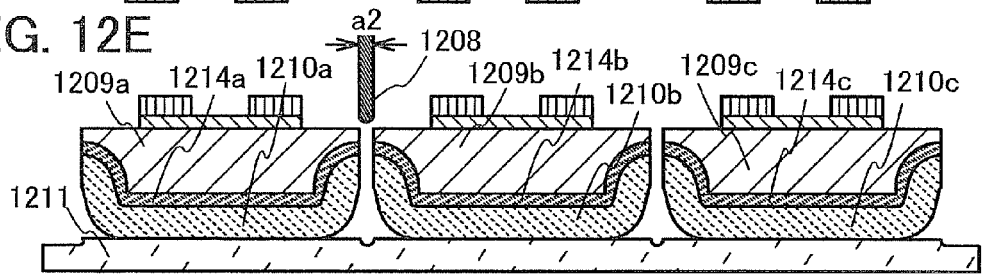

After that, the light-transmitting resin layers 1213 and 1207 and the light-transmitting substrate 1205 are divided (separated) so as to provide a plurality of optical sensors by cutting the light-transmitting resin layers 1213 and 1207 and the light-transmitting substrate 1205 at the grooves 1206a, 1206b, 1206c, and 1206d. In this embodiment, the light-transmitting substrate 1205 and the light-transmitting resin layers 1213 and 1207 are fixed on a fixing tape 1211, and a dicer 1208 cuts the light-transmitting substrate 1205 and the light-transmitting resin layers 1213 and 1207, which have been left in the grooves 1206a, 1206b, 1206c, and 1206d, from the light-transmitting substrate 1205 side. By the dicer 1208, the light-transmitting substrate 1205 and the light-transmitting resin layers 1213 and 1207 are divided to form light-transmitting substrates 1209a, 1209b, and 1209c, and light-transmitting resin layers 1214a, 1214b, 1214c, 1210a, 1210b, and 1210c (see FIG. 12E). In this embodiment, a dicing tape is used as the fixing tapes 1203 and 1211.

When the light transmitting substrate 1205 in which the grooves are formed and the light transmitting resin layers 1213 and 1207 are cut, they can be cut from the light transmitting substrate 1205 side or the light transmitting resin layers 1213 and 1207 side. In the case where an alignment marker is formed on the light-transmitting substrate 1205, precision of a place to be cut can be improved when the light-transmitting substrate 1205 and the light-transmitting resin layers 1213 and 1207 are cut from the light-transmitting substrate 1205 side by a cutting means such as a dicer.

Figure 12F:
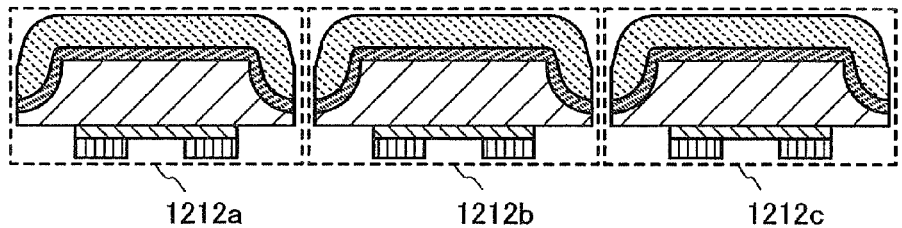

Through the above steps, optical sensors 1212a, 1212b, and 1212c can be formed (see FIG. 12F). The width a1 of a cut surface where the light-transmitting resin layers 1207 and the light-transmitting substrate 1202 are cut is made smaller than the width of the groove, whereby the resin layer formed in the groove can be left on side surfaces of the light-transmitting substrate. In this embodiment, the width of the dicer 1204 and the width of the dicer 1208 each correspond to the thickness of a dicing blade by which a region to be processed (by the dicer) is determined.

The width of the cut surface can be controlled by the width a1 of the dicing blade of the dicer 1204, and the width of the groove can be controlled by the width a2 of the dicing blade of the dicer 1208. Accordingly, the width a2 of the dicing blade of the dicer 1208 may be made narrower than the width a1 of the dicing blade of the dicer 1204. In this embodiment, the width a1 of the dicing blade of the dicer 1204 is 0.16 mm and the width a2 of the dicing blade of the dicer 1208 is 0.1 mm.

Accordingly, parts of surfaces and side surfaces, which are not provided with the semiconductor element layers 1201a, 1201b, and 1201c, of the optical sensors 1212a, 1212b, and 1212c are covered with the resin layers 1210a, 1210b, and 1210c.

The shape of the groove formed in the light-transmitting substrate depends on a processing means. In this embodiment, since the shape of the dicing blade of the dicer 1204 is slightly rounded, the grooves 1206a, 1206b, 1206c, and 1206d also have rounded shapes (shapes with curvature) in the cross section in FIG. 11B. When the shape of the dicing blade is rectangular, the shape of the groove is also rectangular, whereby an end portion of the light-transmitting substrate in the optical sensor after the division can also have a rectangular shape.

In order to improve the coverage of the end portions of the substrate, the light-transmitting resin layer is preferably thicker. The shape of an optical sensor to be completed can be freely changed depending on the structure, the thickness, or the cut position of the light-transmitting resin layer.

Division with a dicer with a thin dicing blade may leave a large groove region of the light-transmitting substrate in the completed optical sensor. By stacking a light-transmitting resin layer which functions as a shock absorber, an optical sensor can further withstand stress.

Further, in this embodiment, since a groove is formed and a light-transmitting resin layer is formed over the groove, the light-transmitting resin layer can be formed to be thick on the bottom surface of the groove. Further, after the light-transmitting resin layer is formed, the stack of the light-transmitting resin layer and the light-transmitting substrate is cut; therefore, the end portions of the light-transmitting resin layer are aligned with those of the light-transmitting substrate in the side surfaces. The upper end portions of the light-transmitting substrate are not exposed in the side surfaces; therefore, the end portions of the light transmitting substrate can be prevented from being damaged or getting chipped. Further, when the light-transmitting resin layer is formed thick with stacked layers, the damage to the end portion of the light-transmitting substrate can be reduced because the distance between the end portion of the light-transmitting substrate and the end portion of the light-transmitting resin layer can be long on the side surface of the optical sensor.

As shown in FIGS. 12A to 12F, the color sensor can be formed by mounting the plurality of optical sensors, which is formed over respective substrates and divided, over the interposer.

The light-transmitting substrate which is formed to be thin is covered with a light-transmitting resin layer, so that it is easily treated in a process, and defects such as breakage hardly occur. Accordingly, a thinner and higher-performance color sensor can be manufactured with high yield.

Since the plurality of optical sensors to be mounted over the interposer can be selected as appropriate, optical sensors with light-transmitting resins with different chromatic colors can be mounted over the interposer, so that form a color sensor can be formed.

Further, an optical sensor is subjected to an inspection step before being mounted over an interposer, so that only a conforming item can be selected and mounted over the interposer. Thus, yield of a color sensor is increased in a manufacturing process. Particularly in the case of a structure in which the optical sensor includes a semiconductor element layer including a complicated structure such as an amplifier circuit, since there is a possibility to generate defects in the optical sensor in a chip form, it is effective if the optical sensor can be inspected for defects before the optical sensor is mounted over the interposer.

Further, an optical sensor in this embodiment has a structure in which a chromatic color light transmitting resin layer covers at least a surface of a light-transmitting substrate which is opposite to a surface on which a semiconductor element layer is formed and a part of the end portion (side surface) of the light-transmitting substrate. Thus, the light-transmitting resin layer also functions as a shock absorption layer which absorbs external stress such as pressure which is applied in the manufacturing step or in the inspection step, so that defects such as a scratch and a crack of an optical sensor can be reduced, and a color sensor with high reliability can be manufactured.

A method for forming a photoelectric conversion element and a field effect transistor over a substrate as semiconductor element layers to be divided is described with reference to FIGS. 13A to 13D, FIGS. 14A to 14C, and FIGS. 15A and 15B, which are cross-sectional views of an element.

AN 100 which is one of glass substrates is used as a light-transmitting substrate 1310. A thin film transistor is used as a field effect transistor formed over the substrate so that a photoelectric conversion element and a thin film transistor can be formed on the substrate in the same step; therefore, there is an advantage that the photoelectric conversion element is easy to be produced in large quantities. Note that in the optical sensor described in this embodiment, a photoelectric conversion element is irradiated with light which has passed through a light-transmitting resin layer and a light-transmitting substrate serving as an optical filter (hereinafter referred to as a color filter).

Next, a silicon oxide film containing nitrogen is deposited as a base insulating film 1312 (a thickness of 100 nm) by a plasma CVD method. Then, without exposing the base insulating film 1312 to air, a semiconductor film, e.g., an amorphous silicon film containing hydrogen (a thickness of 54 nm) is stacked thereover. In addition, a silicon oxide film, a silicon nitride film, and a silicon oxide film containing nitrogen may be stacked to form the base insulating film 1312. For example, a silicon nitride film containing oxygen of 50 nm thick, and further, a silicon oxide film containing nitrogen of 100 nm thick may be stacked to form the base insulating film 1312. The silicon oxide film containing nitrogen or the silicon nitride film serves as a blocking layer which prevents an impurity such as an alkali metal from diffusing from a glass substrate.

The semiconductor layer in a semiconductor element can be formed using the following material: an amorphous semiconductor (hereinafter also referred to as an AS) manufactured by a vapor-phase growth method using a semiconductor material gas typified by silane or germane or a sputtering method; a polycrystalline semiconductor formed by crystallizing the amorphous semiconductor by utilizing light energy or thermal energy; a microcrystalline (also referred to as semiamorphous or microcrystal) semiconductor (hereinafter also referred to as a "SAS"); or the like. The semiconductor layer can be formed by a sputtering method, an LPCVD method, a plasma CVD method, or the like.

The microcrystalline semiconductor film belongs to a metastable state which is intermediate between an amorphous state and a single crystal state when Gibbs free energy is considered. That is, the microcrystalline semiconductor film is a semiconductor having a third state which is stable in terms of free energy and has a short range order and lattice distortion. Columnar-like or needle-like crystals grow in a normal direction with respect to a substrate surface. The Raman spectrum of microcrystalline silicon, which is a typical example of a microcrystalline semiconductor, shifts to the lower wavenumber side than 520 $cm^{-1}$ which represents single crystal silicon. That is, the peak of the Raman spectrum of the microcrystalline silicon exists between 520 $cm^{-1}$ which represents single-crystalline silicon and 480 $cm^{-1}$ which represents amorphous silicon. The semiconductor includes hydrogen or halogen of at least 1 at. % to terminate a dangling bond. Moreover, a rare gas element such as helium, argon, krypton, or neon may be included to further promote lattice distortion, so that stability is enhanced and a favorable microcrystalline semiconductor film can be obtained.

The microcrystalline semiconductor film can be formed by a high-frequency plasma CVD method with a frequency of several tens to several hundreds of megahertz or a microwave plasma CVD apparatus with a frequency of 1 GHz or more. The microcrystalline semiconductor film can be typically formed using a dilution of silicon hydride such as $SiH_4$, $Si_2H_6$, $SiH_2Cl_2$, $SiHCl_3$, $SiCl_4$, or $SiF_4$ with hydrogen. With dilution with one or plural kinds of rare gas elements selected from helium, argon, krypton, and neon in addition to silicon hydride and hydrogen, the microcrystalline semiconductor film can be formed. In that case, the flow rate ratio of hydrogen to silicon hydride is set to be 5:1 to 200:1, preferably, 50:1 to 150:1, more preferably, 100:1.

A hydrogenated amorphous silicon can be typically cited as the amorphous semiconductor, while a polysilicon or the like can be typically cited as a crystalline semiconductor layer. Examples of polysilicon (polycrystalline silicon) include so-called high-temperature polysilicon that contains polysilicon as a main component and is formed at a process temperature greater than or equal to 800° C., so-called low-temperature polysilicon that contains polysilicon as a main component and is formed at a process temperature less than or equal to 600° C., polysilicon obtained by crystallizing amorphous silicon by using an element that promotes crystallization or the like, and the like. It is needless to say that a microcrystalline semiconductor or a semiconductor having a crystal phase in a portion thereof may be used.

As a material of the semiconductor, as well as an element of silicon (Si), germanium (Ge), or the like, a compound semiconductor such as GaAs, InP, SiC, ZnSe, GaN, or SiGe can be used. Further, zinc oxide (ZnO), tin oxide ($SnO_2$), or the like which is an oxide semiconductor can be used. In the case of using ZnO for the semiconductor layer, $Y_2O_3$, $Al_2O_3$, $TiO_2$, a stacked layer thereof, or the like may be used for the gate insulating layer, and ITO, Au, Ti, or the like may be used for the gate electrode layer, the source electrode layer, and the drain electrode layer. In addition, In, Ga, or the like can be added to ZnO.

In the case of using a crystalline semiconductor film for the semiconductor layer, the crystalline semiconductor film may be formed by various methods (such as a laser crystallization method, a thermal crystallization method, or a thermal crystallization method using an element such as nickel which promotes crystallization). Also, a microcrystalline semiconductor, which is an SAS, can be crystallized by laser light irradiation to increase its crystallinity. When the element that promotes the crystallization is not introduced, prior to irradiating an amorphous silicon film with laser light, the amorphous silicon film is heated at 500° C. for one hour under a nitrogen atmosphere to release hydrogen contained in the amorphous silicon film such that the concentration of hydrogen becomes $1 \times 10^{20}$ atoms/$cm^3$ or less. This is because the amorphous silicon film is destroyed when the amorphous silicon film containing a large amount of hydrogen is irradiated with laser light.

As a method of introducing a metal element into an amorphous semiconductor film, any method by which the metal element can be kept on the surface or inside of the amorphous semiconductor film can be used. For example, a sputtering method, a CVD method, a plasma treatment method (including a plasma CVD method), an adsorption method, or a method of applying a metal-salt solution can be used. Among them, a method using a solution is simple and advantageous in that the concentration of the metal element can be easily controlled. At this time, it is desirable to form an oxide film by UV light irradiation in an oxygen atmosphere, a thermal oxidation method, treatment with ozone water containing hydroxyl radical or hydrogen peroxide, or the like to improve wettability of the surface of the amorphous semiconductor film so that an aqueous solution is diffused on the entire surface of the amorphous semiconductor film.

In a crystallization step in which an amorphous semiconductor film is crystallized to form a crystalline semiconductor film, an element which promotes crystallization (also referred to as a catalytic element or a metal element) may be added to the amorphous semiconductor film, and crystallization may be performed by heat treatment (at 550 to 750° C. for 3 minutes to 24 hours). The element promoting crystallization can be one or more of elements such as iron (Fe), nickel (Ni), cobalt (Co), ruthenium (Ru), rhodium (Rh), palladium (Pd), osmium (Os), iridium (Ir), platinum (Pt), copper (Cu), and gold (Au).

In order to remove or reduce the element which promotes crystallization from the crystalline semiconductor film, a semiconductor film containing an impurity element is formed in contact with the crystalline semiconductor film, which functions as a gettering sink. As the impurity element, an impurity element imparting n-type conductivity, an impurity element imparting p-type conductivity, a rare gas element, or the like can be used. For example, one or a plurality of kinds of elements such as phosphorus (P), nitrogen (N), arsenic (As), antimony (Sb), bismuth (Bi), boron (B), helium (He), neon (Ne), argon (Ar), krypton (Kr), and xenon (Xe) can be used. A semiconductor film containing a rare gas element is formed on the crystalline semiconductor film containing the element which promotes crystallization, and heat treatment (at 550 to 750° C. for 3 minutes to 24 hours) is performed. The element which promotes crystallization contained in the crystalline semiconductor film moves into the semiconductor film containing a rare gas element, and thus, the element which promotes crystallization contained in the crystalline semiconductor film is removed or reduced. After that, the semiconductor film containing a rare gas element that has served as a gettering sink is removed.

An amorphous semiconductor film may be crystallized by the combination of heat treatment and laser light irradiation, or one of heat treatment and laser light irradiation may be performed a plurality of times.

A crystalline semiconductor film may be formed directly on a substrate by a plasma method. Alternatively, a crystalline semiconductor film may be selectively formed over the substrate by using the plasma method.

In this embodiment, a polycrystalline silicon film is obtained by a crystallization method using a catalytic element as a semiconductor film. A nickel acetate solution containing nickel of 10 ppm by weight is added by a spinner. It is to be noted that a nickel element may be dispersed over the entire surface by a sputtering method instead of adding the solution. Next, the semiconductor film is crystallized by heat treatment to form a semiconductor film having a crystalline structure (here, polycrystalline silicon film). Here, a polycrystal silicon film is obtained by a heat treatment for crystallization (at 550° C. for 4 hours) after the heat treatment (at 500° C. for one hour).

Next, an oxide film over the surface of the polycrystal silicon film is removed by a dilute hydrofluoric acid or the like. After that, irradiation of laser light (XeCl: wavelength of 308 nm) for raising a degree of crystallization and repairing a defect left in a crystal grain is performed in an atmospheric air or in an oxygen atmosphere.

Excimer laser light of a wavelength of 400 nm or less, or the second harmonic or the third harmonic of a YAG laser is used for the laser light. Here, pulsed laser light having a repetition rate of approximately 10 to 1000 Hz is used. The laser light is condensed to 100 to 500 mJ/cm$^2$ by an optical system, and irradiation is performed with an overlap rate of 90 to 95%, thereby scanning the silicon film surface. In this embodiment, irradiation with laser light having a repetition rate of 30 Hz and energy density of 470 mJ/cm$^2$ is performed in the atmosphere.

Noted that an oxide film is formed over the surface by the laser light irradiation since the irradiation is conducted in an atmospheric air or in an oxygen atmosphere. Note that although an example in which the pulsed laser is used is shown in this embodiment, a continuous wave laser may be used instead. In order to obtain crystal with large grain size at the time of crystallization of a semiconductor film, it is preferable to use a solid laser which is capable of continuous oscillation and to apply the second to fourth harmonic of a fundamental wave. As a typical example, the second harmonic (532 nm) or the third harmonic (355 nm) of an Nd:YVO$_4$ laser (fundamental wave of 1064 nm) may be applied.

In the case of using a continuous wave laser, laser light emitted from the continuous wave type YVO$_4$ laser of 10 W output is converted into harmonics by using a non-linear optical element. The harmonics can also be obtained by putting a YVO$_4$ crystal and a non-linear optical element in a resonator. Then, the laser light having a rectangular shape or an elliptical shape on an irradiated face is preferably formed by an optical system, and an object is irradiated with this laser light. The energy density here is required to be in the range of approximately 0.01 to 100 MW/cm$^2$ (preferably 0.1 to 10 MW/cm$^2$). Then, the semiconductor film is irradiated with the laser light by moving the semiconductor film relatively to the laser light at a rate of about 10 to 2000 cm/s.

Then, in addition to the oxide film formed by the laser light irradiation, a barrier layer made of an oxide film having a thickness of 1 to 5 nm in total is formed by treating the surface with ozone water for 120 seconds. This barrier layer is formed to remove a catalytic element added for crystallization, for example nickel (Ni), from the film. Although the barrier layer is formed by using ozone water here, a barrier layer may also be formed by depositing an oxide film of approximately 1 to 10 nm thick by using a method of oxidizing a surface of a semiconductor film having a crystal structure by UV-ray irradiation in an oxygen atmosphere, a method of oxidizing a surface of a semiconductor film having a crystal structure by an oxygen plasma treatment, plasma CVD, sputtering, evaporation or the like. In addition, before forming the barrier layer, the oxide film formed by laser light irradiation may be removed.

Then, over the barrier layer, an amorphous silicon film containing an argon element is formed to be 10 to 400 nm thick, for example 100 nm thick here, by sputtering to serve as a gettering site. Here, the amorphous silicon film containing an argon element is formed in an atmosphere containing argon using a silicon target. In the case of using a plasma CVD method, the amorphous silicon film containing the argon element is formed under the condition where the flow rate of monosilane to argon (SiH$_4$:Ar) is 1:99, the film-formation pressure is 6.665 Pa, RF power density is 0.087 W/cm$^2$, and the film-formation temperature is 350° C.

After that, the removal (gettering) of the catalytic element is performed by heat treatment for three minutes in a furnace heated to 650° C. Through this treatment, the catalyst element concentration in the semiconductor film having a crystal structure is reduced. A lamp annealing apparatus may be used instead of the furnace.

Subsequently, the amorphous silicon film containing an argon element, which is a gettering site, is selectively removed with the barrier layer as an etching stopper, and then, the barrier layer is selectively removed by dilute hydrofluoric acid. Since nickel tends to move to a region with a high concentration of oxygen in gettering, the barrier layer formed of an oxide film is desirably removed after the gettering.

It is to be noted that, in the case where crystallization of a semiconductor film using a catalytic element is not performed, the above described steps such as the formation of the barrier layer, the formation of the gettering site, the heat treatment for gettering, the removal of the gettering site, and the removal of the barrier layer are not required.

Figure 13A:
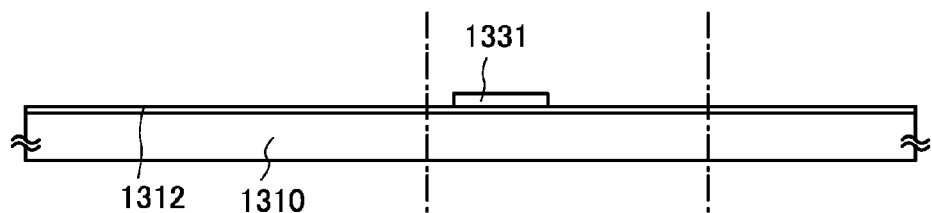
FIGS. 13A to 13D are diagrams illustrating a transistor included in a color sensor.

Next, a thin oxide film is formed on the surface of the obtained semiconductor film having a crystalline structure (for example, a crystalline silicon film) with ozone water, and subsequently, a mask is formed using a resist using a first photomask and the semiconductor film is etched to have a desired shape, so that an island-like semiconductor layer 1331 is formed (see FIG. 13A). After the semiconductor layer 1331 is formed, the resist mask is removed.

Then, if necessary, a small amount of impurity element (boron or phosphorus) is added to control the threshold voltage of a transistor. Here, an ion doping method in which diborane (B$_2$H$_6$) is not excited by plasma without mass separation is used.

Next, a surface of the semiconductor layer 1331 is washed at the same time as removal of an oxide film with an etchant containing hydrofluoric acid. After that, an insulating film, which is to be a gate insulating film 1313, is formed.

The gate insulating film 1313 may be formed using silicon oxide or may be formed to have a stacked structure of silicon oxide and silicon nitride. The gate insulating film 1313 may be formed by depositing an insulating film by a plasma CVD method or a low pressure CVD method or may be formed by solid phase oxidation or solid phase nitridation by plasma treatment. This is because a gate insulating film which is formed using a semiconductor layer which is oxidized or nitrided by plasma treatment is dense, has high withstand voltage, and is excellent in reliability. For example, a surface of the semiconductor layer is oxidized or nitrided using nitrous oxide ($N_2O$) diluted with Ar by 1 to 3 times (flow ratio) by application of a microwave (2.45 GHz) power of 3 to 5 kW at a pressure of 10 to 30 Pa. Through this process, an insulating film of 1 to 10 nm (preferably 2 to 6 nm) thick is formed. Further, nitrous oxide ($N_2O$) and silane ($SiH_4$) are introduced and electric power of microwaves (2.45 GHz) of 3 to 5 kW is applied to the semiconductor layer at a pressure of 10 to 30 Pa to form a silicon oxynitride film by CVD, which is to be a gate insulating film. With a combination of a solid-phase reaction and a reaction by a vapor deposition method, the gate insulating film with low interface state density and excellent withstand voltage can be formed.

Alternatively, as the gate insulating film 1313, a high dielectric constant material such as zirconium dioxide, hafnium oxide, titanium dioxide, tantalum pentoxide, or the like may be used. When a high dielectric constant material is used for the gate insulating film 1313, gate leakage current can be reduced.

In this embodiment, as the gate insulating film 1313, a silicon oxide film containing nitrogen is formed to a thickness of 115 nm by a plasma CVD method.

Figure 13B:
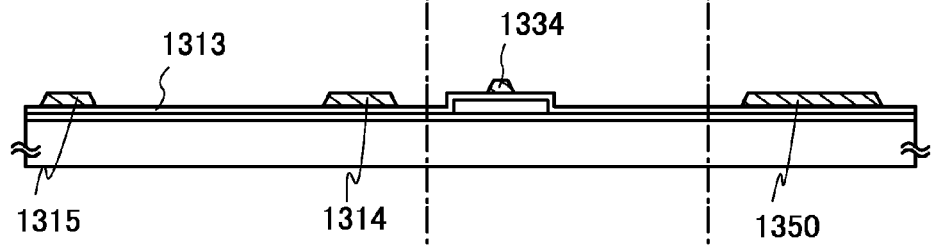

Next, after a metal film is formed over the gate insulating film 1313, a gate electrode 1334, wirings 1314 and 1315, and a terminal electrode 1350 are formed using a second photomask (see FIG. 13B). As the metal film, for example, a film is used, in which tantalum nitride and tungsten (W) are stacked to be 30 nm and 370 nm respectively.

In addition, other than the above-described material, an element selected from titanium (Ti), tungsten (W), tantalum (Ta), molybdenum (Mo), neodymium (Nd), cobalt (Co), zirconium (Zr), zinc (Zn), ruthenium (Ru), rhodium (Rh), palladium (Pd), osmium (Os), iridium (Ir), platinum (Pt), aluminum (Al), gold (Au), silver (Ag), or copper (Cu); a single-layer film formed from an alloy material or a compound material containing the element as its main component; or nitride of these can be used as the gate electrode 1334, the wirings 1314 and 1315, and the terminal electrode 1350.

Alternatively, as the gate electrode 1334, the wirings 1314 and 1315, and the terminal electrode 1350, a light-transmitting material which transmits visible light may be used. As the light-transmitting conductive material, indium tin oxide (ITO), indium tin oxide containing silicon oxide (ITSO), organic indium, organic tin, zinc oxide, or the like can be used. Alternatively, indium zinc oxide (IZO) containing zinc oxide (ZnO), zinc oxide (ZnO), ZnO doped with gallium (Ga), tin oxide ($SnO_2$), indium oxide containing tungsten oxide, indium zinc oxide containing tungsten oxide, indium oxide containing titanium oxide, indium tin oxide containing titanium oxide, or the like may be used.

Figure 13C:
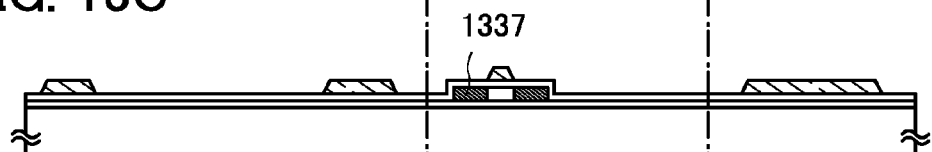

Next, an impurity imparting one conductivity type is introduced into the semiconductor layer 1331 to form a source and drain regions 1337 of a transistor 1373 (see FIG. 13C). In this embodiment, an n-channel transistor is formed; therefore, an impurity imparting n-type conductivity, for example, phosphorus (P) or arsenic (As) is introduced into the semiconductor layer 1331. In the case where a p-channel transistor is formed, an impurity imparting p-type conductivity, for example, boron (B) may be introduced into the semiconductor layer 1331.

Subsequently, after a first interlayer insulating film containing silicon oxide film (not shown) is formed to 50 nm by a CVD method, a step for an activation treatment of an impurity element added to each island-like semiconductor region is conducted. The activation step is conducted by rapid thermal annealing (RTA method) using a lamp light source, a method of irradiation of a YAG laser or an excimer laser from the back side, a heat treatment using a furnace, or a method which is a combination of the foregoing methods.

Next, a second interlayer insulating film 1316 including a silicon nitride film containing hydrogen and oxygen is formed to have a thickness of, for example, 10 nm.

Figure 13D:
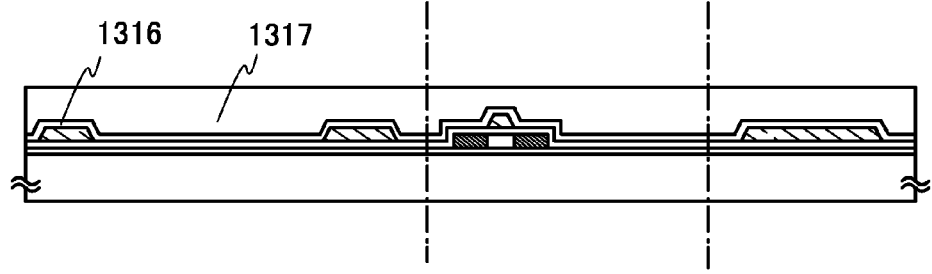

Next, a third interlayer insulating film 1317 formed using an insulating material is formed over the second interlayer insulating film 1316 (see FIG. 13D). As for the third interlayer insulating film 1317, an insulating film obtained by a CVD method can be used. In this embodiment, in order to improve adhesion, a silicon oxide film containing nitrogen is formed to be 900 nm thick as the third interlayer insulating film 1317.

Then, heat treatment (heat treatment at 300 to 550° C. for 1 to 12 hours, for example, at 410° C. for 1 hour in a nitrogen atmosphere) is conducted in order to hydrogenate the semiconductor layer. This step is conducted to terminate dangling bonds in the semiconductor layer caused by hydrogen contained in the second interlayer insulating film 1316. The semiconductor layer can be hydrogenated regardless of whether or not the gate insulating film 1313 is formed.

In addition, as the third interlayer insulating film 1317, an insulating film using siloxane and a stacked structure thereof can also be used. Note that siloxane includes a skeleton formed from a bond of silicon (Si) and oxygen (O). As a substituent, a compound containing at least hydrogen (for example, an alkyl group or an aryl group) is used. Fluorine may also be used as a substituent. Moreover, a compound containing at least hydrogen and fluorine may be used as a substituent.

In the case where an insulating film using siloxane or a stacked structure thereof is used as the third interlayer insulating film 1317, after formation of the second interlayer insulating film 1316, heat treatment to hydrogenate the semiconductor layer may be performed, and then, the third interlayer insulating film 1317 may be formed.

Next, a resist mask is formed by using a third photo mask to selectively etch the first interlayer insulating film, the second interlayer insulating film 1316, and the third interlayer insulating film 1317 or the gate insulating film 1313, whereby contact holes are formed. Then, the resist mask is removed.

It is to be noted that the third interlayer insulating film 1317 may be formed if necessary. When the third interlayer insulating film 1317 is not formed, after forming the second interlayer insulating film 1316, the first interlayer insulating film, the second interlayer insulating film 1316, and the gate insulating film 1313 are selectively etched to form a contact hole.

Next, after formation of a metal stacked film by a sputtering method, a resist mask is formed using a fourth photomask, and then, the metal film is selectively etched to form a wiring 1319, a connection electrode 1320, a terminal electrode 1351, a source electrode and drain electrodes 1341 of the transistor 1373. Then, the resist mask is removed. Note that the metal film of this embodiment is a stacked-layer film with three films: a Ti film with a thickness of 100 nm, an Al film containing a very small amount of Si with a thickness of 350 nm, and a Ti film with a thickness of 100 nm.

In addition, in a case where each of the wiring 1319, the connection electrode 1320, the terminal electrode 1351, and the source electrode and drain electrodes 1341 of the transistor 1373 is formed of a single-layer conductive film, a titanium film (Ti film) is preferable in terms of heat resistance, conductivity, and the like. Instead of a titanium film, a single-layer film formed from an element selected from tungsten (W), tantalum (Ta), molybdenum (Mo), neodymium (Nd), cobalt (Co), zirconium (Zr), zinc (Zn), ruthenium (Ru), rhodium (Rh), palladium (Pd), osmium (Os), iridium (Ir) and platinum (Pt), or an alloy material or a compound material containing the above element as its main component; a single-layer film formed from nitride thereof, for example, titanium nitride, tungsten nitride, tantalum nitride, or molybdenum nitride may be used. The number of times of deposition can be reduced in the manufacturing process, by formation of each of the wiring 1319, the connection electrode 1320, the terminal electrode 1351, and the source electrode and drain electrodes 1341 of the transistor 1373 as a single-layer film.

The top gate transistor 1373 using a polycrystalline silicon film as the semiconductor layer can be manufactured through the process described above.

Although an n-channel transistor is used as a semiconductor element included in the semiconductor element layer in this embodiment, a p-channel transistor may alternatively be used. Any of a variety of types of field effect transistors can be employed, and there is no limitation on an applicable type of the transistor.

Although a transistor having a single-gate structure is described in this embodiment, a transistor having a multi-gate structure such as a double-gate structure may alternatively be employed. In this case, gate electrode layers may be provided above and below the semiconductor layer or a plurality of gate electrode layers may be provided only on one side (above or below) of the semiconductor layer.

A transistor or the like formed by using an inkjet method or a printing method can be used. Accordingly, transistors can be formed at room temperature, can be formed at a low vacuum, or can be formed using a large substrate. Also, since the transistor can be manufactured without using a mask (a reticle), a layout of the transistor can be changed easily. Further, since it is not necessary to use a resist, the material cost is reduced and the number of steps can be reduced. Furthermore, since a film is formed only in a portion where the film is necessary, a material is not wasted compared with a manufacturing method in which etching is performed after a film is formed over the entire surface, so that the cost can be reduced.

Further, transistors or the like including an organic semiconductor or a carbon nanotube can be used. With these, the transistor can be formed over a substrate that can be bent. Therefore, such transistors can resist a shock.

Alternatively, a transistor may be formed using a light-transmitting SOI substrate or the like using a single crystal semiconductor layer as a semiconductor layer. Therefore, a transistor with almost no variations in characteristics, sizes, shapes, or the like, with high current supply capacity, and of small size can be formed. By using such a transistor, power consumption of a circuit can be reduced or a circuit can be highly integrated.

The optical sensor of this embodiment can be formed over a light-transmitting substrate such as a glass substrate by forming a field effect transistor using a thin film transistor. Therefore, even if the photoelectric conversion element is formed over a substrate, the photoelectric conversion element can receive light which has passed through the substrate from the back surface thereof.

Figure 14A:
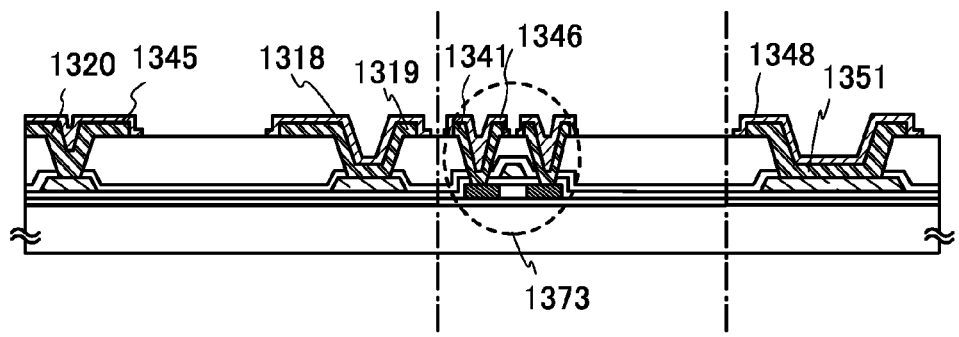
FIGS. 14A to 14C are diagrams illustrating a transistor included in a color sensor.

Subsequently, after formation of a conductive metal film (such as titanium (Ti) or molybdenum (Mo)) which is not likely to be an alloy by reacting with a photoelectric conversion layer (typically, amorphous silicon) which is formed later, a resist mask is formed using a fifth photomask, and then, the conductive metal film is selectively etched to form protective electrodes 1318, 1345, 1346, and 1348 which cover the wiring 1319 (see FIG. 14A). Here, a Ti film with 200 nm thick obtained by a sputtering method is formed. Note that the connection electrode 1320, the terminal electrode 1351, and the source electrode and drain electrodes 1341 of the transistor 1373 are covered with a conductive metal film in the same manner. Therefore, the conductive metal film also covers a side face where an Al film which is a second layer in the electrode is exposed, thereby preventing diffusion of an aluminum atom into the photoelectric conversion layer.

Note that in the case where each of the wiring 1319, the connection electrode 1320, the terminal electrode 1351, and the source and drain electrodes 1341 of the transistor 1373 are formed using a single-layer conductive film, the protective electrodes 1318, 1345, 1346, and 1348 are not necessarily formed.

Next, a photoelectric conversion layer 1371 including a p-type semiconductor layer 1371p, an i-type semiconductor layer 1371i, and an n-type semiconductor layer 1371n is formed over the third interlayer insulating film 1317.

The p-type semiconductor layer 1371p may be formed by deposition of a semi-amorphous (also referred to as microcrystalline or micro crystal) silicon film containing an impurity element which belongs to group 13 of the periodic table, such as boron (B), by a plasma CVD method.

As one example of a method for forming a microcrystalline silicon film, a method in which a microcrystalline silicon film is formed by glow discharge plasma in the mixed gas of a silane gas and hydrogen, or a silane gas, hydrogen, and a rare gas can be given. Since silane is diluted 10 to 2000 times with hydrogen and/or a rare gas, a large amount of hydrogen and/or the rare gas is needed. A temperature for heating the substrate is from 100 to 300° C., preferably from 120 to 220° C. It is preferable that deposition be performed at a temperature of 120 to 220° C. in order that a growing surface of the microcrystalline silicon film is inactivated with hydrogen, and growth of microcrystalline silicon is promoted. In the deposition treatment, crystals of a SiH radical, a $SiH_2$ radical, and a $SiH_3$ radical which are active species are grown from the crystal nuclei. Further, an energy band width may be adjusted by mixing germanium hydride or germanium fluoride such as $GeH_4$ or $GeF_4$ into a gas such as silane or adding carbon or germanium to silicon. In the case where carbon is added to silicon, an energy band width is increased, and in the case where germanium is added to silicon, an energy band width is reduced.

In addition, the wiring 1319 and the protective electrode 1318 are in contact with the bottom layer of the photoelectric conversion layer 1371, in this embodiment, the p-type semiconductor layer 1371p.

After the formation of the p-type semiconductor layer 1371p, the i-type semiconductor layer 1371i and the n-type semiconductor layer 1371n are sequentially formed. Thus, the photoelectric conversion layer 1371 including the p-type semiconductor layer 1371p, the i-type semiconductor layer 1371i, and the n-type semiconductor layer 1371n is formed.

As the i-type semiconductor layer 1371i, for example, a microcrystalline silicon film may be formed by a plasma CVD method. Note that as the n-type semiconductor layer 1371n, a microcrystalline silicon film containing an impurity element which belongs to Group 15 of the periodic table, for example, phosphorus (P) may be formed, or after formation of a microcrystalline silicon film, an impurity element which belongs to Group 15 of the periodic table may be introduced.

As the p-type semiconductor layer 1371p, the i-type semiconductor layer 1371i, and the n-type semiconductor layer 1371n, an amorphous semiconductor film may be used as well as a microcrystalline semiconductor film. Alternatively, a polycrystalline semiconductor film formed using the above catalyst or the above laser crystallization process may be used.

Further, in a photoelectric conversion layer formed using microcrystalline silicon or single crystal silicon which is formed by Smart Cut (registered trademark) method, variations in characteristics of a surface of the substrate can be suppressed.

Figure 14B:
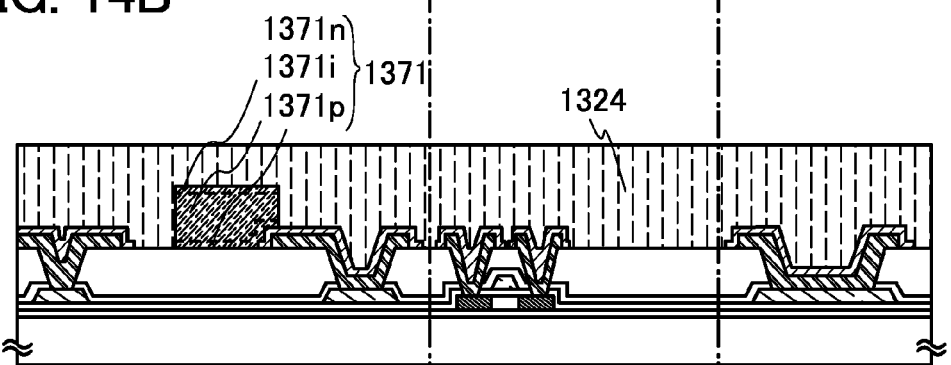
Figure 14C:
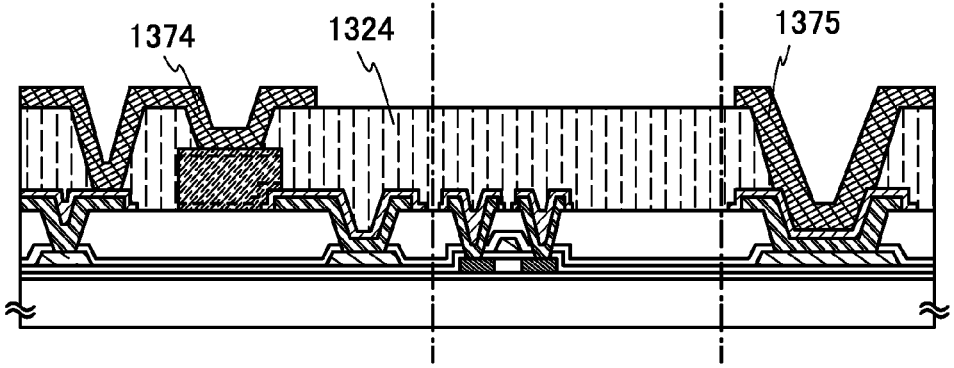

Next, a sealing layer 1324 is formed using an insulating material (for example, an inorganic insulating film containing silicon) to a thickness of 1 to 30 μm over the entire surface to obtain a state shown in FIG. 14B. Here, as an insulating material film, a silicon oxide film containing nitrogen with a thickness of 1 μm is formed by a CVD method. It is intended that adhesiveness be improved by using the insulating film formed by CVD.

Subsequently, after the sealing layer 1324 is etched to provide openings, wirings 1374 and 1375 are formed by a sputtering method. The wirings 1374 and 1375 are titanium films (a Ti film) (thickness of 200 nm) which are obtained by a sputtering method.

Figure 15A:
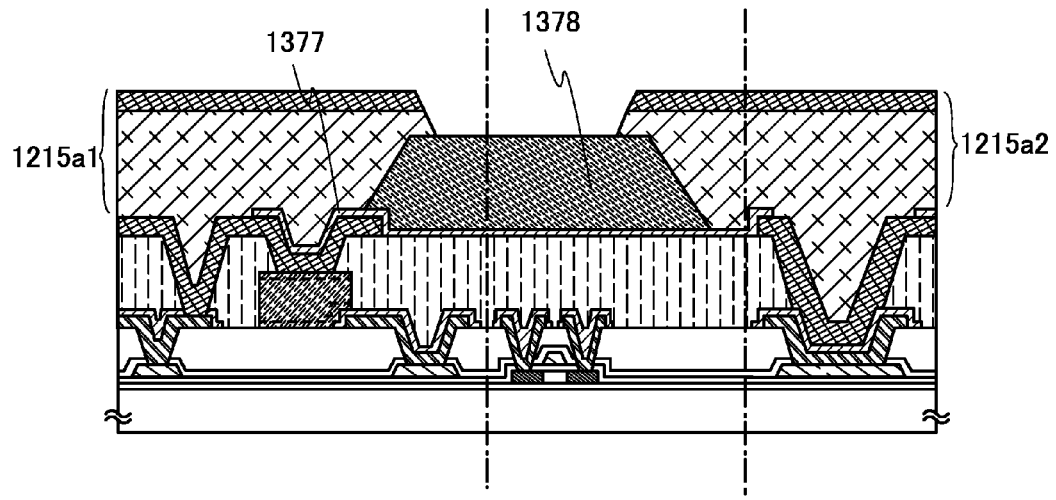
FIGS. 15A and 15B are diagrams illustrating a transistor included in a color sensor.

Next, a protective film 1377 is formed to cover an exposed surface (See FIG. 15A). As the protective film 1377, a silicon nitride film is used in this embodiment. The protective film 1377 makes it possible to prevent mixing of impurities such as moisture and organic matter into the transistor 1373 and the photoelectric conversion layer 1371.

Next, a sealing film 1378 is formed over the protective film 1377. Also, the sealing film 1378 has a function of protecting a semiconductor element layer from external stress. In this embodiment, the sealing film 1378 is formed to a thickness of 20 μm with a photosensitive epoxy-phenol-based resin. As the sealing film 1378, Ohmcoat which is an epoxy-phenol-based resin is used.

Next, a contact hole is formed by etching a region of the protective film, where a terminal electrode in an upper layer is electrically connected to the wiring 1374 or the wiring 1375 in a lower layer.

Next, a stack of a titanium film (Ti film) (150 nm), a nickel film (Ni film) (750 nm), and a gold film (Au film) (50 nm) are formed over the sealing film 1378 using nickel (Ni) paste by a sputtering method, for example. The terminal electrode 1215a1 and the terminal electrode 1215a2 thus obtained have fixing intensity over 5N, which is sufficient fixing intensity as a terminal electrode.

Figure 15B:
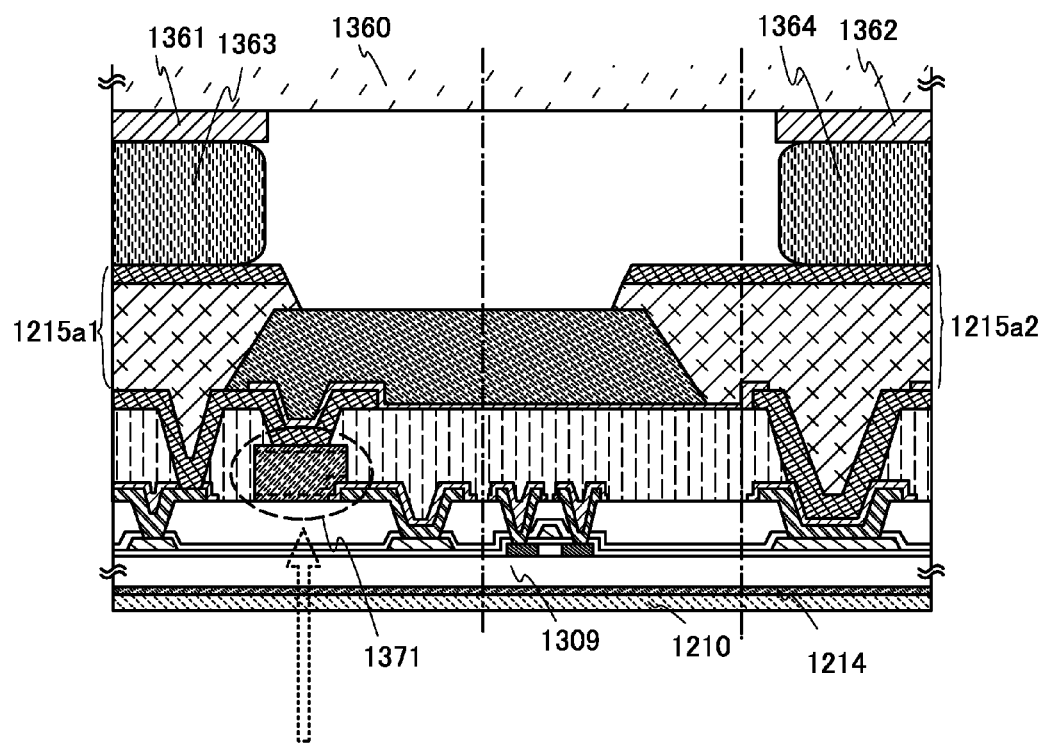

Through the steps described above, the terminal electrodes 1215a1 and 1215a2 which can be connected by a solder are formed, and a structure illustrated in FIG. 15B can be obtained.

In practice, mass production of semiconductor element layers each of which include a photoelectric conversion element, a transistor, and the like, and which are formed at the time of FIG. 15B is possible by formation of element materials over a large substrate. A large number of optical sensors (for example, an optical sensor chip with an area of 2 mm×1.5 mm) can be manufactured from one large substrate (for example, a substrate with an area of 600 cm×720 cm).

A light-transmitting substrate 1309 over which a semiconductor element layer is formed is an example of further mounting the light-transmitting substrate 1309 on an interposer 1360 by solder 1363 and 1364 at portions of the terminal electrodes 1215a1 and 1215a2 (see FIG. 15B). Note that an electrode 1361 on the interposer 1360 is mounted over the terminal electrode 1215a1 by the solder 1363. In addition, an electrode 1362 on the interposer 1360 is mounted over the terminal electrode 1215a2 by the solder 1364.

In the photoelectric conversion element illustrated in FIG. 15B, light which enters the photoelectric conversion layer 1371 can be transmitted from the light-transmitting substrate 1309 and the light-transmitting resin layers 1210 and 1214 side by using the light-transmitting substrate 1309 and the light-transmitting resin layers 1210 and 1214.

According to this embodiment, an optical sensor may be provided in a housing which has an opening in an incident region where light is delivered to a photoelectric conversion element or which has a light-transmitting region formed using a light-transmitting material. Since the photoelectric conversion element is made to detect light which has passed through the chromatic color light-transmitting resin layer, light which is transmitted from the outside through a region where the chromatic color light-transmitting resin layer is formed to enter the photoelectric conversion element can be blocked by covering the region where the chromatic color light-transmitting resin layer is formed with a housing. Therefore, accuracy of the optical sensor as a sensor is improved, and discrepancy can be reduced.

The optical sensor is manufactured through the manufacturing process described above, and thus the optical sensor can be manufactured at low unit cost and with high yield.

In addition, the thickness of the light-transmitting substrate is reduced before the light-transmitting substrate is divided, and the dividing step is performed in two steps; therefore, it is possible to reduce the wear of a cutting tool in the process of dividing the light-transmitting substrate. The processing region of a cutting tool is increased with an increase in size of a light-transmitting substrate and a decrease in size of an optical sensor to be divided, which causes a further increase in wear of the cutting tool. Therefore, the structure of this embodiment in which wear of the cutting tool can be reduced is especially beneficial for a large substrate and a smaller optical sensor. Accordingly, an optical sensor and a color sensor can be manufactured at lower cost. Since the light-transmitting substrate is thin, the size of the optical sensor and the color sensor can be made small.

Thus, it is possible to provide a color sensor that is easy to be handled and has high reliability even if it has a small thickness. The contents described in each drawing in this embodiment can be freely combined with or replaced with the contents described in another embodiment as appropriate. Therefore, in the color sensor, the number of terminals which increases by the provision of a plurality of optical sensors can be reduced over the interposer. Specifically, terminals to which high power supply potentials are input can be made to be a common terminal over the interposer, and terminals to which low power supply potentials are input can be made to be a common terminal over the interposer. Accordingly, the number of terminal electrodes can be significantly reduced. By reducing the number of terminal electrodes, suppression of a defect of connection with an external device can be achieved, whereby an yield can be improved. Further, the structure of this embodiment can achieve pin compatibility when the plurality of optical sensors is provided over the interposer to form the color sensor.

(Embodiment Mode 3)

In the color sensor of any of the above embodiments, a field effect transistor with various forms can be used as the semiconductor element included in the semiconductor element layer of the optical sensor. In this embodiment, a field effect transistor including a single crystal semiconductor layer is described in detail as a semiconductor element which can be applied to an optical sensor.

A method in which a semiconductor element included in a semiconductor element layer is formed over a light-transmitting substrate by forming a single crystal semiconductor layer using a single crystal semiconductor substrate will be described below with reference to FIGS. 16A to 16D and FIGS. 17A to 17C.

Figure 16A:
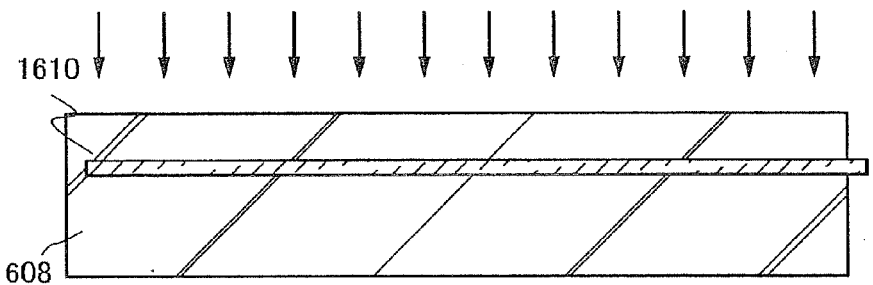
FIGS. 16A to 16D are diagrams illustrating a transistor included in a color sensor.

A single crystal semiconductor substrate 1608 illustrated in FIG. 16A is cleaned, and a predetermined depth from the surface of the single crystal semiconductor substrate 1608 is irradiated with ions accelerated by an electric field, whereby an embrittlement layer 1610 is formed. The ion irradiation is performed in consideration of the thickness of a single crystal semiconductor layer that is to be transferred to a light-transmitting substrate. The ion irradiation is performed on the single crystal semiconductor substrate 1608 at an accelerating voltage determined in accordance with such a thickness. In this embodiment, a region that is embrittled by ion irradiation on a single crystal semiconductor substrate so as to include microvoids due to the ions is referred to as an embrittlement layer.

A commercial single crystal semiconductor substrate can be used as the single crystal semiconductor substrate 1608. For example, a single crystal semiconductor substrate including an element belonging to Group 4, such as a single crystal silicon substrate, a single crystal germanium substrate, or a single crystal silicon-germanium substrate can be used. Alternatively, a compound semiconductor substrate formed of gallium arsenide, indium phosphide, or the like can be used. As the semiconductor substrate, a polycrystalline semiconductor substrate may also be used. It is needless to say that the single crystal semiconductor substrate is not limited to a circular wafer, and single crystal semiconductor substrates with various shapes can be used. For example, a circular substrate or a polygonal substrate such as a rectangular substrate, a pentagonal substrate, or a hexagonal substrate can be used. Needless to say, a commercial circular single crystal semiconductor wafer can also be used as the single crystal semiconductor substrate. As the circular single crystal semiconductor wafer, there are a semiconductor wafer of silicon, germanium, or the like, a compound semiconductor wafer of gallium arsenide, indium phosphide, or the like, and the like. The single crystal semiconductor wafer is typified by circular single crystal silicon wafers that are 5 inches (125 mm) in diameter, 6 inches (150 mm) in diameter, 8 inches (200 mm) in diameter, 12 inches (300 mm) in diameter, 400 mm in diameter, and 450 mm in diameter. Moreover, a rectangular single crystal semiconductor substrate can be formed by cutting a commercial circular single crystal semiconductor wafer. The substrate can be cut with a cutting device such as a dicer or a wire saw, laser cutting, plasma cutting, electron beam cutting, or any other appropriate cutting means. Alternatively, a rectangular single crystal semiconductor substrate can be formed in such a way that an ingot for manufacturing a semiconductor substrate before being sliced into a substrate is processed into a rectangular solid so as to have a rectangular cross section and the rectangular solid ingot is sliced. There is no particular limitation on the thickness of the single crystal semiconductor substrate. However, the thicker a single crystal semiconductor substrate is, the more single crystal semiconductor layers can be obtained from one piece of material wafer. Therefore, it is preferable that the single crystal semiconductor substrate be thick in terms of reusing the single crystal semiconductor substrate. The size of single crystal silicon wafers on the market conforms to SEMI standards, which specify that, for example, a wafer with a diameter of 6 inches has a thickness of 625 µm, a wafer with a diameter of 8 inches has a thickness of 725 µm, and a wafer with a diameter of 12 inches has a thickness of 775 µm. Note that the thickness of a wafer conforming to SEMI standards has a tolerance of ±25 µm. It is needless to say that the thickness of the single crystal semiconductor substrate to be a material wafer is not limited to SEMI standards, and the thickness can be adjusted as appropriate when an ingot is sliced. Naturally, when the single crystal semiconductor substrate 1608 is reused, the thickness of the substrate is smaller than that of SEMI standards. A single crystal semiconductor layer provided over a light-transmitting substrate can be determined by selecting a semiconductor substrate used as a material wafer.

Furthermore, the crystal plane of the single crystal semiconductor substrate 1608 may be selected depending on a semiconductor element to be manufactured (a field-effect transistor in this embodiment). For example, a single crystal semiconductor substrate having a {100} plane, a {110} plane, or the like can be used.

In this embodiment, an ion irradiation separation method is used in which ions of hydrogen, helium, or fluorine are added to a predetermined depth of the single crystal semiconductor substrate by ion irradiation, and then heat treatment is performed to separate a single crystal semiconductor layer that is a surface layer. Another method may also be employed in which single crystal silicon is epitaxially grown on porous silicon and the porous silicon layer is separated by cleavage with water jetting A single crystal silicon substrate is used as the single crystal semiconductor substrate 1608. A surface of the single crystal semiconductor substrate 1608 is processed with dilute hydrofluoric acid to remove a native oxide film and contaminants such as dust attached to the surface, thereby being cleaned.

The embrittlement layer 1610 may be formed by ion irradiation by an ion doping method (abbreviated as an ID method) or an ion implantation method (abbreviated as an II method). The embrittlement layer 1610 is formed by irradiation of ions of hydrogen, helium, or halogen typified by fluorine. When fluorine ions are used as a halogen element for the ion irradiation, $BF_3$ may be used as a source gas. Note that ion implantation is a method in which an ionized gas is mass-separated and a semiconductor substrate is irradiated with the ionized gas.

For example, an ionized hydrogen gas is mass-separated by an ion implantation method and only $H^+$ ions (or only $H_2^+$ ions) can be selectively accelerated to irradiate the single crystal semiconductor substrate.

In an ion doping method, without mass separation of an ionized gas, plural kinds of ion species are generated in plasma and accelerated, and then a single crystal semiconductor substrate is irradiated with the accelerated ion species. In the case where the single crystal semiconductor substrate is irradiated with hydrogen ions including $H^+$ ions, $H_2^+$ ions, and $H_3^+$ ions, the proportion of $H_3$ ions is typically 50% or more, for example, in general, the proportion of $H_3^+$ ions is 80% and the proportion of other ions ($H^+$ ions and $H_2^+$ ions) is 20%. Here, an ion doping also includes irradiation of only ion species of $H_3^+$ ions.

In addition, a single kind of ions or plural kinds of ions of the same atom that have different masses may be used for the ion irradiation. For example, when irradiation of hydrogen ions is performed, it is preferable to contain $H^+$ ions, $H_2^+$ ions, and $H_3^+$ ions and to have a high proportion of $H_3^+$ ions. In the case of irradiation of hydrogen ions, when $H^+$ ions, $H_2^+$ ions, and $H_3^+$ ions are contained and the proportion of $H_3^+$ ions is high, irradiation efficiency can be increased and irradiation time can be shortened. With such a structure, separation can be performed easily.

Hereinafter, an ion doping method and an ion implantation method will be described in detail. With the use of an ion doping apparatus (also referred to as an ID apparatus) used in an ion doping method, since the plasma space is large, the single crystal semiconductor substrate can be irradiated with a large amount of ions. On the other hand, an ion implantation apparatus (also referred to as an II apparatus) used in an ion implantation method has a characteristic that ions extracted from plasma are mass-analyzed and only specific ion species can be implanted into a semiconductor substrate. In the ion implantation method, processing is usually performed by scanning with a point beam.

Both of the apparatuses generate a plasma state by thermoelectrons that are generated by heating of a filament. However, an ion doping method and an ion implantation method differ greatly in the proportion of the hydrogen ion species in irradiating the semiconductor substrate with hydrogen ions ($H^+$, $H_2^+$, $H_3^+$) which are generated.

For irradiation of a larger amount of $H_3^+$, the ion doping apparatus is preferable to the ion implantation apparatus.

When the single crystal silicon substrate is irradiated with hydrogen ions or halogen ions such as fluorine ions, fluorine or the like that is added knocks out (expels) silicon atoms in a silicon crystal lattice, so that blank portions are created effectively and microvoids are made in the embrittlement layer. In this case, the volume change of the microvoids formed in the embrittlement layer occurs by heat treatment at a relatively low temperature, and a thin single crystal semiconductor layer can be formed by separating along the embrittlement layer. After the irradiation of fluorine ions, irradiation of hydrogen ions may be performed, so that hydrogen may be contained in the voids. Since the embrittlement layer that is formed to separate the thin single crystal semiconductor layer from the single crystal semiconductor substrate is separated using the volume change of the microvoids formed in the embrittlement layer, it is preferable to make effective use of fluorine ion action or hydrogen ion action in such a manner.

In addition, a protective layer may be formed between the single crystal semiconductor substrate and the insulating layer that is to be bonded to the single crystal semiconductor layer. The protective layer can be a single layer or stacked layers selected from a silicon nitride layer, a silicon oxide layer, a silicon nitride oxide layer, and a silicon oxynitride layer. These layers can be formed over the single crystal semiconductor substrate before the embrittlement layer is formed in the single crystal semiconductor substrate. Alternatively, these layers may be formed over the single crystal semiconductor substrate after the embrittlement layer is formed in the single crystal semiconductor substrate.

Note that a silicon oxynitride film means a film that contains more oxygen than nitrogen and, in the case where measurements are performed using Rutherford backscattering spectrometry (RBS) and hydrogen forward scattering (HFS), includes oxygen, nitrogen, silicon, and hydrogen at concentrations ranging from 50 at. % to 70 at. %, 0.5 at. % to 15 at. %, 25 at. % to 35 at. %, and 0.1 at. % to 10 at. %, respectively. Further, a silicon nitride oxide film means a film that contains more nitrogen than oxygen and, in the case where measurements are performed using RBS and HFS, includes oxygen, nitrogen, silicon, and hydrogen at concentrations ranging from 5 at. % to 30 at. %, 20 at. % to 55 at. %, 25 at. % to 35 at. %, and 10 at. % to 30 at. %, respectively. Note that percentages of nitrogen, oxygen, silicon, and hydrogen fall within the ranges given above, where the total number of atoms contained in the silicon oxynitride film or the silicon nitride oxide film is defined as 100 atomic %.

It is necessary to perform irradiation of ions under high dose conditions in the formation of the embrittlement layer, and the surface of the single crystal semiconductor substrate 1608 becomes rough in some cases. Therefore, a protective layer against the ion irradiation, such as silicon nitride film, a silicon nitride oxide film, or a silicon oxide film may be provided to a thickness of 50 to 200 nm on the surface which is irradiated with ions.

For example, as the protective layer, a silicon oxynitride film (5 to 300 nm in thickness, and preferably 30 to 150 nm (e.g., 50 nm) in thickness) and a silicon nitride oxide film (5 to 150 nm in thickness, and preferably 10 to 100 nm (e.g., 50 nm) in thickness) are stacked over the single crystal semiconductor substrate 1608 by plasma CVD. As an example, a silicon oxynitride film with a thickness of 50 nm is formed over the single crystal semiconductor substrate 1608, and a silicon nitride oxide film with a thickness of 50 nm is stacked over the silicon oxynitride film. The silicon oxynitride film may be a silicon oxide film formed by chemical vapor deposition using an organosilane gas.

Alternatively, the single crystal semiconductor substrate 1608 may be degreased and cleaned to remove an oxide film of the surface, and thermal oxidation may be performed. Although normal dry oxidation may be performed as the thermal oxidation, it is preferable to perform oxidation in an oxidizing atmosphere to which halogen is added. For example, heat treatment is performed at a temperature of 700° C. or higher in an atmosphere that contains HCl at 0.5 to 10% by volume (preferably, 3% by volume) with respect to oxygen. Preferably, thermal oxidation is performed at a temperature of 950 to 1100° C. Processing time may be set to 0.1 to 6 hours, and preferably 0.5 to 3.5 hours. An oxide film to be formed has a thickness of 10 to 1000 nm (preferably, 50 to 200 nm), for example, 100 nm.

As a substance containing halogen, one or more selected from HF, $NF_3$, HBr, $Cl_2$, $ClF_3$, $BCl_3$, $F_2$, $Br_2$, dichloroethylene, and the like can be used instead of HCl.

When heat treatment is performed in such a temperature range, a gettering effect by a halogen element can be obtained. Gettering particularly has an effect of removing a metal impurity. That is, by the action of chlorine, impurities such as metal turn into a volatile chloride, and then are diffused into the air to be removed. The heat treatment has an advantageous effect on the surface of the single crystal semiconductor substrate 1608 that is subjected to chemical mechanical polishing (CMP) treatment. In addition, hydrogen has an effect of compensating a defect at the interface between the single crystal semiconductor substrate 1608 and the insulating layer so as to lower a localized-level density at the interface, whereby the interface between the single crystal semiconductor substrate 1608 and the insulating layer is inactivated to stabilize electric characteristics.

Halogen can be contained in the oxide film formed by this heat treatment. When a halogen element is contained at a concentration of $1\times10^{17}$ atoms/cm$^3$ to $5\times10^{20}$ atoms/cm$^3$, the oxide film can function as a protective layer that traps impurities such as metal and prevents contamination of the single crystal semiconductor substrate 1608.

When the embrittlement layer 1610 is formed, the accelerating voltage and the number of total ions can be adjusted by the thickness of a film stacked over the single crystal semiconductor substrate, the thickness of the targeted single crystal semiconductor layer that is separated from the single crystal semiconductor substrate and transferred to a light-transmitting substrate, and ion species for irradiation.

For example, the embrittlement layer can be formed by an ion doping method in such a manner that a hydrogen gas is used as a raw material, and irradiation of ions is performed at an accelerating voltage of 40 kV with a total ion number of $2\times10^{16}$ ions/cm$^2$. If the protective layer is increased in thickness, when the embrittlement layer is formed by irradiation of ions under the same conditions, a thinner single crystal semiconductor layer can be formed as a target single crystal semiconductor layer that is separated from the single crystal semiconductor substrate and transferred (transposed) to the light-transmitting substrate. For example, although it depends on the proportion of ion species ($H^+$, $H_2^+$ and $H_3^+$ ions), in the case where the embrittlement layer is formed under the above conditions and a silicon oxynitride film (50 nm in thickness) and a silicon nitride oxide film (50 nm in thickness) are stacked as a protective layer over the single crystal semiconductor substrate, the thickness of the single crystal semiconductor layer to be transferred to the light-transmitting substrate is about 120 nm; and in the case where a silicon oxynitride film (100 nm in thickness) and a silicon nitride oxide film (50 nm in thickness) are stacked as a protective layer over the single crystal semiconductor substrate, the thickness of the single crystal semiconductor layer to be transferred to the light-transmitting substrate is about 70 nm.

When helium (He) or hydrogen is used as a source gas, the embrittlement layer can be formed by performing irradiation at an accelerating voltage in the range of 10 kV to 200 kV and a dosage in the range of $1\times10^{16}$ ions/cm$^2$ to $6\times10^{16}$ ions/cm$^2$. When helium is used as a source gas, $He^+$ ions can be used as main ions for irradiation even when mass separation is not performed. In addition, when hydrogen is used as a source gas, $H_3^+$ ions and $H_2^+$ ions can be used as main ions for irradiation. The ion species also change depending on the plasma generation method, pressure, the amount of source gas, or accelerating voltage.

As an example of forming the embrittlement layer, a silicon oxynitride film (50 nm in thickness), a silicon nitride oxide film (50 nm in thickness), and a silicon oxide film (50 nm in thickness) are stacked as a protective layer over the single crystal semiconductor substrate, and irradiation of hydrogen is performed at an accelerating voltage of 40 kV and a dosage of $2\times10^{16}$ ions/cm$^2$, whereby the embrittlement layer is formed in the single crystal semiconductor substrate. Then, a silicon oxide film (50 nm in thickness) is formed as an insulating layer having a bonded surface over the silicon oxide film that is the uppermost layer of the protective layer. As another example of forming the embrittlement layer, a silicon oxide film (100 nm in thickness) and a silicon nitride oxide film (50 nm in thickness) are stacked as a protective layer over the single crystal semiconductor substrate, and irradiation of hydrogen is performed at an accelerating voltage of 40 kV and a dosage of $2\times10^{16}$ ions/cm$^2$, whereby the embrittlement layer is formed in the single crystal semiconductor substrate. Then, a silicon oxide film (50 nm in thickness) is formed as an insulating layer having a bonded surface over the silicon nitride oxide film that is the uppermost layer of the protective layer. Note that the silicon oxynitride film and the silicon nitride oxide film may be formed by plasma CVD, and the silicon oxide film may be formed by CVD using an organosilane gas.

Furthermore, an insulating layer may be formed between the light-transmitting substrate and the single crystal semiconductor substrate. The insulating layer may be formed on one or both of the light-transmitting substrate side and the single crystal semiconductor substrate side. The insulating layer formed on a surface that forms a bond has a smooth surface and forms a hydrophilic surface. As the insulating layer, a silicon oxide film can be used. As the silicon oxide film, it is preferable to use a silicon oxide film formed by chemical vapor deposition using an organosilane gas. Besides, a silicon oxide film formed by chemical vapor deposition using a silane gas can also be used.

As the organosilane gas, the following silicon-containing compounds can be used: tetraethoxysilane (TEOS) (chemical formula: $Si(OC_2H_5)_4$), trimethylsilane (TMS: $(CH_3)_3SiH$), tetramethylsilane (chemical formula: $Si(CH_3)_4$), tetramethylcyclotetrasiloxane (TMCTS), octamethylcyclotetrasiloxane (OMCTS), hexamethyldisilazane (HMDS), triethoxysilane ($SiH(OC_2H_5)_3$), trisdimethylaminosilane ($SiH(N(CH_3)_2)_3$), and the like. Note that in the case where a silicon oxide layer is formed by chemical vapor deposition using organosilane as a source gas, it is preferable to mix a gas containing oxygen. As a gas containing oxygen, oxygen, nitrous oxide, nitrogen dioxide, or the like can be used. Furthermore, an inert gas such as argon, helium, nitrogen, or hydrogen may be mixed.

Alternatively, as the insulating layer formed on a surface that forms a bond, it is possible to use a silicon oxide film formed by chemical vapor deposition using silane such as monosilane, disilane, or trisilane as a source gas. Also in this case, it is preferable to mix a gas containing oxygen, an inert gas, or the like. The silicon oxide film that is an insulating layer to be bonded to the single crystal semiconductor layer may contain chlorine. Note that in this specification, chemical vapor deposition (CVD) includes plasma CVD, thermal CVD, and photo CVD in its category.

Further alternatively, as the insulating layer formed on a surface that forms a bond, it is possible to use silicon oxide formed by heat treatment under an oxidizing atmosphere, silicon oxide grown by reaction of an oxygen radical, chemical oxide formed using an oxidizing chemical solution, or the like. As the insulating layer, an insulating layer including a siloxane (Si—O—Si) bond may also be used. Alternatively, the organosilane gas may be reacted with an oxygen radical or a nitrogen radical to form the insulating layer.

The surface of the insulating layer, which is to be bonded, preferably has an arithmetic mean roughness $R_a$ of less than 0.8 nm and a root-mean-square roughness $R_{ms}$ of less than 0.9 nm, more preferably, $R_a$, 0.4 nm or less and $R_{ms}$, 0.5 nm or less, and still more preferably, $R_a$, 0.3 nm or less and $R_{ms}$, 0.4 nm or less. For example, $R_a$ is 0.27 nm and $R_{ms}$ is 0.34 nm. In this specification, $R_a$ is arithmetic mean roughness, $R_{ms}$ is root-mean-square roughness, and the measurement range is 2 μm$^2$ or 10 μm$^2$.

When the light-transmitting substrate and the single crystal semiconductor substrate are bonded to each other, an insulating layer including a silicon oxide film that is deposited using organosilane as a raw material is preferably provided on one or both of the bonded surfaces, which leads to strong bonding.

Figure 16B:
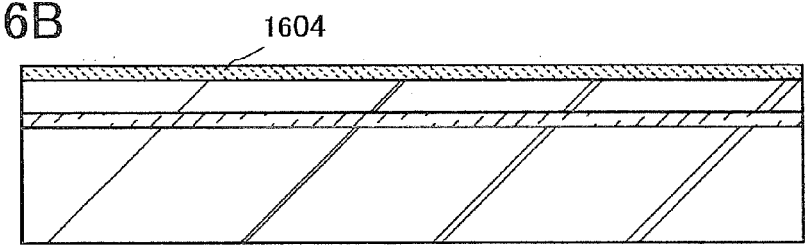

In this embodiment, as illustrated in FIG. 16B, a silicon oxide film is formed as an insulating layer 1604 on a surface bonded to the light-transmitting substrate. As the silicon oxide film, it is preferable to use a silicon oxide film formed by chemical vapor deposition using an organosilane gas. Besides, a silicon oxide film formed by chemical vapor deposition using a silane gas can also be used. The deposition by chemical vapor deposition is performed at a temperature of, for example, 350° C. or lower (specifically, 300° C. for example), which is the temperature at which the embrittlement layer 1610 formed in the single crystal semiconductor substrate is not degassed. Heat treatment for separating the single crystal semiconductor layer from the single crystal semiconductor substrate is performed at a temperature higher than the deposition temperature.

The light-transmitting substrate may be provided with a silicon nitride film or a silicon nitride oxide film as a blocking layer (also referred to as a barrier layer) for preventing diffusion of impurity elements. Furthermore, a silicon oxynitride film may also be provided in combination as an insulating film having a function of reducing stress.

Figure 16C:
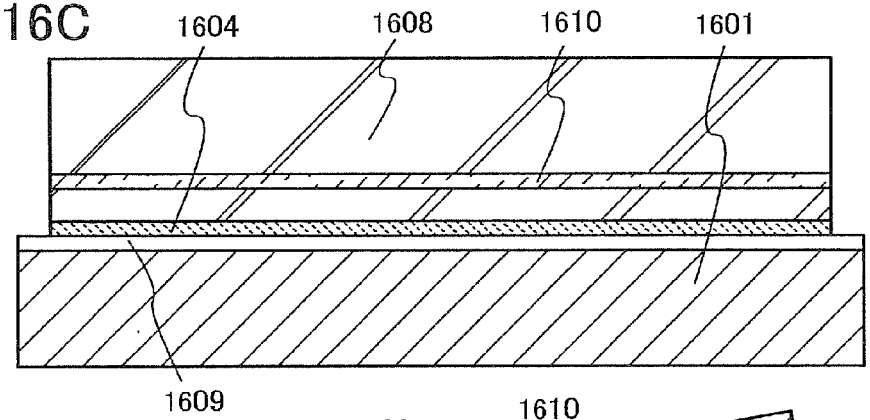

FIG. 16C illustrates a mode in which a blocking layer 1609 formed on a light-transmitting substrate 1601 is brought into close contact with and bonded to the surface of the single crystal semiconductor substrate 1608 on which the insulating layer 1604 is formed. The bonded surfaces are sufficiently cleaned. The blocking layer 1609 formed on the light-transmitting substrate 1601 and the surface of the single crystal semiconductor substrate 1608 on which the insulating layer 1604 is formed may be cleaned by megasonic cleaning or the like. In addition, the bonded surfaces may be cleaned with ozone water after megasonic cleaning, so as to remove organic substances and improve the hydrophilicity of the surfaces.

By making the blocking layer 1609 over the light-transmitting substrate 1601 and the insulating layer 1604 face each other and pressing one part thereof from the outside, the blocking layer 1609 and the insulating layer 1604 attract each other by increase in van der Waals forces or influence of hydrogen bonding due to local reduction in distance between the bonding surfaces. Further, since the distance between the blocking layer 1609 over the light-transmitting substrate 1601 and the insulating layer 1604 which face each other in an adjacent region is also reduced, a region in which van der Waals forces strongly act or a region which is influenced by hydrogen bonding is increased. Accordingly, bonding proceeds and spreads to the entire bonding surfaces.

The light-transmitting substrate 1601 and the single crystal semiconductor substrate 1608 may be pressed against each other while a pressure of 100 to 5000 kPa is applied to one of the corners of the substrates. Accordingly, the bonded surfaces come close to each other, and bonding by Van der Waals forces can be changed to hydrogen bonding. When the bonded surfaces come close to each other at one point in the substrates, the bonded surfaces at the other points also come close to each other to change to hydrogen bonding; therefore, the entire bonded surfaces can be bonded by hydrogen bonding.

In order to form a favorable bond, the surfaces may be activated. For example, the bonded surfaces are irradiated with an atomic beam or an ion beam. In the case of utilizing an atomic beam or an ion beam, an inert gas neutral atom beam or inert gas ion beam of argon or the like can be used. Alternatively, plasma irradiation or radical treatment may be performed. Such surface treatment makes it easier to form a bond between different kinds of materials even at a temperature of 200 to 400° C.

Furthermore, heat treatment is preferably performed in order to increase the bonding strength of the interface between the light-transmitting substrate and the insulating layer. For example, heat treatment is performed in an oven, a furnace, or the like at a temperature of 70 to 350° C. (e.g., at 200° C. for 2 hours).

Figure 16D:
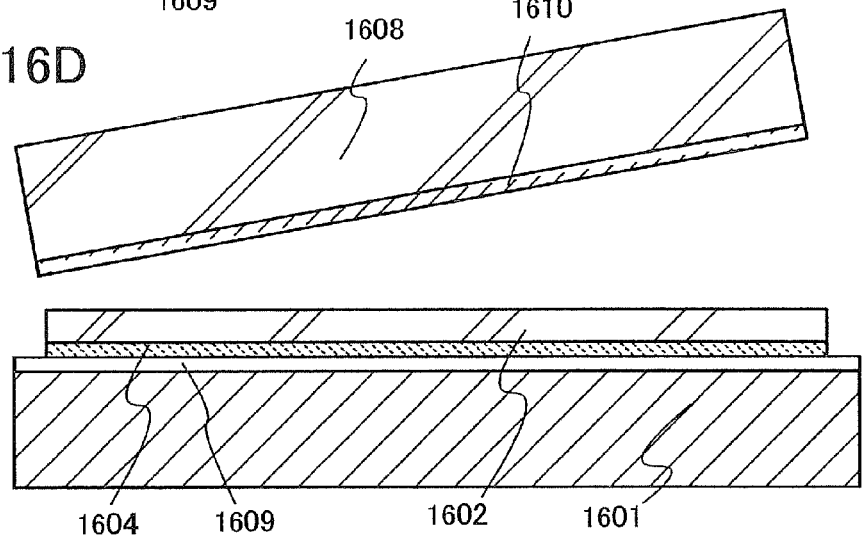

In FIG. 16D, after the light-transmitting substrate 1601 and the single crystal semiconductor substrate 1608 are bonded to each other, heat treatment is performed so that the single crystal semiconductor substrate 1608 is separated from the light-transmitting substrate 1601 using the embrittlement layer 1610 as a cleavage plane. For example, the volume change of microvoids formed in the embrittlement layer 1610 occurs by heat treatment at 400 to 700° C., which allows cleavage along the embrittlement layer 1610. Since the insulating layer 1604 is bonded to the light-transmitting substrate 1601 with the blocking layer 1609 interposed therebetween, a single crystal semiconductor layer 1602 having the same crystallinity as the single crystal semiconductor substrate 1608 remains over the light-transmitting substrate 1601.

The heat treatment in the temperature range of 400 to 700° C. may be performed sequentially using the same apparatus as used in the aforementioned heat treatment for increasing the bonding strength, or may be performed using another apparatus. For example, after heat treatment is performed in a furnace at 200° C. for 2 hours, the temperature is raised to around 600° C. and held for 2 hours, the temperature is lowered to the temperature range of room temperature to 400° C., and then the substrate is taken out of the furnace. Alternatively, the heat treatment temperature may be raised from room temperature. Further alternatively, after heat treatment is performed in a furnace at 200° C. for 2 hours, heat treatment may be performed using a rapid thermal annealing (RTA) apparatus at the temperature range of 600 to 700° C. for 1 minute to 30 minutes (e.g., at 600° C. for 7 minutes, or at 650° C. for 7 minutes).

By the heat treatment in the temperature range of 400 to 700° C., bonding between the insulating layer and the light-transmitting substrate changes from hydrogen bonding to covalent bonding, and an element added to the embrittlement layer is separated out to increase the pressure, whereby the single crystalline semiconductor layer can be separated from the single crystal semiconductor substrate. After the heat treatment, the light-transmitting substrate and the single crystal semiconductor substrate are in a state where one of them is placed over the other. Thus, the light-transmitting substrate and the single crystal semiconductor substrate can be separated from each other without strong force. For example, the substrates can be easily separated from each other by lifting one of the substrates placed upward with a vacuum chuck. In that case, the other of the substrates placed downward may be fixed with a vacuum chuck or a mechanical chuck, so that the light-transmitting substrate and the single crystal semiconductor substrate can be separated from each other without causing horizontal misalignment.

Note that FIGS. 16A to 16D and FIGS. 17A to 17C illustrate an example in which the size of the single crystal semiconductor substrate 1608 is smaller than that of the light-transmitting substrate 1601. However, the embodiment is not limited to this example, and the single crystal semiconductor substrate 1608 and the light-transmitting substrate 1601 may have the same size, or the size of the single crystal semiconductor substrate 1608 may be larger than that of the light-transmitting substrate 1601.

Figure 17A:
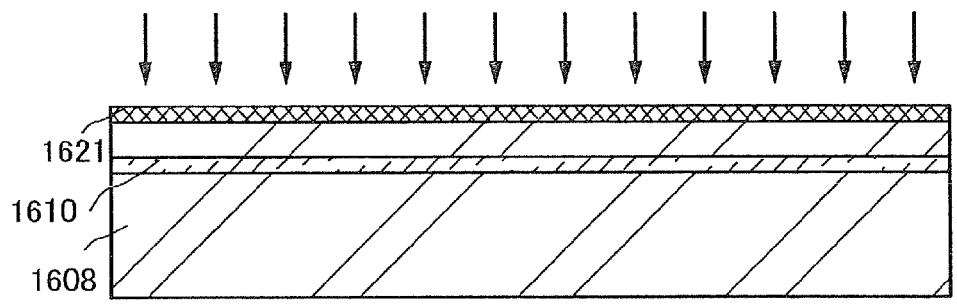
FIGS. 17A to 17C are diagrams illustrating a transistor included in a color sensor.
Figure 17B:
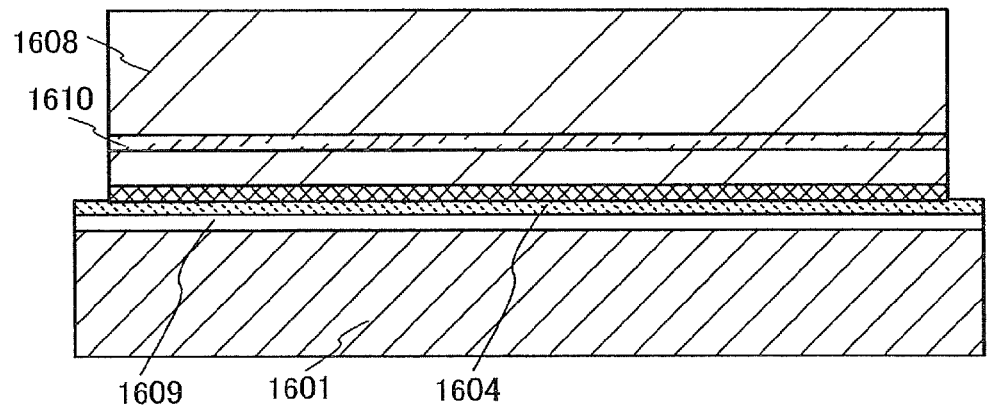
Figure 17C:
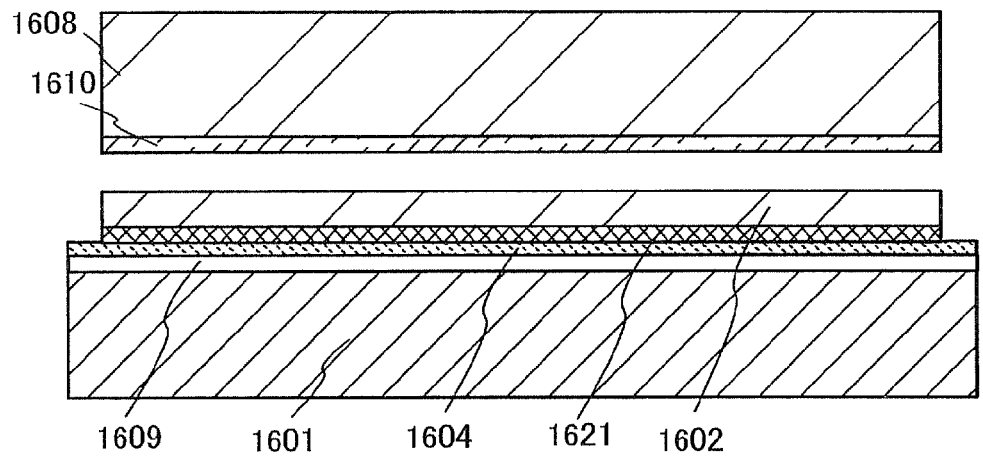

FIGS. 17A to 17C illustrate the steps of providing an insulating layer on the light-transmitting substrate side and forming a single crystal semiconductor layer. In FIG. 17A, ions accelerated by an electric field are added to a predetermined depth of the single crystal semiconductor substrate 1608 over which a silicon oxide film is formed as a protective layer 1621, whereby the embrittlement layer 1610 is formed. Ion irradiation is performed in a manner similar to that in the case of FIG. 16A. The protective layer 1621 formed over the surface of the single crystal semiconductor substrate 1608 prevents the surface from being damaged by ion irradiation and its planarity from being decreased. In addition, the protective layer 1621 has an advantageous effect of preventing diffusion of impurities into the single crystal semiconductor layer 1602 that is formed using the single crystal semiconductor substrate 1608.

In FIG. 17B, the light-transmitting substrate 1601 provided with the blocking layer 1609 and the insulating layer 1604 is brought into close contact with the surface of the single crystal semiconductor substrate 1608 on which the protective layer 1621 is formed, whereby a bond is formed. The insulating layer 1604 over the light-transmitting substrate 1601 and the protective layer 1621 on the single crystal semiconductor substrate 1608 are brought into close contact with each other, so as to form a bond.

Then, the single crystal semiconductor substrate 1608 is separated as illustrated in FIG. 17C. Heat treatment for separating the single crystal semiconductor layer is performed in a manner similar to that in the case of FIG. 16D. Thus, a semiconductor substrate having an SOI structure of this embodiment in which the single crystal semiconductor layer is formed over the substrate with the insulating layer interposed therebetween can be obtained as illustrated in FIG. 17C.

The single crystal semiconductor layer that is separated from the single crystal semiconductor substrate and transferred to the light-transmitting substrate may have crystal defects due to the separation step and the ion irradiation step, and the planarity of the surface thereof may be decreased and projections and depressions are formed. In the case where a transistor is manufactured as a semiconductor element by using the single crystal semiconductor layer, it is difficult to form a thin gate insulating layer with a high withstand voltage on the surface of such a single crystal semiconductor layer having projections and depressions. In addition, crystal defects in the single crystal semiconductor layer adversely affect the performance and reliability of the transistor; for example, the local interface state density with the gate insulating layer increases.

Therefore, it is preferable that the single crystal semiconductor layer be irradiated with electromagnetic waves such as laser light to reduce crystal defects. By irradiation with electromagnetic waves, at least part of the single crystal semiconductor layer can be melted to reduce crystal defects in the single crystal semiconductor layer. Note that before irradiation with electromagnetic waves, an oxide film (a native oxide film or a chemical oxide film) formed on the surface of the single crystal semiconductor layer may be removed with dilute hydrofluoric acid.

Any electromagnetic wave may be used as long as the single crystal semiconductor layer is provided with high energy, and preferably, laser light is used.

The energy can also be supplied mainly by heat conduction caused by making particles having high energy collide with the single crystal semiconductor layer by irradiation or the like. As a heat source for supplying particles having high energy, plasma can be used, and normal-pressure plasma, high-pressure plasma, a thermal plasma jet, or a flame of a gas burner or the like can be used. As another heat source, an electron beam or the like can be used.

The electromagnetic waves have such a wavelength as to be absorbed by the single crystal semiconductor layer. The wavelength can be determined in consideration of the skin depth of the electromagnetic waves, or the like. For example, the electromagnetic waves can have a wavelength of 190 to 600 nm. In addition, the energy of the electromagnetic waves can be determined in consideration of the wavelength of the electromagnetic waves, the skin depth of the electromagnetic waves, the thickness of the single crystal semiconductor layer to be irradiated with the electromagnetic waves, or the like.

As a laser emitting laser light, a continuous-wave laser, a pseudo continuous-wave laser, or a pulsed laser can be used. A pulsed laser is preferably used for partial melting. For example, an excimer laser such as a KrF laser, or a gas laser such as an Ar laser or a Kr laser can be used. Besides, it is possible to use a solid-state laser such as a YAG laser, a $YVO_4$ laser, a YLF laser, a $YAlO_3$ laser, a $GdVO_4$ laser, a KGW laser, a KYW laser, an alexandrite laser, a Ti:sapphire laser, or a $Y_2O_3$ laser. Note that an excimer laser is a pulsed laser, and some solid-state lasers such as a YAG laser can be used as a continuous-wave laser, a pseudo continuous-wave laser, or a pulsed laser. When the solid-state laser is used, the second to fifth harmonics of a fundamental wave are preferably used. Alternatively, a semiconductor laser such as GaN, GaAs, GaAlAs, or InGaAsP can also be used.

Lamp light may be used as long as the single crystal semiconductor layer can be irradiated with the energy of electromagnetic waves. For example, it is possible to use light emitted from an ultraviolet lamp, a black light, a halogen lamp, a metal halide lamp, a xenon arc lamp, a carbon arc lamp, a high-pressure sodium lamp, or a high-pressure mercury lamp. A flash annealing process may be performed using the above lamp light. Since the flash annealing process preferably performed using a halogen lamp, a xenon lamp, or the like requires only a very short time, increase in temperature of the light-transmitting substrate can be suppressed.

A shutter, a reflector such as a mirror or a half mirror, or an optical system including a cylindrical lens, a convex lens, and the like may be provided to adjust the shape or path of electromagnetic waves.

Note that electromagnetic waves may be emitted selectively, or scanning with light (electromagnetic waves) may be performed in the X-Y directions to be emitted. In this case, a polygon mirror or a galvanometer mirror is preferably used in the optical system.

Irradiation with electromagnetic waves can be performed in an atmosphere containing oxygen such as an atmospheric air, or in an inert atmosphere such as a nitrogen atmosphere. To perform irradiation with electromagnetic waves in an inert atmosphere, electromagnetic waves may be emitted in an airtight chamber while controlling the atmosphere in this chamber. In the case where a chamber is not used, a nitrogen atmosphere can be formed by spraying an inert gas such as nitrogen gas on a surface to be irradiated with electromagnetic waves.

Furthermore, polishing treatment may be performed on the surface of the single crystal semiconductor layer, which is provided with high energy such as electromagnetic waves to reduce crystal defects. The planarity of the surface of the single crystal semiconductor layer can be improved by the polishing treatment.

As the polishing treatment, chemical mechanical polishing (CMP) or liquid jet polishing can be performed. Note that the surface of the single crystal semiconductor layer is cleaned to be purified before the polishing treatment. The cleaning may be performed by megasonic cleaning, two-fluid jet cleaning, or the like, and dust or the like on the surface of the single crystal semiconductor layer is removed by the cleaning. In addition, it is preferable that a native oxide film or the like on the surface of the single crystal semiconductor layer be removed with dilute hydrofluoric acid to expose the single crystal semiconductor layer.

In addition, polishing treatment (or etching treatment) may also be performed on the surface of the single crystal semiconductor layer before irradiation with electromagnetic waves.

Furthermore, when a single crystal semiconductor layer is transferred from the single crystal semiconductor substrate, the single crystal semiconductor substrate may be selectively etched to process of the shape so that a plurality of single crystal semiconductor layers are transferred to the light-transmitting substrate. In this case, a plurality of island-like single crystal semiconductor layers can be provided over the light-transmitting substrate. Since the shape of the single crystal semiconductor substrate is processed in advance and then the single crystal semiconductor layers are transferred, there is no limitation on the size and shape of the single crystal semiconductor substrate. Accordingly, the single crystal semiconductor layers can be transferred to a large light-transmitting substrate more efficiently.

Alternatively, a single crystal semiconductor layer bonded to the light-transmitting substrate may be etched so that the shape of the single crystal semiconductor layer is processed, modified, and controlled precisely. As a result, the single crystal semiconductor layer can be processed into shapes of single crystal semiconductor layers of a semiconductor element. It is thus possible to correct errors in the position and shape of the single crystal semiconductor layers, which are caused by pattern misalignment due to light exposure going around a resist mask in the formation of the resist mask, positional misalignment due to a bonding step in the transferring process, or the like.

Therefore, a plurality of single crystal semiconductor layers each having a desired shape can be formed over the light-transmitting substrate at a high yield. Thus, an optical sensor including more accurate and higher performance semiconductor element and integrated circuit can be manufactured over a large substrate with high throughput and high productivity.

Alternatively, a single crystal semiconductor layer may be separated from the single crystal semiconductor substrate before being bonded to the light-transmitting substrate. The single crystal semiconductor layer may be bonded to the light-transmitting substrate so that a surface of the single crystal semiconductor layer that is exposed by cleavage faces the light-transmitting substrate or is in contact with a gate insulating film.

In this embodiment mode, when a single crystal silicon substrate is used as the single crystal semiconductor substrate 1608, a single crystal silicon layer can be obtained as the single crystal semiconductor layer 1602. In addition, the method of manufacturing an optical sensor of this embodiment can be performed at a process temperature of 700° C. or lower; thus, a glass substrate can be used as the light-transmitting substrate 1601. That is, a transistor can be formed over a glass substrate similarly to a conventional thin film transistor, and further a single crystal silicon layer can be used as a semiconductor layer. Accordingly, a high-performance and high-reliability transistor, which is capable of high-speed operation and has a low subthreshold value, a high field-effect mobility, and low power consumption, can be manufactured over the light-transmitting substrate such as a glass substrate.

This embodiment can be combined with Embodiment 1 as appropriate.

(Embodiment Mode 4)

Described in this embodiment is an example of the process of bonding a single crystal semiconductor layer from a single crystal semiconductor substrate to a light-transmitting substrate, which is different from that described in Embodiment 2. Therefore, description of the same portions or portions having a function similar to those described in Embodiment 2 is omitted.

First, the processing of a single crystal substrate side will be described. In this embodiment, a single crystal semiconductor substrate is degreased and cleaned to remove an oxide film of the surface, and then thermal oxidation is performed. As the thermal oxidation, it is preferable to perform oxidation in an oxidizing atmosphere to which halogen is added. For example, heat treatment is performed at a temperature of 700° C. or higher in an atmosphere that contains HCl at 0.5 to 10% by volume (preferably, 3% by volume) with respect to oxygen. Preferably, thermal oxidation is performed at a temperature of 950 to 1100° C. Processing time may be set to 0.1 to 6 hours, and preferably 0.5 to 3.5 hours. An oxide film to be formed has a thickness of 10 to 1000 nm (preferably, 50 to 200 nm), for example, 100 nm.

As a substance containing halogen, one or more selected from HF, $NF_3$, HBr, $Cl_2$, $ClF_3$, $BCl_3$, $F_2$, $Br_2$, and the like can be used instead of HCl.

When heat treatment is performed in such a temperature range, a gettering effect by a halogen element can be obtained. Gettering particularly has an effect of removing a metal impurity. That is, by the action of chlorine, impurities such as metal turn into a volatile chloride, and then are diffused into the air to be removed. It has an advantageous effect on the surface of the single crystal semiconductor substrate that is subjected to chemical mechanical polishing (CMP) treatment. In addition, hydrogen has an effect of compensating a defect at the interface between the single crystal semiconductor substrate and an insulating layer formed over a light-transmitting substrate, so as to lower a localized-level density at the interface, whereby the interface between the single crystal semiconductor substrate and the insulating layer is inactivated to stabilize electric characteristics.

Halogen can be contained in the oxide film formed by this heat treatment. When a halogen element is contained at a concentration of $1\times10^{17}$ atoms/cm$^3$ to $5\times10^{20}$ atoms/cm$^3$, the oxide film can function as a protective layer that traps impurities such as metal and prevents contamination of the single crystal semiconductor substrate.

Ions are introduced into the single crystal semiconductor substrate to form an embrittlement layer. The depth at which the embrittlement layer is formed can be adjusted by the acceleration energy and incidence angle of the introduced ions. The acceleration energy can be controlled by accelerating voltage, dosage, or the like.

A hydrogen gas, a rare gas, or the like can be used for introducing ions. In this embodiment mode, a hydrogen gas is preferably used. When ion doping is performed using a hydrogen gas, H$^+$ ions, H$_2^+$ ions, and H$_3^+$ ions are generated, and it is preferable that the proportion of H$_3^+$ ions be the highest among them. H$_3^+$ ions can be introduced with a higher efficiency than H$^+$ ions and H$_2^+$ ions, and introduction time can be shortened. In addition, cracks are easily generated in the embrittlement layer in a subsequent step.

Next, the processing of a light-transmitting substrate is described. First, a surface of the light-transmitting substrate is cleaned. The surface may be cleaned by ultrasonic cleaning using hydrochloric acid/hydrogen peroxide mixture (HPM), sulfuric acid/hydrogen peroxide mixture (SPM), ammonium hydroxide/hydrogen peroxide mixture (APM), dilute hydrofluoric acid (DHF), or the like. In this embodiment mode, ultrasonic cleaning is performed using hydrochloric acid/hydrogen peroxide mixture.

Then, the light-transmitting substrate that has been cleaned to remove impurities such as dust on the surface thereof is subjected to planarizing treatment by plasma treatment. In this embodiment mode, the plasma treatment is performed in a vacuum chamber in such a manner that an inert gas such as an argon (Ar) gas is used and bias voltage is applied to the light-transmitting substrate to be processed, whereby plasma is generated. In addition to an inert gas, an oxygen (O$_2$) gas and a nitrogen (N$_2$) gas may be introduced.

The light-transmitting substrate is set to be in the cathode direction, and positive ions of Ar in the plasma are accelerated to the cathode direction to collide with the light-transmitting substrate. By collision of the Ar positive ions, the surface of the light-transmitting substrate is sputter-etched. Accordingly, a projection on the surface of the light-transmitting substrate is etched, so that the surface of the light-transmitting substrate can be planarized. A reactive gas has an advantageous effect of repairing defects caused by sputter etching of the surface of the light-transmitting substrate.

Next, an insulating layer is formed over the light-transmitting substrate. In this embodiment mode, an oxide film containing aluminum oxide as its main component, which is an insulating layer except silicon-based insulating layers, is used. The oxide film containing aluminum oxide as its main component refers to an oxide film that contains at least 10 wt. % of aluminum oxide in the case where the oxide film contains 100 wt. % of total components. Besides, a film that contains aluminum oxide as its main component and contains one or both of magnesium oxide and strontium oxide may be used as the insulating layer. Furthermore, an aluminum oxide film containing nitrogen may also be used.

The insulating layer can be formed by sputtering. As a sputtering target, for example, metal including aluminum or metal oxide such as aluminum oxide can be used. Note that the target material may be selected as appropriate depending on a film to be formed.

In the case where metal is used as a target, the insulating layer is formed by sputtering (reactive sputtering) while introducing a reaction gas (such as oxygen). As the metal, in addition to aluminum, magnesium (Mg), an alloy containing aluminum and magnesium, an alloy containing aluminum and strontium (Sr), or an alloy containing aluminum, magnesium, and strontium can be used. In this case, sputtering may be performed using a direct current (DC) power supply or a radio frequency (RF) power supply.

In the case where a metal oxide is used as the target, the insulating layer is formed by sputtering (RF sputtering) using a radio frequency (RF) power supply. As the metal oxide, in addition to aluminum oxide, magnesium oxide, strontium oxide, an oxide containing aluminum and magnesium, an oxide containing aluminum and strontium, or an oxide containing aluminum, magnesium, and strontium can be used.

Alternatively, the insulating layer may be formed by bias sputtering, which allows both deposition of a film and planarization of a surface to be achieved.

The oxide film containing aluminum as its main component can prevent impurities contained in the light-transmitting substrate, such as mobile ions or moisture, from diffusing into a single crystal semiconductor film that is to be formed later over the light-transmitting substrate.

Then, the surface of the single crystal semiconductor substrate is made to face the surface of the light-transmitting substrate, whereby the single crystal semiconductor substrate and the insulating layer are bonded to each other. The single crystal semiconductor substrate is brought into close contact with the surface of the insulating layer, whereby a bond is formed.

Note that before the single crystal semiconductor substrate and the light-transmitting substrate are bonded to each other, the surface treatment is preferably performed on the insulating layer formed over the light-transmitting substrate.

Subsequently, similarly to Embodiment Mode 2, heat treatment is performed to carry out separation (cleavage) at the embrittlement layer, whereby a single crystal semiconductor layer can be provided over the light-transmitting substrate with an insulating layer interposed therebetween.

A semiconductor element layer can be formed using the single crystal semiconductor layer provided over the light-transmitting substrate.

Next, a process of repeatedly using a separated single crystal semiconductor substrate (treatment for reprocessing a semiconductor substrate) will be described.

First, a separated single crystal semiconductor substrate is taken out. In some cases, the edge of the single crystal semiconductor substrate is not sufficiently bonded to the light-transmitting substrate due to edge roll-off. Thus, the edge of the single crystal semiconductor substrate is not separated along the embrittlement layer in some cases, and the insulating layer or the like may remain.

A residue on the edge of the single crystal semiconductor substrate is removed. The residue can be removed by wet etching. Specifically, wet etching is performed using a mixture solution containing hydrofluoric acid, ammonium fluoride, and surfactant (e.g., product name: LAL500, manufactured by Stella Chemifa Corporation) as an etchant.

The embrittlement layer into which hydrogen ions are introduced can be removed by wet etching using an organic alkaline aqueous solution typified by tetramethylammonium hydroxide (TMAH). By performing such treatment, a step due to the residue on the edge of the single crystal semiconductor substrate is reduced.

Then, the single crystal semiconductor substrate is oxidized in a halogen atmosphere to form an oxide film, and after that, the oxide film is removed. As the halogen, hydrogen chloride (HCl) can be used. Accordingly, a gettering effect by a halogen element can be obtained. Gettering particularly has an effect of removing a metal impurity. That is, by the action of chlorine, impurities such as metal turn into a volatile chloride, and then are diffused into the air to be removed.

Next, the single crystal semiconductor substrate is subjected to CMP treatment as polishing treatment. Thus, the step on the edge of the single crystal semiconductor substrate can be removed so that the surface of the single crystal semiconductor substrate is planarized. After that, the obtained single crystal semiconductor substrate is reused as a base wafer.

As described in this embodiment mode, reduction in cost can be achieved by repeatedly using a single crystal semiconductor substrate through the reprocessing steps of the single crystal semiconductor substrate. In addition, even in the case of repeatedly using a single crystal semiconductor substrate, the surface of the single crystal semiconductor substrate can be planarized sufficiently through the reprocessing steps described in this embodiment mode. Therefore, the adhesion between the single crystal semiconductor substrate and the light-transmitting substrate can be improved to reduce defective bonding.

Note that the contents described in each drawing in this embodiment can be freely combined with or replaced with the contents described in another embodiment as appropriate. Therefore, in the color sensor, the number of terminals which increases by the provision of a plurality of optical sensors can be reduced over the interposer. Specifically, a terminal to which a high power supply potential is input and a terminal electrode to which a low power supply potential is input can be made to be a common terminal over the interposer. Accordingly, the number of terminal electrodes can be significantly reduced. By reducing the number of terminal electrodes, suppression of a defect of connection with an external device can be achieved, whereby an yield can be improved. Further, the structure of this embodiment can achieve pin compatibility when the plurality of optical sensors is provided over the interposer to form the color sensor.

(Embodiment Mode 5)

In this embodiment, a variety of examples of electronic devices each of which includes a color sensor obtained according to the above embodiment are described. Examples of electronic devices include a computer, a display, a mobile phone, a television device, and the like. Specific examples of such electronic devices are shown in FIGS. 18A to 18C, FIGS. 19A and 19B, FIG. 20, and FIGS. 21A and 21B.

FIGS. 18A to 18C show a mobile phone. In FIG. 18A, the mobile phone includes a main body (A) 1801, a main body (B) 1802, a housing 1803, operation keys 1804, an audio input portion 1805, an audio output portion 1806, a circuit board 1807, a display panel (A) 1808, a display panel (B) 1809, a hinge 1810, a light-transmitting material portion 1811, and a color sensor 1812.

The color sensor 1812 detects light, which has passed through the light-transmitting material portion 1811, for each color element and controls the luminance of and adjusts color of the display panel (A) 1808 and the display panel (B) 1809 in accordance with the illuminance of the external light detected. Accordingly, current consumption of the mobile phone can be suppressed and display can be optimized in accordance with color of an external environment.

Note that the color elements are, for example, red (R), green (G), and blue (B). Light-transmitting characteristics of an optical filter provided for an optical sensor may be adjusted.

FIGS. 18B and 18C show other examples of a mobile phone. In FIG. 18B, the mobile phone includes a main body 1821, a housing 1822, a display panel 1823, operation keys 1824, an audio output portion 1825, an audio input portion 1826, and a color sensor 1827. In FIG. 18C, a color sensor 1828 is added to the above-mentioned compositions of FIG. 18B.

The mobile phone shown in FIG. 18B detects external light for each color element by using the color sensor 1827 provided in the main body 1821 so that the luminance of the display panel 1823 and the luminance of the operation keys 1824 can be controlled and display which can be optimized in accordance with color of an external environment.

Furthermore, in the mobile phone shown in FIG. 18C, the color sensor 1828 is provided inside the main body 1821 in addition to the structure of FIG. 18A. By using the color sensor 1828, the luminance of a backlight provided in the display panel 1823 can be controlled and display can be optimized in accordance with color of an external environment. In specific, in the case where color of display is adjusted by forming the backlight with an LED of three colors of red (R), green (G), and blue (B), image quality can be improved by adjusting light from the backlight with the color sensor.

Figure 19:
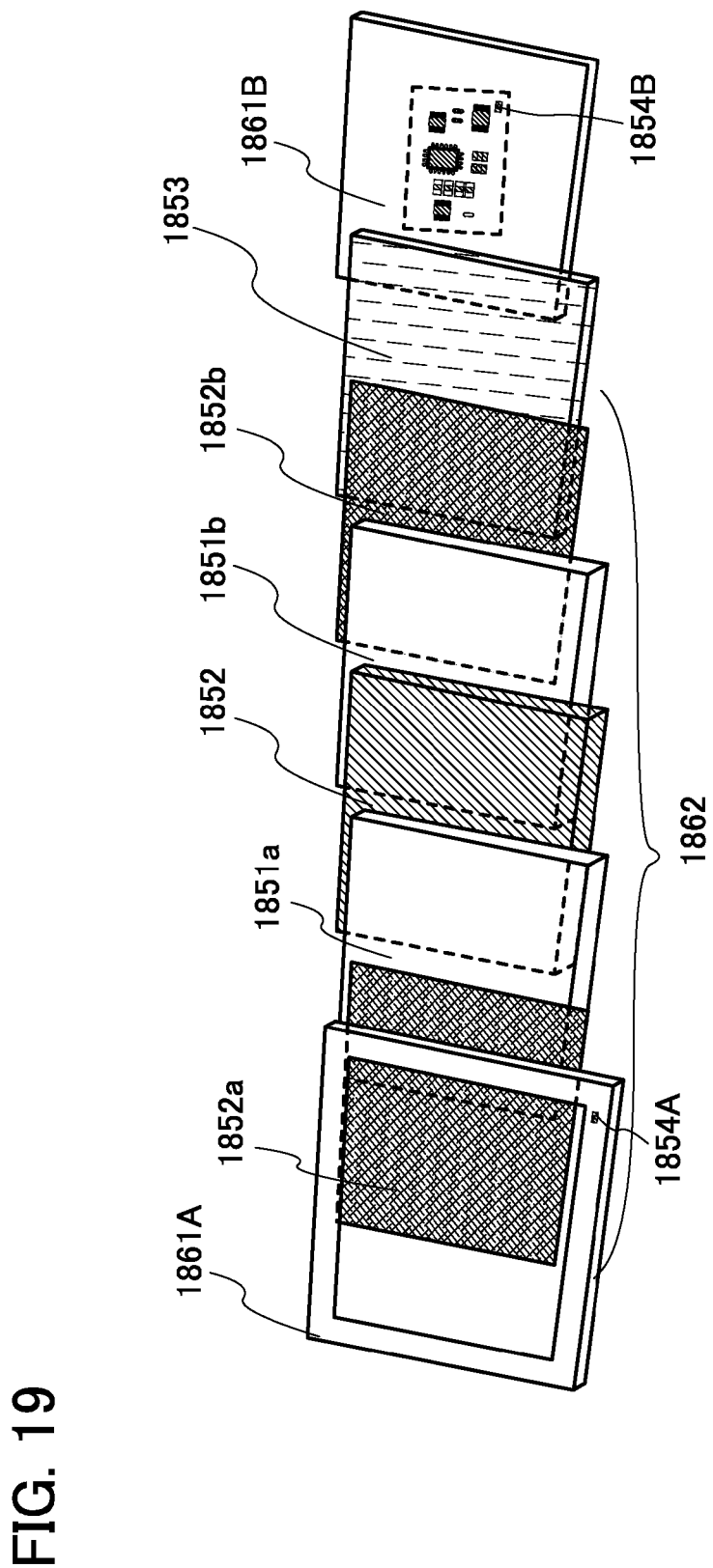
FIG. 19 is a diagram illustrating an electronic device provided with a color sensor.

A liquid crystal panel 1862 shown in FIG. 19 includes a liquid crystal layer 1852 which is provided between a housing 1861A and a backlight 1853 and is interposed between a substrate 1851a and 1851b, a polarizing filter 1852a, a polarizing filter 1852b, and the like. Further, the housing 1861A is provided with a color sensor 1854A. Furthermore, a control circuit board 1861B is provided on the back of the backlight, and the control circuit board 1861B is provided with a color sensor 1854B.

The color sensor 1854A detects external light for each color element, and information related thereto is fed back, so that the luminance of the display panel 1862 and the chromaticity of video data are corrected. Further, the color sensor 1854B detects light from the backlight 1853 for each color element to control the backlight in accordance with the illuminance of external light detected. Image quality can be improved by adjusting light from the backlight with the color sensor.

Figure 20A:
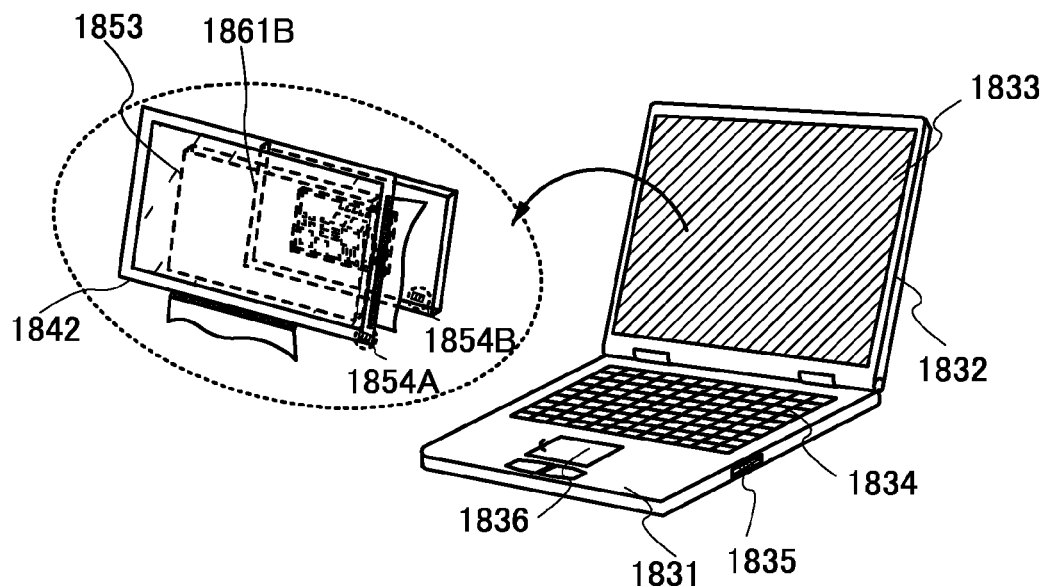
FIGS. 20A and 20B are diagrams each illustrating an electronic device provided with a color sensor.

FIG. 20A illustrates a computer including a main body 1831, a housing 1832, a display portion 1833, a keyboard 1834, an external connection port 1835, a pointing device 1836, and the like.

Figure 20B:
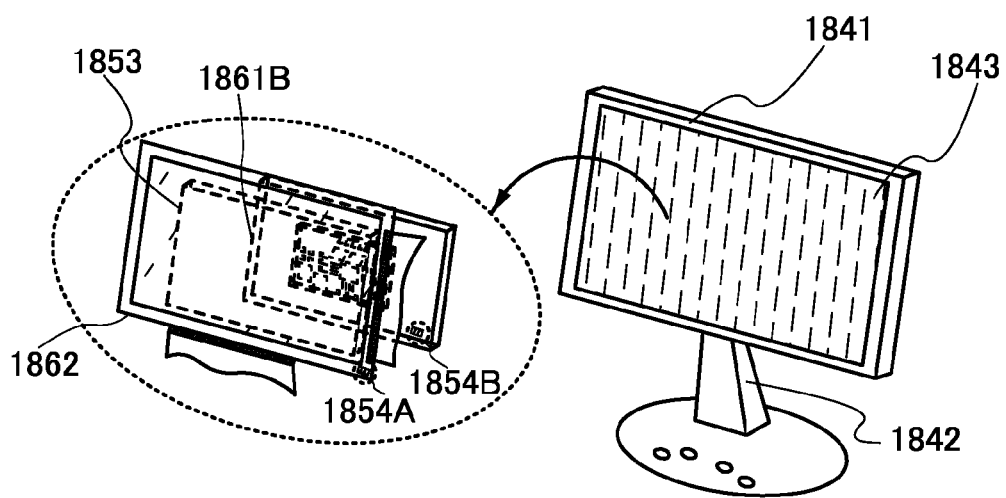

FIG. 20B illustrates a television device that is an example of a display device, which includes a housing 1841, a supporting base 1842, a display portion 1843, and the like.

As shown in FIG. 19, the display portion 1833 provided in the computer shown in FIG. 20A and the display portion 1843 in the display device in FIG. 20B each include the control circuit board 1861B in which the color sensor 1854B is provided, the back light 1853, and the liquid crystal panel 1862 in which the color sensor 1854A is provided over the substrate. Note that the color sensor 1854A provided over the substrate of the liquid crystal panel may detect light outside the housing through a light guide portion provided in the housing.

Figure 21A:
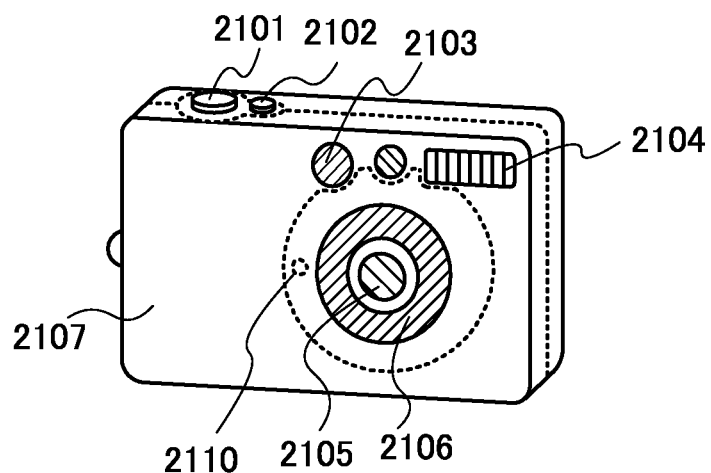
FIGS. 21A and 21B are diagrams illustrating an electronic device provided with a color sensor.
Figure 21B:
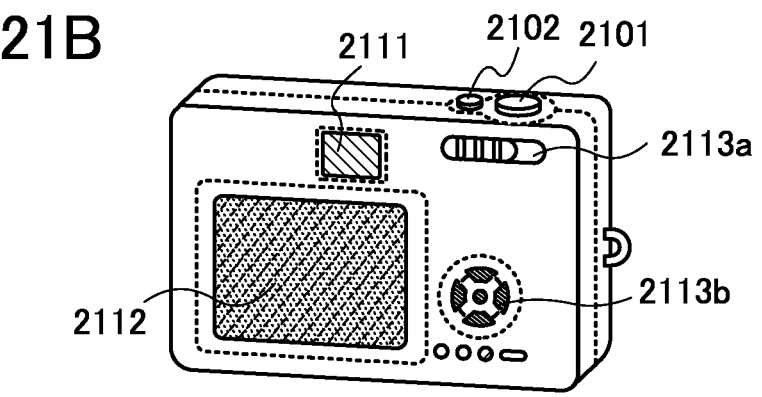

FIGS. 21A and 21B are views illustrating a camera, for example, a digital camera, which includes a color sensor 2110 according to the above embodiment. FIG. 21A is a perspective view from the front side of the digital camera, and FIG. 13B is a perspective view from the back side thereof. In FIG. 21A, the digital camera includes a release button 2101, a main switch 2102, a viewfinder 2103, a flash 2104, a lens 2105, a lens barrel 2106, a housing 2107, and the color sensor 2110.

In FIG. 21B, the digital camera includes an eyepiece finder 2111, a monitor 2112, and operation buttons 2113a and 2113b.

When the release button 2101 is pressed down halfway, a focus adjusting mechanism and an exposure adjusting mechanism are operated, and a shutter is opened when the release button 2101 is fully pressed down.

When the main switch 2102 is pressed or turned, the power of the digital camera is switched on or off.

The viewfinder 2103 is located above the lens 2105 on the front side of the digital camera, and used for checking the shooting range and the focus point from the eyepiece finder 2111 illustrated in FIG. 21B.

The flash 2104 is located in the upper portion of the front side of the digital camera. When the subject brightness is low, auxiliary light is emitted from the flash 2104 at the same time as the release button is pressed down to open the shutter.

The lens 2105 is located on the front of the digital camera. The lens 2105 includes a focusing lens, a zoom lens, and the like, and forms a photographic optical system with a shutter and a diaphragm that are not illustrated. In addition, an image pickup device such as a CCD (charge coupled device) is provided behind the lens.

The lens barrel 2106 moves the lens to focus the focusing lens, the zoom lens, and the like. In taking photographs, the lens barrel 2106 is slid out to move the lens 2105 forward. When carrying the digital camera, the lens 2105 is moved backward to be compact. Note that the structure in which the object is zoomed in by sliding out the lens barrel is shown in this embodiment; however, the present invention is not limited to this structure. The digital camera may have another structure in which the object is zoomed in without sliding out the lens barrel by using the optical system inside the housing 2107.

The eyepiece finder 2111 is located in the upper portion of the back side of the digital camera. The shooting range and the focus point are checked by looking through the eyepiece finder 2111.

The operation buttons 2113 are located on the back side of the digital camera and have various functions, which include a set-up button, a menu button, a display button, a functional button, a selection button, and the like.

By incorporating the color sensor 2110 described in the above embodiment in the cameras described in FIGS. 21A and 21B, the color sensor 2110 can determine existence or nonexistence of light and detect the intensity of light for each color element, whereby exposure and color tone for a camera can be adjusted. Since the color sensor according to the above embodiment is thin, the device can be small even when the color sensor is mounted on. Miniaturization of a component such as the color sensor is effective particularly when the component is used for portable electronic appliances.

The color sensor described in the above embodiment can be applied to other electronic devices such as projection TVs and navigation systems. In other words, the semiconductor device disclosed in this specification can be applied to any device that needs to detect light.

Note that the contents described in each drawing in this embodiment can be freely combined with or replaced with the contents described in another embodiment as appropriate. Therefore, in the color sensor, the number of terminals which increases by the provision of a plurality of optical sensors can be reduced over the interposer. Specifically, a terminal to which a high power supply potential is input and a terminal electrode to which a low power supply potential is input can be made to be a common terminal over the interposer. Accordingly, the number of terminal electrodes can be significantly reduced. By reducing the number of terminal electrodes, suppression of a defect of connection with an external device can be achieved, whereby an yield can be improved. Further, the structure of this embodiment can achieve pin compatibility when the plurality of optical sensors is provided over the interposer to form the color sensor.

This application is based on Japanese Patent Application serial no. 2008-180776 filed with Japan Patent Office on Jul. 10, 2008, the entire contents of which are hereby incorporated by reference.

What is claimed is:

1. A semiconductor device comprising:
   an interposer;
   a plurality of wirings on the interposer; and
   an optical sensor over the interposer and the plurality of wirings, the optical sensor comprising:
      a plurality of photoelectric conversion circuit portions over the interposer, each photoelectric conversion circuit portion comprising a semiconductor element layer and electrodes electrically connected to the semiconductor element layer;
      a light-transmitting substrate over the plurality of photoelectric conversion circuit portions; and
      a plurality of optical filters over the plurality of photoelectric conversion circuit portions with the light-transmitting substrate interposed therebetween,
   wherein each of the electrodes is on and in direct contact with a corresponding one of the plurality of wirings,
   wherein light-transmitting characteristics of the plurality of optical filters are different from each other.

2. The semiconductor device according to claim 1, wherein in the plurality of wirings, a first wiring has a plurality of branches for electrical connection between a first terminal electrode and the optical sensor, and a second wiring has a plurality of branches for electrical connection between a second terminal electrode and the optical sensor.

3. The semiconductor device according to claim 2, wherein the first terminal electrode is for inputting a high power supply potential and the second terminal electrode is for inputting a low power supply potential.

4. The semiconductor device according to claim 1, wherein a material of the interposer is selected from a group consisting of an organic polymer, an inorganic polymer, glass epoxy, ceramics, polyimide, and a fluorine resin.

5. The semiconductor device according to claim 1, further comprising a resin between the optical sensor and the interposer, the resin filling spaces between the plurality of photoelectric conversion circuit portions.

6. An electronic device having a color sensor including the semiconductor device according to claim 1.

7. A semiconductor device comprising:
   an interposer;
   a plurality of wirings on a first surface of the interposer;
   a plurality of terminal electrodes on a second surface of the interposer; and
   an optical sensor over the first surface of the interposer and the plurality of wirings, the optical sensor comprising:
      a plurality of photoelectric conversion circuit portions over the interposer, each photoelectric conversion circuit portion comprising a semiconductor element layer and electrodes electrically connected to the semiconductor element layer;
      a light-transmitting substrate on the plurality of photoelectric conversion circuit portions; and
      a plurality of optical filters on the light-transmitting substrate,
   wherein each of the electrodes is on and in direct contact with a corresponding one of the plurality of wirings, wherein the plurality of terminal electrodes electrically connect to the optical sensor through the plurality of wirings, and wherein light-transmitting characteristics of the plurality of optical filters are different from each other.

8. The semiconductor device according to claim 7, wherein in the plurality of wirings, a first wiring has a plurality of branches for electrical connection between a first one of the plurality of terminal electrodes and the optical sensor, and a second wiring has a plurality of branches for electrical connection between a second one of the plurality of terminal electrodes and the optical sensor.

9. The semiconductor device according to claim 8, wherein the first one of the plurality of terminal electrodes is for inputting a high power supply potential and the second one of the plurality of terminal electrodes is for inputting a low power supply potential.

10. The semiconductor device according to claim 7, wherein a material of the interposer is selected from a group consisting of an organic polymer, an inorganic polymer, glass epoxy, ceramics, polyimide, and a fluorine resin.

11. The semiconductor device according to claim 7, wherein the plurality of terminal electrodes and the plurality of photoelectric conversion circuit portions are not overlapped each other.

12. The semiconductor device according to claim 7, further comprising a resin between the optical sensor and the interposer, the resin filling spaces between the plurality of photoelectric conversion circuit portions.

13. An electronic device having a color sensor including the semiconductor device according to claim 7.

14. A semiconductor device comprising:
an interposer;
a plurality of wirings on a first surface of the interposer;
an optical sensor over the first surface of the interposer and the plurality of wirings, the optical sensor comprising:
first to third photoelectric conversion circuit portions over the interposer, each of the first to third photoelectric conversion circuit portions comprising a semiconductor element layer and electrodes electrically connected to the semiconductor element layer;
a light-transmitting substrate on the first to third photoelectric conversion circuit portions; and
R, G, and B optical filters on the light-transmitting substrate, wherein each of the electrodes is on and in direct contact with a corresponding one of the plurality of wirings.

15. The semiconductor device according to claim 14, further comprising a plurality of terminal electrodes over a second surface of the interposer,
wherein the plurality of terminal electrodes electrically connect to the optical sensor through the plurality of wirings.

16. The semiconductor device according to claim 15, wherein in the plurality of wirings, a first wiring has a plurality of branches for electrical connection between a first one of the plurality of terminal electrodes and the optical sensor, and a second wiring has a plurality of branches for electrical connection between a second one of the plurality of terminal electrodes and the optical sensor.

17. The semiconductor device according to claim 16, wherein the first one of the plurality of terminal electrodes is for inputting a high power supply potential and the second one of the plurality of terminal electrodes is for inputting a low power supply potential.

18. The semiconductor device according to claim 14, wherein a material of the interposer is selected from a group consisting of an organic polymer, an inorganic polymer; glass epoxy, ceramics, polyimide, and a fluorine resin.

19. The semiconductor device according to claim 14, further comprising a resin between the optical sensor and the interposer, the resin filling spaces between the first to third photoelectric conversion circuit portions.

20. An electronic device having a color sensor including the semiconductor device according to claim 14.

* * * * *